US010047364B2

(12) United States Patent
Schröder et al.

(10) Patent No.: US 10,047,364 B2
(45) Date of Patent: Aug. 14, 2018

(54) RECOMBINANT MICROORGANISM FOR IMPROVED PRODUCTION OF FINE CHEMICALS

(71) Applicant: BASF SE, Ludwigshafen (DE)

(72) Inventors: Hartwig Schröder, Nußloch (DE);
Holger Hartmann, Schwetzingen (DE);
Qingzhao Wang, Ardsley, NY (US);
Shakir Ratani, Tarrytown, NY (US);
Zheyuan Guo, Tarrytown, NY (US);
Markus Pompejus, San Diego, CA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/024,464

(22) PCT Filed: Sep. 11, 2014

(86) PCT No.: PCT/IB2014/064426
§ 371 (c)(1),
(2) Date: Mar. 24, 2016

(87) PCT Pub. No.: WO2015/044818
PCT Pub. Date: Apr. 2, 2015

(65) Prior Publication Data
US 2016/0355829 A1 Dec. 8, 2016

Related U.S. Application Data

(60) Provisional application No. 61/881,968, filed on Sep. 25, 2013, provisional application No. 61/881,969, filed on Sep. 25, 2013, provisional application No. 61/881,975, filed on Sep. 25, 2013, provisional application No. 61/881,972, filed on Sep. 25, 2013.

(51) Int. Cl.
*C12N 1/20* (2006.01)
*C12N 15/70* (2006.01)
*C07K 14/245* (2006.01)
*C12P 13/06* (2006.01)
*C12P 7/46* (2006.01)
*C12N 9/02* (2006.01)
*C12N 9/16* (2006.01)
*C12P 7/40* (2006.01)
*C12P 7/56* (2006.01)
*C12P 13/08* (2006.01)
*C12P 13/20* (2006.01)

(52) U.S. Cl.
CPC ............ *C12N 15/70* (2013.01); *C07K 14/245* (2013.01); *C12N 9/0036* (2013.01); *C12N 9/16* (2013.01); *C12P 7/40* (2013.01); *C12P 7/46* (2013.01); *C12P 7/56* (2013.01); *C12P 13/06* (2013.01); *C12P 13/08* (2013.01); *C12P 13/20* (2013.01)

(58) Field of Classification Search
CPC C12P 13/06; C12Y 104/01001; C12N 9/0016
USPC ........................................................ 435/183
See application file for complete search history.

(56) References Cited

U.S. PATENT DOCUMENTS

| 8,129,169 | B2 | 3/2012 | Van Dien et al. |
| 9,109,244 | B2 | 8/2015 | Pompejus et al. |
| 9,434,964 | B2 | 9/2016 | Van Dien et al. |
| 2011/0302673 | A1 | 12/2011 | McKersie et al. |
| 2015/0376663 | A1 | 12/2015 | Schroeder et al. |
| 2016/0355829 | A1* | 12/2016 | Schroder .............. C07K 14/245 |
| 2016/0355846 | A1 | 12/2016 | Van Dien et al. |

FOREIGN PATENT DOCUMENTS

| CN | 1981045 A | 6/2007 |
| CN | 102224165 A | 10/2011 |
| CN | 102498215 A | 6/2012 |
| WO | WO-97/44481 A1 | 11/1997 |
| WO | WO-2010/034652 A1 | 4/2010 |
| WO | WO-2012/172822 A1 | 12/2012 |
| WO | WO-2015/028915 A1 | 3/2015 |
| WO | WO-2015/044818 A1 | 4/2015 |
| WO | WO-2015/087226 A1 | 6/2015 |

OTHER PUBLICATIONS

Extended European Search Report, European patent application No. 14847532.0, dated Jul. 19, 2017.
Abe et al., A recombinant microorganism and a method for producing L-alanin using the same, Geneseq [Online] Database accession No. HW057551 (Jun. 17, 2013).
Bruce et al., *Escherichia coli* B2670 gene, SEQ ID:21, Database Accession No. AXX46147, Geneseq [Online] Database (May 27, 2010).
Bruce et al., *Escherichia coli* B2670 protein, SEQ ID:22, Database Accession No. AXX46147, Geneseq [Online] Database (May 27, 2010).
Hiroshi et al., *Escherichia coli*, Ygaw protein sequence, SEQ ID 2, Database Accession No. BAJ34236, Geneseq [Online] Database (Feb. 14, 2013).
Hori et al., Inducible I-alanine exporter encoded by the novel gene ygaW (alaE) in *Escherichia coli*, Appl. Env. Microbiol., 22(12):4027-34 (2011).
Partial Supplementary European Search Report, European patent application No. 14847532.0, dated Apr. 11, 2017.
Schroeder et al., 11 *Escherichia coli* ygaW coding DNA, SEQ ID 109, Database Accession No. BCB16045, Geneseq [Online] Database (Jun. 18, 2015).
Schroeder et al., *Escherichia coli* ygaW polypeptide, SEQ ID 110, Database Accession No. BCB16046, Geneseq [Online] Database (Jun. 18, 2015).

(Continued)

Primary Examiner — Tekchand Saidha
(74) Attorney, Agent, or Firm — Marshall, Gerstein & Borun LLP

(57) ABSTRACT

The present invention relates to a recombinant nucleic acid molecule, a recombinant microorganism, to a method for producing alanine and to the use of the recombinant nucleic acid molecule or the recombinant microorganism for the fermentative production of alanine.

8 Claims, 31 Drawing Sheets

(56) References Cited

OTHER PUBLICATIONS

GenBank accession No. WP_011232226.1, Multispecies: alanine dehydrogenase [Geobacillus] (May 15, 2013).
Hermann, Industrial production of amino acids by coryneform bacteria, J. Biotechnol., 104:155-72 (2003).
International Preliminary Report on Patentability, International Application No. PCT/IB2014/064426, dated Mar. 29, 2016.
International Search Report and Written Opinion, International Application No. PCT/IB2014/064426, dated Jan. 28, 2015.

* cited by examiner

```
                                                                                              <yfbV
GTCTTTGAGTAATGCGTCCCCGGCGAAACAAGCTAAAAAAAATTAACAGAACCGATTATCCGGCGTTGACATGCTTCACCTCAACTTCACATATAAAGATT
caaaaatttgtcaaattcacaactcagcgggacaacgttcaaaacattgtcttccataaccactcaggtatcctttagcagcctgaaggcctaagtacata
ttcattggtcgtcaaattcatatacattatgccattgcctgctgtacggcatctcctcccctgacgtttttttagccacgtatcaattataggtactt
gatgttaatcataaatgtcggtgtcatcatgcgctacgctctatggctctctatgctctccctgacgtttttttagccacgtatcaattataggtactt
                                                                                              ackA>
                                                                                     ATGTGCGAGTAAGTTAGT
                                                                                     ▶MetSerSerLysLeuVa
      P395-ackA-pta-check1>                                                P395-ackA-pta-check2>
ACTGGTTCTGAACTGCGGGTAGTTCTTCACTGAAATTTGCCATCATCGATGCAGTAAATGGTGAAGAGTACCTTTCTGGTTTAGCCGAATGTTTCCAC
▶lLeuValLeuAsnCysSerLeuLysSerLeuLysPheAlaIleIleAspAlaValAsnGlyLeuGluTyrLeuSerGlyLeuAlaGluCysPheHis
CTGCCCGAAGCACGTATCAAAATGGAAATGGACAATAAACAGGAAGCGGCTTTAGGTCAGGCGCCTTTAGGTCAGGCGGCCTCAAGGCCTCAACTTTATCa
▶LeuProGluAlaArgIleLysMetAspGlyMetAspGlyAsnLysGlnGluAlaAlaLeuGlyGlyAlaGlyIyAlaAlaHisSerGluAlaLeuPheIleA
                             FRT>
attaacccctcactaaagggcggccgcgaagttcctattctctagaaagtatagggaactcctcgagcgctataggtagtcgatggtgatgctgcagggtatgc
GCAAGCCGGTTAACGACCTGTCCCGTGGCCGCACTGGTTGACGATATCGTCTACACCATCCGCTGACTGCGATTCAGTCTGCACAGCAGCAGTAAtc
       <P395-ackA-pta-check5                            <P395-ackA-pta-check6
tcgtcatcatccgcagctttgcgctgcgatatctgaaccggaataatcactatttccggtttttattctcttaatctgcattatcctttctgattatcttgctta
actgcgctcatgatgaattgcgccattcacttgcatactactccactttgttttgtgcaaggaatattgcctatgtccgcaatcactgaatcaaccaacaa
       yfcC>
gaagatggcaATGCCCGATACCGTTGGTGCGATTATCTTTTTGTTGCTATTTTAACCTTGCCCACCT
```

```
P395-adhE-check1>
CAGGTTGGCTCTAAGGTTAGTGTTTTGTTTCCGCCGCTGCGCTGTCTGATAACTGGTCATGCTGATAAAGACGGGAATAATCCCTACC
                                                                            <ychE
GGGTTGACCAGCCAAATAACCCGAAGAAAAAATTTGAGTAACTGGGAAAAATCAAAAAAGCTCGAATCACggttagctccgaagca
aaagccggataatgttagccataaataaggttgaaaagacgcgctgacaatacgcctttgacagcattttcacctcctaactactta aaattg
ctatcattcgttattgttatctagttgtgtgcaaaacatgctaatgtagctccaccaaatcatactacaatttattaactgtagctataatgggcaaa P395-adhE-check2>
agcgatgctgaaaggtgtcagtttgcaaaaatttgatttggatcactgctaatcagtaccagaagtgagtaatcttgttacgccacctggaagt
gacgcattagagataataactctaatgtttaaactctttagtaaatcacagtgagtgtgagcgcgataagctttgattttcataggttaagc
                                                                                          adhE>
aaatcatcaccgcactgactactctcgtattcgagcagatgattactaaaaagtttaacattatcaggagagca ATGGCTGTTACTAA
                                                                       ▶MetAlaValThrAs FRT>
TGTCCTGAACTTAACGCACTCGTAGAGCGTGTAAAaattaaccctcactaaagggcggaagtcctattctctagaaagtataggaactt
nValAlaGluLeuAsnAlaLeuValGluValGlyValArgValLysIleLeuArg                            P395-adhE-check5>
cgagcgtaatgaactccgtgctAAGAAGCCGCTCCGGCTAAAGCTGAGAAAAAAGCGAAAAAATCCGCTTAAtcagtagcgctgtct
ggcaatataaacgcggcccccttctgggcgttttttgttaccccaaagcaactttttccataaacgacagcattagcctatcatatttgcac
gatgtataacgcctaaacacaggatattgtactttacaggtcacaagtcggtgcttaagagccctgtgaggcgtatagcggcgttaaa
aaactgccgagaagggtatatagcccggaagaagtgcgtaaaacgaactgacaggataaaagtgcccgctcaccctgtcagtaaagaattctt
                                                                    P395-adhE-check6>
attaATCGTGCGATGCCTTTCCTGAATAGCCGTTAATGAGCCGACTTGTAACGCCCTCTATATAGTGT
```

[Figure showing DNA/protein sequence alignment with labeled regions including p395-frd-check1, poxA, frdA, FRT, ampC, and p395-frd-check4]

TAATCCCGGACTTCGCATCGCCCGAATTCTGGAACCCGCCGTCGGTTCGCACCCGGAAAATTTTTCTCACCTGACCGGTGATGAACTTCATCACTGATAACC

<P395-pflB-check2>

<P395-pflB-check1>

TGATTCCGGGTTACGATCGGTAATATTATCGGGCGGTGGTTTGTTGGGTTTGTTGGTTGACATACTGGGTCATTTACCTGGTGAAAACGATCACCATTAAtggt pflB> ATGTCCGAGCTTAATGAAAAGTTAGCCACAGCCTGGGAAGGTTTTACCAAaatta
  MetSerGluLeuAsnGluLysLeuAlaThrAlaTrpGluGlyPheThrLysIleA tgtcgaagtacgcagtaataaaaatccacttaagaaggtaggtgtt accctcactaaggcggaagttcctattctctagaaatatagaactcgagcccttaatgaactccgtgctaAAGAACAGCAGGACGTTATTACTCGTACCT
snProHis                                                                                   pflA>

TCACTCAAATCTATGTAAttagatttgactgaaatcgtacagtaaaaagctccacgaagtgggcctttttagcacgagagccttttttgtcagc tatctatacttaaggtgactgccaaacagactgccgagctgccgcaccacggcctcagatgggcacatctggagaaacaccgcatgcctgatgccgctgagc
                    <P395-pflB-check3

TGCTCCCATTCACTCCCTTTGAATCCTCGGAACCGTACCGGCCAAGGCTAGTACACCGGTATTCAGTTTATCACCTTTATCAGGCTGCCGAATGCCGCTGCCTGATATC
                                              <P395-pflB-check4

TCAATAACCCGCACACCTGGCGGAATACGCATGGC

Figure 5 (continued)
B)

```
GAG GGT TTT TGG AGC AGC TGG CGA TTG CTC CGT CTG CGG CAA TTT CGC CAG ACA AGC AGA ATC AAG
    P395-ldhA-check1>
TTC TAC CGT GCC GAC GTT CAA TAA CCA GCG GCT GGG ATG TGA AAG GCT GGC GTT GGT GAT ATG CGC
                                                                P395-ldhA-check3>
AAG CTG ACA ATC TCC CAC CAG ATA ACG GAG ATC GGG AAT GAT GAA ACC TTT ACG CGT AAT GCG TGG
GCT TTC ATC TAA TGC AAT ACG TGT CCC GAG CGG TAG CCA GAT GCC CGC CAG CGT GGG AAC CCA CAG
CCC GAG CGT CAT CAG CAG CGT CAA CGG CAC AAG AAT AAT CAG TAA TAA CAG CGC GAG AAC GGC TTT
                <ydhE
ATA TTT ACC CAG CAT gggtagttaatatcctgatttagcgaaaaattaagcattcaatacgggtattgtggcatgtttaacgttcagttgaa
ggttgcgcctacactaagcatagttgttgatgaattttcaatatcgccatagctttcaattatatttgaaattttgtaaaatattttagtagcttaaa
        alaD gstaar>
tgtgattcaacatcactggagaaagtctt atg aaa att ggc atc cct aaa gag att aag aac aat gaa aac cgt
                             ▶  M   K   I   G   I   P   K   E   I   K   N   N   E   N   R
gta gca atc acc ccg gca ggt gtt atg act ctg gtt aaa gcg ggc cac gat gtg tac gtc gaa acc
▶  V   A   I   T   P   A   G   V   M   T   L   V   K   A   G   H   D   V   Y   V   E   T
gaa gcg ggt gcc ggc agc ggc ttc agc gac agc gag tat gag aag gcg ggt gcg gtt att gtg act
▶  E   A   G   A   G   S   G   F   S   D   S   E   Y   E   K   A   G   A   V   I   V   T
aag gcg gag gac gct tgg gca gcc gaa atg gtt ctg aag gtg aaa gaa ccg ctg gcg gag gag ttt
▶  K   A   E   D   A   W   A   A   E   M   V   L   K   V   K   E   P   L   A   E   E   F
cgc tat ttt cgt ccg ggt ctg att ttg ttc acc tac ctg cac ctg gct gcg gcc gag gcg ctg acc
▶  R   Y   F   R   P   G   L   I   L   F   T   Y   L   H   L   A   A   A   E   A   L   T
aag gcg ctg gtg gag cag aag gtt gtt ggc atc gcg tac gaa gtt caa gcg aat ggt tcc
▶  K   A   L   V   E   Q   K   V   V   G   I   A   Y   E   T   V   Q   L   A   N   G   S
ctg ccg ctg ctg acc cct atg tct gaa gtt gcg ggt cgt atg agt gtt caa gtc ggc gct cag ttt
▶  L   P   L   L   T   P   M   S   E   V   A   G   R   M   S   V   Q   V   G   A   Q   F
ctg gag aaa ccg cac ggt ggc aag ggc att ttg ctg ggt gtt ccg ggt gtc cgc cgt ggt aaa
▶  L   E   K   P   H   G   G   K   G   I   L   L   G   V   P   G   V   R   G   K
gtg acg atc att ggc ggt ggt acg gcc ggt acg aac gcg gcc aag att gcc gta ggt ctg ggt gca
▶  V   T   I   I   G   G   G   T   A   G   T   N   A   A   K   I   A   V   G   L   G   A
gat gtg acc att ctg gac atc aac gcg gaa cgt ttg cgt gag ctg gac gat ctg ttt ggc gac caa
▶  D   V   T   I   L   D   I   N   A   E   R   L   R   E   L   D   D   L   F   G   D   Q
gtc acc acc ctg atg agc aac agc tac cac atc gcg gag tgc gtc cgt gaa agc gat ttg gtc gtt
▶  V   T   T   L   M   S   N   S   Y   H   I   A   E   C   V   R   E   S   D   L   V   V
ggt gcg gtg ctg atc ccg gga gca aag gcg ccg aaa ctg gtg acg gag atg gtc cgt agc atg
▶  G   A   V   L   I   P   G   A   K   A   P   K   L   V   T   E   E   M   V   R   S   M
acc ccg ggt tcg gtt ctg gtc gac gtg gcc att gac cag ggc ggt atc ttc gaa acc acc gac agc
▶  T   P   G   S   V   L   V   D   V   A   I   D   Q   G   G   I   F   E   T   T   D   R
gtc acg acc cat gat gac ccg acc tat gtg aaa cat ggc gtg gtt cac tat gcg gtc gcg aat atg
▶  V   T   T   H   D   D   P   T   Y   V   K   H   G   V   V   H   Y   A   V   A   N   M
ccg ggt gca gtg ccg cgc acg tcc acg ttc gcg ctg acg aac gtg acg att cca tac gct ctg cag
▶  P   G   A   V   P   R   T   S   T   F   A   L   T   N   V   T   I   P   Y   A   L   Q
atc gcc aat aag ggc tat cgt gcg gcg tgt ctg gat aat ccg gca ttg ctg aaa ggc atc aat acc
▶  I   A   N   K   G   Y   R   A   A   C   L   D   N   P   A   L   L   K   G   I   N   T
ctg gat ggt cat atc gtt tac gag gct gtg gct gca gca cac aac atg ccg tac act gat gtc cat
▶  L   D   G   H   I   V   Y   E   A   V   A   A   A   H   N   M   P   Y   T   D   V   H
                                                                    FRT>
agc ttg ctg caa ggc taa aattaaccctcactaaagggcggaagttcctatcctagaaagtataggaacttcgagccctaatgaactcc
▶  S   L   L   Q   G
gtgctatcttgccgctcccctgcattccaggggagctgattcagataatccccaatgaccttcatcctctattcttaaaatagccctgagtcagaaact
            halJ gene>                                       <P395-ldhA-check2
gtaattgagaaccaca ATG AAG AAA GTA GCC GCG CTC GTT GCG CTA AGC CTG CTG ATG GCG GGA TGT GTA
AGT AAT GAC AAA ATT GCT GTA ACG CCA GAA CAG TTA CAG CAT CAT CGT TTT GTG CTG GAA AGC GTA
        <P395-ldhA-check4
AAC CGT AAG CCC GTG ACC AAC GAT AAA AAT CCG CCA GAA ATC
```

Figure 7

```
Ex1    GCGGCATAGT AAATTCCCCC ACCAGTTTAA CCGGCGGCTG ATTTTCAAAC
Ev2    GCGGCATAGT AAATTCCCCC ACCAGTTTAA CCGGCGGCTG ATTTTCAAAC
Ev3    GCGGCATAGT AAATTCCCCC ACCAGTTTAA CCGGCGGCTG ATTTTCAAAC

Ex1    GCGACGACAT CCAGTTCGCT GACTGTAAGT TGTTGCCCTT TCAGCTGGCC
Ev2    GCGACGACAT CCAGTTCGCT GACTGTAAGT TGTTGCCCTT TCAGCTGGCC
Ev3    GCGACGACAT CCAGTTCGCT GACTGTAAGT TGTTGCCCTT TCAGCTGGCC

Ex1    TTGAAATTTA ACTTTTTCGC CCTGATAACG CAGTTGCTGG ATATCAGAGG
Ev2    TTGAAATTTA ACTTTTTCGC CCTGATAACG CAGTTGCTGG ATATCAGAGG
Ev3    TTGAAATTTA ACTTTTTCGC CCTGATAACG CAGTTGCTGG ATATCAGAGG

Ex1    TTAATGCGAG AGAGAGTTTT CCCTGCCATT CCTGCCAGGG AGAAAAAATC
Ev2    TTAATGCGAG AGAGAGTTTT CCCTGCCATT CCTGCCAGGG AGAAAAAATC
Ev3    TTAATGCGAG AGAGAGTTTT CCCTGCCATT CCTGCCAGGG AGAAAAAATC

Ex1    AGTTTATCGA TATTGATCCA GGTGTTAGGC AGCATGGACT GCCACTGCGC
Ev2    AGTTTATCGA TATTGATCCA GGTGTTAGGC AGCATGGACT GCCACTGCGC
Ev3    AGTTTATCGA TATTG..... .......... .......... ..........
                           Begin Deletion in Ev3

Ex1    GAGGGTTTTT GGAGCAGCTG GCGATTGCTC CGTCTGCGGC AATTTCGCCA
Ev2    GAGGGTTTTT GGAGCAGCTG GCGATTGCTC CGTCTGCGGC AATTTCGCCA
Ev3    .......... .......... .......... .......... ..........

Ex1    GACAAGCAGA ATCAAGTTCT ACCGTGCCGA CGTTCAATAA CCAGCGGCTG
Ev2    GACAAGCAGA ATCAAGTTCT ACCGTGCCGA CGTTCAATAA CCAGCGGCTG
Ev3    .......... .......... .......... .......... ..........

Ex1    GGATGTGAAA GGCTGGCGTT GGTGATATGC GCAAGCTGAC AATCTCCCAC
Ev2    GGATGTGAAA GGCTGGCGTT GGTGATATGC GCAAGCTGAC AATCTCCCAC
Ev3    .......... .......... .......... .......... ..........

Ex1    CAGATAACGG AGATCGGGAA TGATTAAACC TTTACGCGTA ATGCGTGGGC
Ev2    CAGATAACGG AGATCGGGAA TGATTAAACC TTTACGCGTA ATGCGTGGGC
Ev3    .......... .......... .......... .......... ..........

Ex1    TTTCATCTAA TGCAATACGT GTCCCGAGCG GTAGCCAGAT GCCCGCCAGC
Ev2    TTTCATCTAA TGCAATACGT GTCCCGAGCG GTAGCCAGAT GCCCGCCAGC
Ev3    .......... .......... .......... .......... ..........

Ex1    GTGGGAACCC ACAGCCCGAG CGTCATCAGC AGCGTCAACG GCACAAGAAT
Ev2    GTGGGAACCC ACAGCCCGAG CGTCATCAGC AGCGTCAACG GCACAAGAAT
Ev3    .......... .......... .......... .......... ..........

Ex1    AATCAGTAAT AACAGCGCGA GAACGGCTTT ATATTTACCC AGCATGGGTA
Ev2    AATCAGTAAT AACAGCGCGA GAACGGCTTT ATATTTACCC AGCATGGGTA
                                                    Begin ydbH
Ev3    .......... .......... .......... .......... ..........
```

Figure 7 (continued)

```
Ex1    GTTAATATCC TGATTTAGCG AAAAATTAAG CATTCAATAC GGGTATTGTG
Ev2    GTTAATATCC TGATTTAGCG AAAAATTAAG CATTCAATAC GGGTATTGTG
Ev3    .......... .......... .......... .......... ..........

Ex1    GCATGTTTAA CCGTTCAGTT GAAGGTTGCG CCTACACTAA GCATAGTTGT
Ev2    GCATGTTTAA CCGTTCAGTT GAAGGTTGCG CCTACACTAA GCATAGTTGT
Ev3    .......... .......... .......... .......... ..........

Ex1    TGATGAATTT TTCAATATCG CCATAGCTTT CAATTATATT TGAAATTTTG
Ev2    TGATGAATTT TTCAATATCG CCATAGCTTT CAATTATATT TGAAATTTTG
Ev3    .......... .......... .......... .......... ....ATTTTG
                                                End Deletion in Ev3

Ex1    TAAAATATTT TTAGTAGCTT AAATGTGATT CAACATCACT GGAGAAAGTC
Ev2    TAAAATATTT TTAGTAGCTT AAATGTGATT CAACATCACT GGAGAAAGTC
Ev3    TAAAATATTT TTAGTAGCTT AAATGTGATT CAACATCACT GGAGAAAGTC

Ex1    TTATGAAACT CGCCGTTTAT AGCACAAAAC AGTACG.ACA AGAAGTACC.
           Begin ldhA
Ev2    TTATGAAAAT TGGCATCCCT A....AAGAG ATTAAGAACA ATGAAAACCG
           Begin alaD
Ev3    TTATGAAAAT TGGCATCCCT A....AAGAG ATTAAGAACA ATGAAAACCG
```

RECOMBINANT MICROORGANISM FOR IMPROVED PRODUCTION OF FINE CHEMICALS

This application is a National Stage application of International No. PCT/IB2014/064426, filed Sep. 11, 2014, which claims the benefit of U.S. Provisional Application Nos. 61/881,968, filed Sep. 25, 2013, 61/881,969, filed Sep. 25, 2013, 61/881,975 filed Sep. 25, 2013, and 61/881,972, filed Sep. 25, 2013; the entire contents of which are hereby incorporated herein by reference in their entirety.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "75982_SubSeqlisting.txt" created on Jun. 27, 2016, and is 113,867 bytes in size. The sequence listing contained in this .txt file is part of the specification and is hereby incorporated by reference herein in its entirety.

FIELD OF THE INVENTION

The present invention relates to a recombinant nucleic acid molecule, a recombinant microorganism, to a method for producing alanine, pyruvate, succinate, aspartate, malate, lactate, valine and/or leucine and to the use of the recombinant nucleic acid molecule or the recombinant microorganism for the fermentative production of alanine, pyruvate, succinate, aspartate, malate, lactate, valine and/or leucine.

DESCRIPTION OF THE INVENTION

Amino acids are organic compounds with a carboxy-group and an amino-group. The most important amino acids are the alpha-amino acids where the amino group is located next to the carboxy-group. Proteins are based on alpha-amino acids.

Alanine has drawn considerable interest because it has been used as an additive in the food, feed and pharmaceutical industries. Moreover alanine is a raw material for the industrial production of alanine, N,N-bis(carboxymethyl)-, trisodium salt (MGDA, trade name Trilon M) which is a strong chelating agent, showing an excellent performance at dissolving organic and inorganic scale (WO94/29421, WO2012/150155). Trilon M grades are readily biodegradable according to standard OECD tests. Due to the superb ecological and toxicological profile, Trilon M grades are particularly suitable for use in products for end-consumers and the demand for such biodegradable complex builders is constantly rising.

Alanine can be produced by fermentation with Coryneform bacteria (Hermann, 2003: Industrial production of amino acids by Coryneform bacteria, J. of Biotechnol, 104, 155-172) or *E. coli*. (WO2007/120198, WO2008/119009).

*E. coli* has recently been described that overexpression of the ygaW gene improves fermentative alanine productivity of a microorganism (WO2012/172822).

Alanine production in *E. coli* is more efficient and widely used for industrial production of alanine as raw material for the chemical industry. As the demand of the chemical industry for alanine is increasing, there is a demand for improvement of productivity of fermentative production of alanine.

It is one object of the present invention to provide microorganisms which can be used in fermentative production of alanine with high yield and efficiency.

DETAILED DESCRIPTION OF THE INVENTION

A contribution to achieving the above mentioned aim is provided by a recombinant microorganism of the family of *Escherichia coli* (*E. coli*) having, compared to a respective reference microorganism at least one of i) an introduced, increased or enhanced activity and/or expression of a lpd gene, and/or ii) an introduced, increased, enhanced or altered activity and/or expression of a zipA gene and/or iii) a ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene.

The term "higher", "increase" or "enhanced" e.g. in reference to expression and/or activity of an enzyme or to yield or productivity, means a significantly higher, increased or enhanced expression and/or activity or yield or productivity.

The term "reduced, repressed or deleted expression and/or activity of an enzyme", means a significantly reduced, repressed or deleted expression and/or activity and also encompasses an undetectable expression and/or activity of the respective enzymes.

The term "altered" expression and/or activity of an enzyme means an expression and/or activity of an enzyme in a recombinant microorganism that is significantly different from the expression and/or activity of the respective enzyme in a wild-type, non-recombinant microorganism.

Surprisingly, it has been discovered that a microorganism having at least one of i) an introduced, increased or enhanced activity and/or expression of a protein encoded by the lpd gene and/or ii) an introduced, increased, enhanced or altered activity and/or expression of a protein encoded by the zipA gene and or iii) a ygaW gene comprising a mutation at position 13-15 of SEQ ID NO: 1 or at a corresponding position of a homolog or functional equivalent thereof has a higher yield and/or productivity of alanine in fermentative production when compared to the same microorganism not comprising an introduced, increased or enhanced activity and/or expression of the respective lpd gene and/or an introduced, increased, enhanced or altered activity and/or expression of the respective zipA gene and/or a ygaW gene not comprising the respective mutation.

Accordingly, one embodiment of the invention at hand is a recombinant microorganism comprising compared to a respective reference microorganism at least one of i) an introduced, increased or enhanced activity and/or expression of a lpd gene encoding a lipoamide dehydrogenase protein and/or ii) an introduced, increased, enhanced or altered activity and/or expression of a zipA gene encoding a cell division protein involved in Z ring assembly and/or iii) a ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene and having compared to a respective reference microorganism a higher yield and/or productivity of alanine in fermentative production.

In one embodiment of the invention at hand the recombinant microorganism comprising compared to a respective reference microorganism at least one of i) an introduced, increased or enhanced activity and/or expression of a lpd gene encoding a lipoamide dehydrogenase protein and/or ii) an introduced, increased, enhanced or altered activity and/or expression of a zipA gene encoding a cell division protein involved in Z ring assembly and/or iii) a ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene and having compared to a respective reference microorganism a higher yield and/or productivity of alanine in fermentative production is further comprising the deleted and introduced enzyme activities as described in WO2007/120198 and WO2008/119009 which are incorporated by reference.

The term "reference microorganism" as used herein means a control microorganism to which the recombinant microorganism is compared. This reference microorganism has substantially the same genotype as the recombinant microorganism with the exception of the difference to be analyzed. Preferably the reference microorganism is the strain from which the recombinant microorganism is originated. For example, a gene has been introduced into a wild type microorganism, thus creating a recombinant microorganism, in this case the wild type would be a suitable reference microorganism for this recombinant microorganism. It is also possible, that into a recombinant microorganism A a further mutation is introduced, thereby creating a recombinant microorganism B. The recombinant microorganism A would then be the suitable reference microorganism for recombinant microorganism B. In the event, the performance of a recombinant microorganism and the respective reference microorganism shall be compared both microorganisms are grown under substantially identical conditions.

It is obvious for the skilled person that a microorganism having an increased yield and/or productivity of alanine can also be used for the production of other metabolites that are closely related to alanine, for example metabolites that are intermediates in the alanine pathway, that share common intermediates with the alanine pathway or that are metabolites which use alanine as intermediate in their pathway. The microorganisms of the invention can also be easily adapted for having an increased yield and/or productivity of such related metabolites by increasing or introducing certain enzyme activities or by knocking out or decreasing certain enzyme activities.

Such metabolites are for example pyruvate, succinate, aspartate, malate, lactate, valine and leucine.

For example, in order to use the recombinant microorganism of the invention to produce succinate, the genes ldh, pfl, pta and adhE have to be knocked out and a PEP carboxylase gene and/or a pyruvate carboxylase gene have to be introduced in the genome of the microorganism of the invention. The respective pathway and necessary mutations are described for example in Zhang et al. (2009), PNAS (106) pp 20180-20185.

Accordingly, another embodiment of the invention at hand is a recombinant microorganism comprising compared to a respective reference microorganism at least one of i) an introduced, increased or enhanced activity and/or expression of a lpd gene encoding a lipoamide dehydrogenase protein, and/or ii) an introduced, increased, enhanced or altered activity and/or expression of a zipA gene encoding a cell division protein involved in Z ring assembly and/or iii) a ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene and having compared to a respective reference microorganism a higher yield and/or productivity of pyruvate, succinate, aspartate, malate, lactate, valine and/or leucine in fermentative production.

In some embodiments, the microorganism is a prokaryotic cell. Suitable prokaryotic cells include Gram-positive, Gram negative and Gram-variable bacterial cells, preferably Gram-negative.

Thus, microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscule, L. lagerheimii, Phormidium tenue, Anabaena* sp., *Leptolyngbya* sp and so forth.

In some embodiments, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces*

*pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia*.

Numerous bacterial industrial strains are especially suitable for use in the methods disclosed herein. In some embodiments, the microorganism is a species of the genus *Corynebacterium*, e.g. *C. acetophilum, C. glutamicum, C. callunae, C. acetoacidophilum, C. acetoglutamicum*. In some embodiments, the microorganism is a species of the genus *Bacillus*, e.g., *B. thuringiensis, B. anthracis, B. megaterium, B. subtilis, B. lentils, B. circulans, B. pumilus, B. lautus, B. coagulans, B. brevis, B. firmus, B. alkaophius, B. licheniformis, B. clausii, B. stearothermophilus, B. halodurans, B. subtilis, B. pumilus*, and *B. amyloliquefaciens*. In some embodiments, the microorganism is a species of the genus *Erwinia*, e.g., *E. uredovora, E. carotovora, E. ananas, E. herbicola, E. punctata* and *E. terreus*. In some embodiments, the microorganism is a species of the genus *Escherichia*, e.g., *E. coli*. In other embodiments the microorganism is a species of the genus *Pantoea*, e.g., *P. citrea* or *P. agglomerans*. In still other embodiments, the microorganism is a species of the genus *Streptomyces*, e.g., *S. ambofaciens, S. achromogenes, S. avermitilis, S. coelicolor, S. aureofaciens, S. aureus, S. fungicidicus, S. griseus* or *S. lividans*. In further embodiments, the microorganism is a species of the genus *Zymomonas*, e.g., *Z. mobilis* or *Z. lipolytica*. In further embodiments, the microorganism is a species of the genus *Rhodococcus*, e.g. *R opacus*.

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

In addition to the introduced, increased or enhanced activity and/or expression of a lpd gene encoding a lipoamide dehydrogenase protein and/or the introduced, increased, enhanced or altered activity and/or expression of a zipA gene encoding a cell division protein involved in Z ring assembly and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene, the recombinant microorganism of the invention may further comprise (a) a reduced, repressed or deleted activity and/or expression of a pflB gene encoding a pyruvate formate lyase I, wherein the reduction, repression or deletion of the activity and/or expression of the pflB gene is determined compared to a respective reference microorganism.

In addition to the introduced, increased or enhanced activity and/or expression of a lpd gene encoding a lipoamide dehydrogenase protein, and/or the introduced, increased, enhanced or altered activity and/or expression of a zipA gene encoding a cell division protein involved in Z ring assembly and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene, the recombinant microorganism of the invention may further comprise (b) a reduced, repressed or deleted activity and/or expression of a adhE gene encoding a bifunctional acetaldehyde-CoA dehydrogenase/iron-dependent alcohol dehydrogenase/pyruvate-formate lyase deactivase), wherein the reduction, repression or deletion of the activity and/or expression of the adhE gene is determined compared to a respective reference microorganism.

In addition to the introduced, increased or enhanced activity and/or expression of a lpd gene encoding a lipoamide dehydrogenase protein, and/or the introduced, increased, enhanced or altered activity and/or expression of a zipA gene encoding a cell division protein involved in Z ring assembly and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene, the recombinant microorganism of the invention may further comprise (c) a reduced, repressed or deleted activity and/or expression of a ldhA gene encoding a NAD-dependent fermentative D-lactate dehydrogenase, wherein the reduction, repression or deletion of the activity and/or expression of the ldhA gene is determined compared to a respective reference microorganism.

In addition to the introduced, increased or enhanced activity and/or expression of a lpd gene encoding a lipoamide dehydrogenase protein, and/or the introduced, increased, enhanced or altered activity and/or expression of a zipA gene encoding a cell division protein involved in Z ring assembly and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene, the recombinant microorganism of the invention may further comprise (d) a reduced, repressed or deleted activity and/or expression of a pta gene encoding a phosphate acetyltransferase, wherein the reduction, repression or deletion of the activity and/or expression of the pta gene is determined compared to a respective reference microorganism.

In addition to the introduced, increased or enhanced activity and/or expression of a lpd gene encoding a lipoamide dehydrogenase protein, and/or the introduced, increased, enhanced or altered activity and/or expression of a zipA gene encoding a cell division protein involved in Z ring assembly and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene, the recombinant microorganism of the invention may further comprise (e) a reduced, repressed or deleted activity and/or expression of a frdA gene encoding a fumarate reductase, wherein the reduction, repression or deletion of the activity and/or expression of the frdA gene is determined compared to a respective reference microorganism.

In addition to the introduced, increased or enhanced activity and/or expression of a lpd gene encoding a lipoamide dehydrogenase protein, and/or the introduced, increased, enhanced or altered activity and/or expression of a zipA gene encoding a cell division protein involved in Z ring assembly and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene, the recombinant microorganism of the invention may further comprise (f) an introduced, increased or enhanced activity and/or expression of an alaD gene encoding an alanine dehydrogenase, wherein the increase or enhancement of the activity and/or expression of the alaD gene is determined compared to a respective reference microorganism.

Preferably, the recombinant microorganism of the invention comprising the introduced, increased or enhanced activity and/or expression of a lpd gene encoding a lipoamide dehydrogenase protein, and/or the introduced, increased, enhanced or altered activity and/or expression of a zipA gene encoding a cell division protein involved in Z ring assembly and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene is additionally having at least two, more preferably at least three, even more preferably at least four, even more preferably at least five, most preferably all of the features selected from the group of (a) a reduced, repressed or deleted activity and/or expression of a pflB gene encoding a pyruvate formate lyase I and (b) a reduced, repressed or deleted activity and/or expression of a adhE gene encoding a bifunctional acetaldehyde-CoA dehydrogenase/iron-dependent alcohol dehydrogenase/pyruvate-formate lyase deactivase) and (c) a reduced, repressed or deleted activity and/or expression of a ldhA gene encoding a NAD-dependent fermentative D-lactate dehydrogenase and (d) a reduced, repressed or deleted activity and/or expression of a pta gene encoding a phosphate acetyltransferase and (e) a reduced, repressed or deleted activity and/or expression of a frdA gene encoding a fumarate reductase and (f) an introduced, increased or enhanced activity and/or expression of an alaD gene encoding an alanine dehydrogenase, wherein the reduction, repression, deletion, increase or enhancement of the activity and/or expression of a gene is determined compared to a respective reference microorganism.

The alaD gene may be derived from any organism or may be a synthetic gene designed by man, for example having codon usage optimized for expression in the recombinant microorganism of the invention or being optimized for enzyme activity, e.g. having improved Vmax or Km. Preferably the alaD gene is derived from a microorganism of one of the geni *Bacillus, Geobacillus, Paenibacillus, Halobacillus, Brevibacillus*. In a more preferred embodiment the alaD gene is derived from a microorganism of the genus *Geobacillus*. In a most preferred embodiment, the alaD gene is derived from *Geobacillus stearothermophilus*.

In a preferred embodiment the alaD gene has been codon optimized for the expression in the recombinant microorganism of the invention.

The microorganism of the invention may comprise further genetic modifications, such as mutations, knock-outs or enhanced or introduced enzyme activities that further improve yield and/or productivity of alanine, pyruvate, succinate, aspartate, malate, lactate, valine and/or leucine, preferably succinate or alanine, more preferably alanine.

In a further embodiment the lpd gene encoding a lipoamide dehydrogenase protein with a introduced, increased or enhanced activity and/or expression in the recombinant microorganism of the invention, is selected from the group of (i) a nucleic acid molecule comprising a sequence of SEQ ID NO: 49, or (ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 49, or (iii) a nucleic acid molecule hybridizing to a nucleic acid molecule having SEQ ID NO: 49 under medium stringent conditions, more preferably under high stringent conditions, most preferably under very high stringent conditions, or (iv) a nucleic acid molecule encoding a polypeptide of SEQ ID NO: 50, or (v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 50, wherein the polypeptide encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 50.

In one example, the lpd gene encoding a lipoamide dehydrogenase protein with a introduced, increased or enhanced activity and/or expression in the recombinant microorganism of the invention, is having the sequence of SEQ ID NO: 51, encoding the protein having SEQ ID NO: 52.

In a further embodiment the zipA gene encoding a cell division protein involved in Z ring assembly with a introduced, increased, enhanced or altered activity and/or expression in the recombinant microorganism of the invention, is selected from the group of (i) a nucleic acid molecule comprising a sequence of SEQ ID NO: 45, or (ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 45, or (iii) a nucleic acid molecule hybridizing to a nucleic acid molecule having SEQ ID NO: 45 under medium stringent conditions, more preferably under high stringent conditions, most preferably under very high stringent conditions, or (iv) a nucleic acid molecule encoding a polypeptide of SEQ ID NO: 46, or (v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 46, wherein the polypeptide encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 46.

In one example, the zipA gene encoding a cell division protein involved in Z ring assembly with a introduced, increased, enhanced or altered activity and/or expression in the recombinant microorganism of the invention, is having the sequence of SEQ ID NO: 47, encoding the protein having SEQ ID NO: 48.

In a further embodiment the ygaW gene encoding an alanine transporter with an altered activity and/or expression in the recombinant microorganism of the invention, is selected from the group of (i) a nucleic acid molecule comprising a sequence of SEQ ID NO: 1, or
(ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, or
(iii) a nucleic acid molecule hybridizing to a nucleic acid molecule having SEQ ID NO: 1 under medium stringent conditions, more preferably under high stringent conditions, most preferably under very high stringent conditions, or
(iv) a nucleic acid molecule encoding a polypeptide of SEQ ID NO: 2, or
(v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 2, and wherein the codon of the genes under (i) to (v) corresponding to position 13-15 of SEQ ID NO: 1 is not encoding amino acid glutamine and is not a stop codon or the amino acid of the proteins encoded by the genes under (i) to (v) corresponding to position 5 of SEQ ID NO: 2 is not glutamine, and wherein the protein encoded by the gene as defined above in (1) to (5) has an altered activity and/or expression compared to the protein having SEQ ID NO: 2, and wherein the microorganism comprising the mutated gene and/or protein as defined above has an improved alanine yield in fermentation.

In one example, the ygaW gene encoding an alanine transporter with an altered activity and/or expression in the recombinant microorganism of the invention is having the sequence of SEQ ID NO: 3, 56, 58 or 60, encoding the protein having SEQ ID NO: 4, 57, 59 or 61.

The recombinant microorganism of the invention comprising the introduced, increased or enhanced expression and/or activity of the lpd gene encoding a lipoamide dehydrogenase protein, and/or the introduced, increased, enhanced or altered activity and/or expression of a zipA gene and/or the ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene may further comprise any one, two, three, four, five or all of the features as defined above under (a) to (f), wherein the pflB gene is selected from the group consisting of (A) a nucleic acid molecule comprising a sequence of SEQ ID NO: 5, or
(B) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 5, or
(C) a nucleic acid molecule hybridizing to a nucleic acid molecule having SEQ ID NO: 5 under medium stringent conditions, more preferably under high stringent conditions, most preferably under very high stringent conditions, or
(D) a nucleic acid molecule encoding a polypeptide of SEQ ID NO: 6, or
(E) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 6, wherein the polypeptide encoded by (B), (C) or (E) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 6 and wherein the adhE gene is selected from the group consisting of (F) a nucleic acid molecule comprising a sequence of SEQ ID NO: 7, or
(G) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 7, or
(H) a nucleic acid molecule hybridizing to a nucleic acid molecule having SEQ ID NO: 7 under medium stringent conditions, more preferably under high stringent conditions, most preferably under very high stringent conditions, or
(I) a nucleic acid molecule encoding a polypeptide of SEQ ID NO: 8, or
(J) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 8, wherein the polypeptide encoded by (G), (H) or (J) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 8 and wherein the ldhA gene is selected from the group consisting of (K) a nucleic acid molecule comprising a sequence of SEQ ID NO: 9, or
(L) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 9, or
(M) a nucleic acid molecule hybridizing to a nucleic acid molecule having SEQ ID NO: 9 under medium stringent conditions, more preferably under high stringent conditions, most preferably under very high stringent conditions, or
(N) a nucleic acid molecule encoding a polypeptide of SEQ ID NO: 10, or
(O) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 10,
wherein the polypeptide encoded by (L), (M) or (O) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 10 and wherein the pta gene is selected from the group consisting of
(P) a nucleic acid molecule comprising a sequence of SEQ ID NO: 11, or
(Q) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 11, or
(R) a nucleic acid molecule hybridizing to a nucleic acid molecule having SEQ ID NO: 11 under medium stringent conditions, more preferably under high stringent conditions, most preferably under very high stringent conditions, or
(S) a nucleic acid molecule encoding a polypeptide of SEQ ID NO: 12, or
(T) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 12,
wherein the polypeptide encoded by (Q), (R) or (T) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 12 and wherein the frdA gene is selected from the group consisting of
(U) a nucleic acid molecule comprising a sequence of SEQ ID NO: 13, or
(V) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 13, or
(W) a nucleic acid molecule hybridizing to a nucleic acid molecule having SEQ ID NO: 13 under medium stringent conditions, more preferably under high stringent conditions, most preferably under very high stringent conditions, or
(X) a nucleic acid molecule encoding a polypeptide of SEQ ID NO: 14, or
(Y) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 14,
wherein the polypeptide encoded by (V), (W) or (Y) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 14 and wherein the alaD gene is selected from the group consisting of
(Z) a nucleic acid molecule comprising a sequence of SEQ ID NO: 15, or
(AA) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 15, or
(BB) a nucleic acid molecule hybridizing to a nucleic acid molecule having SEQ ID NO: 15 under medium stringent conditions, more preferably under high stringent conditions, most preferably under very high stringent conditions, or
(CC) a nucleic acid molecule encoding a polypeptide of SEQ ID NO: 16, or
(DD) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 16,
wherein the polypeptide encoded by (AA), (BB) or (DD) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 16.

Preferably, the nucleic acid molecule as defined in (Z) to (DD) is under control of a sequence functioning as a promoter in a microorganism having the sequence of
(1) a nucleic acid molecule comprising a sequence of SEQ ID NO: 54 or 55, or
(2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 54 or 55, or
(3) a nucleic acid molecule hybridizing to a nucleic acid molecule having SEQ ID NO: 54 or 55 under medium stringent conditions, more preferably under high stringent conditions, most preferably under very high stringent conditions or
(4) a fragment of at least 10 nucleotides, preferably at least 20 nucleotides, at least 30 nucleotides or at least 40 nucleotides, more preferably a fragment of at least 50 nucleotides, at least 75 nucleotides or at least 100 nucleotides, even more preferably at least 150 or at least 200 nucleotides of the nucleic acid molecule having SEQ ID NO: 54 or 55. Preferably the fragment of SEQ ID NO: 54 or 55 is a fragment comprising the 3' region of SEQ ID NO: 54 or 55, therefore the fragment comprises a deletion at the 5' end of SEQ ID NO: 54 or 55.

A further embodiment of the invention is a composition comprising one or more recombinant microorganisms of the invention as defined above. The composition may further comprise a medium that allows grow of the recombinant microorganism of the invention. The medium may additionally comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose of sucrose, more preferably the carbon source is glucose.

In a preferred embodiment the composition comprises the microorganism of the invention and NBS medium, AM1 medium or PPM01 medium. More preferably the composition further comprises a carbon source, preferably a sugar. The ingredients of these media are known to a skilled person.

Preferably NBS medium comprises per liter
1-5 g, preferably 3.5 g $KH_2PO_4$ and
1-10 g, preferably 5.0 g $K_2HPO_4$ and
1-5 g, preferably 3.5 g $(NH_4)_2HPO_4$ and
0.1-1 g, preferably 0.25 g $MgSO_4$-7 $H_2O$ and
5-25 mg, preferably 15 mg $CaCL_2$-2 $H_2O$ and
0.1-1 mg, preferably 0.5 mg Thiamine and
0.1-5 ml, preferably 1 ml trace metal stock,
wherein the trace metal stock comprises 0.5-5 g, preferably 1.6 g $FeCL_3$-6 $H_2O$; 0.05-0.5 g, preferably 0.2 g $CoCl_2$-6 $H_2O$; 0.01-0.5 g, preferably 0.1 g $CuCl_2$-2 $H_2O$; 0.1-0.5 g, preferably 0.2 g $ZnCl_2$; 0.05-0.5 g, preferably 0.2 g $NaMoO_4$-2 $H_2O$; 0.001-0.1 g, preferably 0.05 g $H_3BO_3$ per liter 0.01-1 M, preferably 0.1 M HCL.

The preferred carbon source in the NBS medium is glucose or sucrose, preferably 2%-18% glucose or 2%-16% sucrose.

Preferably AM 1 medium comprises per liter 0.1-10 mM, preferably 1 mM betain solution
1-10 g, preferably 2.6 g $(NH_4)_2HPO_4$ and
0.1-5 g, preferably 0.87 g $NH_4H_2PO_4$ and
0.05-2.5 g, preferably 0.15 g KCl and
0.05-5 g, preferably 0.37 g $MgSO_4$-$7H_2O$ and
0.1-5 ml, preferably 1 ml trace metal stock,
wherein the trace metal stock comprises per liter 0.01-1 M, preferably 0.12 M HCL, 1-5 g, preferably 2.4 g $FeCL_3$-$6H_2O$; 0.1-1 g, preferably 0.3 g $CoCl_2$-$6H_2O$; 0.1-1 g, preferably 0.21 g $CuCl_2$-2 $H_2O$; 0.1-1 g, preferably 0.3 g $ZnCl_2$; 0.1-1 g, preferably 0.27 g $NaMoO_4$-2 $H_2O$; 0.01-0.5 g, preferably 0.068 g $H_3BO_3$ and 0.1-1 g, preferably 0.5 g $MnCl_2$-4 $H_2O$,
and optionally 1-30 g, preferably 15 g $(NH_4)_2SO_4$.

The preferred carbon source in the NBS medium is glucose or sucrose, preferably 2%-18% glucose or 2%-16% sucrose.

Preferably PPM01 medium comprises per liter
0.05-5 g, preferably 0.37 g $MgSO_4$-7 $H_2O$ and
0.1-10 g, preferably 1 g $(NH_4)_2SO_4$ and
0.05-5 g, preferably 0.46 g betaine and
0.001-0.5 g, preferably 0.05 g Cyanocobalamin (B12) and
1-10 g, preferably 3.74 g $KH_2PO_4$ and
0.1-5 ml, preferably 1 ml trace metal stock,
wherein the trace metal stock comprises per liter 10-100 mM, preferably 60 mM sulfuric acid, 1-10 g, preferably 3.48 g $(NH_4)_2Fe(II)(SO_4)_2$-7 $H_2O$; 0.1-1 g, preferably 0.35 g $CoSO_4$-7 $H_2O$; 0.1-1 g, preferably 0.31 g $CuSO_4$-5 $H_2O$; 0.1-5 g, preferably 0.63 g $ZnSO_4$-7 $H_2O$; 0.1-1 g, preferably 0.27 g $MnSO_4$—$H_2O$; 0.01-1 g, preferably 0.07 g $NaMoO_4$-2 $H_2O$ and 0.1-5 g, preferably 0.43 g $H_3BO_3$.

The preferred carbon source in the PPM01 medium is glucose monohydrate, preferably 10-500 g, more preferably 140 g glucose monohydrate per liter medium.

A further embodiment of the invention is a method for producing a recombinant microorganism with enhanced alanine, pyruvate, succinate, aspartate, malate, lactate, valine and/or leucine, preferably succinate or alanine, more preferably alanine yield or productivity, which comprises the following steps:

(I) introducing, increasing or enhancing of at least one of i) one or more activity and/or expression of the lpd gene, and/or ii) introducing, increasing, enhancing or altering of one or more activity and/or expression of the zipA gene, and/or iii) introducing a ygaW gene comprising a mutation in the codon at position 13-15 of SEQ ID NO: 1 or in a corresponding codon of functional equivalents of SEQ ID NO: 1, wherein the mutation is altering the activity and/or expression of the alanine transporter encoded by the ygaW gene and optionally further introducing one or more of the modifications as defined above under (a) to (e) in a microorganism; and (II) generating, identifying and isolating a recombinant microorganism with enhanced alanine, pyruvate, succinate, aspartate, malate, lactate, valine and/or leucine, preferably succinate or alanine, more preferably alanine yield or productivity compared to a corresponding microorganism without the modification as defined above under (I).

In a preferred embodiment the lpd gene with introduced, increased or enhanced activity and/or expression has a sequence of SEQ ID NO: 51 and/or is encoding a polypeptide of SEQ ID NO: 52.

In a preferred embodiment the zipA gene with introduced, increased, enhanced or altered activity and/or expression has a sequence of SEQ ID NO: 47 and/or is encoding a polypeptide of SEQ ID NO: 48.

In a preferred embodiment the ygaW gene with altered activity and/or expression has a sequence of SEQ ID NO: 3, 56, 58 or 60 and/or is encoding a polypeptide of SEQ ID NO: 4, 57, 59 or 61.

In a preferred embodiment of the method for producing a recombinant microorganism of the invention the method further comprises the step of reducing, repressing or deleting the activity and/or expression of at least one, at least two, at least three, at least four or all of the pflB gene, adhE gene, ldhA gene, pta gene or frdA gene for example as defined above under (A) to (Y) and/or the step of introducing, increasing or enhancing activity and/or expression of an alaD gene for example as defined above under (Z) to (DD).

In a further preferred embodiment of the method for producing a recombinant microorganism of the invention the nucleic acid molecule as defined in (Z) to (DD) is under control of a sequence functioning as a promoter in a microorganism having the sequence of (1) a nucleic acid molecule comprising a sequence of SEQ ID NO: 54 or 55, or (2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 54 or 55, or (3) a nucleic acid molecule hybridizing to a nucleic acid molecule having SEQ ID NO: 54 or 55 under medium stringent conditions, more preferably under high stringent conditions, most preferably under very high stringent conditions or (4) a fragment of at least 10 nucleotides, preferably at least 20 nucleotides, at least 30 nucleotides or at least 40 nucleotides, more preferably a fragment of at least 50 nucleotides, at least 75 nucleotides or at least 100 nucleotides, even more preferably at least 150 or at least 200 nucleotides of the nucleic acid molecule having SEQ ID NO: 54 or 55. Preferably the fragment of SEQ ID NO: 54 or 55 is a fragment comprising the 3' region of SEQ ID NO: 54 or 55, therefore the fragment comprises a deletion at the 5' end of SEQ ID NO: 54 or 55.

A most preferred method for producing a recombinant microorganism of the invention comprises the step of i) reducing, repressing or deleting the activity and/or expression of all of the pflB gene, adhE gene, ldhA gene, pta gene and frdA gene and ii) the step of introducing, increasing or enhancing activity and/or expression of an alaD gene preferably under control of a promoter comprising the sequence of SEQ ID NO: 54 or 55 and iii) introducing, increasing or enhancing activity and/or expression of an lpd gene, preferably having a sequence of SEQ ID NO: 51 and/or encoding a polypeptide of SEQ ID NO: 52 and iv) introducing or altering the activity and/or expression of a zipA gene, preferably having a sequence of SEQ ID NO: 47 and/or encoding a polypeptide of SEQ ID NO: 48 and v) introducing a ygaW gene with altered activity and/or expression or introducing a mutation into an endogenous ygaW gene which has a sequence of SEQ ID NO: 3, 56, 58 or 60 and/or is encoding a polypeptide of SEQ ID NO: 4, 57, 59 or 61.

In one embodiment of the method for producing a recombinant microorganism of the invention the microorganism is selected from the group consisting of species of the genus *Corynebacterium*, e.g. *C. acetophilum*, *C. glutamicum*, *C. callunae*, *C. acetoacidophilum*, *C. acetoglutamicum*, species of the genus *Bacillus*, e.g., *B. thuringiensis*, *B. anthracis*, *B. megaterium*, *B. subtilis*, *B. lentils*, *B. circulans*, *B. pumilus*, *B. lautus*, *B. coagulans*, *B. brevis*, *B. firmus*, *B. alkaophius*, *B. licheniformis*, *B. clausii*, *B. stearothermophilus*, *B. halodurans*, *B. subtilis*, *B. pumilus*, and *B. amyloliquefaciens*, species of the genus *Erwinia*, e.g., *E. uredovora*, *E. carotovora*, *E. ananas*, *E. herbicola*, *E. punctate*, *E. terreus*, species of the genus *Escherichia*, e.g., *E. coli*, species of the genus *Pantoea*, e.g., *P. citrea*, *P. agglomerans*, species of the genus *Streptomyces*, e.g., *S. ambofaciens*, *S. achromogenes*, *S. avermitilis*, *S. coelicolor*, *S. aureofaciens*, *S. aureus*, *S. fungicidicus*, *S. griseus*, *S. lividans*, species of the genus *Zymomonas*, e.g., *Z. mobilis* or *Z. lipolytica* and species of the genus *Rhodococcus*, e.g. *R. opacus*.

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

A further embodiment of the invention is a method of producing alanine, pyruvate, succinate, aspartate, malate, lactate, valine and/or leucine, preferably succinate or alanine, more preferably alanine, most preferably L-alanine, comprising culturing one or more recombinant microorganism as defined above under conditions that allow for the production of alanine, pyruvate, succinate, aspartate, malate, lactate, valine and/or leucine, preferably succinate or alanine, more preferably alanine, most preferably L-alanine.

In some embodiments, the recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 34° C., 35° C. or 36° C. In a most preferred embodiment the temperature is about 37° C. or 38° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 7.

In one embodiment of the method of producing alanine, pyruvate, succinate, aspartate, malate, lactate, valine and/or leucine, preferably succinate or alanine, more preferably alanine, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 17% (w/v) of a sugar.

In another embodiment of the method for producing alanine, pyruvate, succinate, aspartate, malate, lactate, valine and/or leucine, preferably succinate or alanine, more preferably alanine the yield of alanine, pyruvate, succinate, aspartate, malate, lactate, valine and/or leucine is at least 80% for example at least 81%, at least 82%, at least 83%, at least 84% or at least 85%. Preferably the yield is at least 86%, at least 87%, at least 88%, at least 89% or at least 90%. More preferably the yield is at least 90.5%, at least 91%, at least 91.5%, at least 92%, at least 92.5%, at least 93%, at least 93.5%, at least 94% or at least 94.5%. In an even more preferred embodiment the yield is at least 95% or at least 95.5%. In a most preferred embodiment, the yield is at least 96%. The percent yield is calculated as gram product produced from gram glucose in the medium. Hence, when the medium contained 100 g glucose and the fermentation yielded 98 g alanine, the yield would be 98%.

In another embodiment of the method for producing alanine preferably L-alanine is produced, wherein the chiral purity of L-alanine is at least 90%, at least 91%, at least 92%, at least 93% or at least 94%. In a preferred embodiment the chiral purity of L-alanine is at least 95% or at least 95.5%. In a more preferred embodiment, the chiral purity of L-alanine is at least 96% or at least 96.5% or at least 97%. In an even more preferred embodiment the chiral purity of L-alanine is at least 97.5%, at least 98% or at least 98.5% for example at least 99%. Even more preferably the chiral purity of L-alanine is at least 99.5% or at least 99.6% for example at least 99.7%, at least 99.8%, or at least 99.9%. In a most preferred embodiment chiral pure L-alanine is produced.

Another embodiment of the invention is a method of culturing or growing any of the genetically modified microorganisms as defined above, the method comprising inoculating a culture medium with one or more genetically modified microorganism and culturing or growing said genetically modified microorganism in culture medium under conditions as defined above.

The use of a recombinant microorganism as defined above or a composition as defined above for the fermentative production of alanine, pyruvate, succinate, aspartate, malate, lactate, valine and/or leucine, preferably succinate or alanine, more preferably alanine, most preferably L-alanine is an additional embodiment of the invention.

The recombinant microorganism according to the present invention is characterized in that, compared to a respective reference microorganism for example a wild type, the expression and/or the activity of the enzyme that is encoded by the lpd gene is increased and/or the expression and/or the activity of the enzyme that is encoded by the zipA gene is increased or altered and/or the ygaW gene activity and/or expression is altered by introducing a mutation in the codon at position 13-15 of SEQ ID NO: 1 or in a corresponding codon of functional equivalents of SEQ ID NO: 1.

In one embodiment the decrease of the expression and/or activity of a gene is achieved by a deactivation, mutation or knock-out of the gene. This could be done by deletion of part or total of the coding region an/or the promoter of the gene, by mutation of the gene such as insertion or deletion of a number of nucleotides for example one or two nucleotides leading to a frameshift in the coding region of the gene, introduction of stop codons in the coding region, inactivation of the promoter of the gene by for example deleting or mutating promoter boxes such as ribosomal entry sides, the TATA box and the like. The decrease may also be achieved by degrading the transcript of the gene for example by means of introduction of ribozymes, dsRNA, antisense RNA or antisense oligonucleotides. The decrease of the activity of a gene may be achieved by expressing antibodies or aptamers in the cell specifically binding the target enzyme. Other methods for the decrease of the expression and/or activity of a gene are known to a skilled person.

In one embodiment of the invention the increase of the expression and/or activity of the lpd gene is achieved by introduction of a mutation into the gene, preferably a point mutation which leads to an exchange of the amino acid at position 70 of the protein of SEQ ID 50 from alanine to proline.

Preferably the increase of the expression and/or activity of the lpd gene is achieved by introducing a mutation in the lpd gene, wherein the mutated lpd gene has the sequence of SEQ ID NO: 51, encoding a protein of SEQ ID NO: 52.

In one embodiment of the invention the increase of the expression and/or activity of the zipA gene is achieved by introduction of a mutation into the gene, preferably a point mutation. More preferably the point mutation is introduced into the codon 913-915 of a zipA gene encoded by SEQ ID NO: 45 or a functional homolog thereof leading to an exchange on position 305 of the respective protein of the amino acid arginine to glycine or another aliphatic amino acid or an amino acid related to glycine as shown in table 2.

Preferably the increase of the expression and/or activity of the zipA gene is achieved by introducing a mutation in the zipA gene, wherein the mutated zipA gene has the sequence of SEQ ID NO: 47, encoding a protein of SEQ ID NO: 48.

The reduced expression and/or activity of the enzymes disclosed herein, in particular the reduced expression and/or reduced activity of the enzyme encoded by the lactate dehydrogenase (ldhA), pyruvate formate lyase I (pflB), bifunctional acetaldehyde-CoA dehydrogenase/iron-dependent alcohol dehydrogenase/pyruvate-formate lyase deactivase (adhE), phosphate acetyltransferase (pta) and/or fumarate reductase (frdA), can be a reduction of the expression and/or enzymatic activity by at least 50%, compared to the expression and/or activity of said enzyme in a respective reference microorganism for example the wild type of the microorganism, or a reduction of the expression and/or enzymatic activity by at least 90%, or more preferably a reduction of expression and/or the enzymatic activity by at least 95%, or more preferably an expression and/or reduction of the enzymatic activity by at least 98%, or even more preferably a reduction of the expression and/or enzymatic activity by at least 99% or even more preferably a reduction of the expression and/or the enzymatic activity by at least 99.9%. In a most preferred embodiment the expression and/or activity of the enzymes is not detectable in the microorganism of the invention.

The enhanced or increased expression and/or activity of the enzymes disclosed herein, in particular the enhanced or increased expression and/or activity of the enzyme encoded by the lpd-gene and/or the zipA-gene and/or the ygaW gene, can be an increase of the expression and/or enzymatic activity by at least 25%, compared to the expression and/or activity of said enzyme in a respective reference microorganism for example the wild type of the microorganism, or an increase of the expression and/or enzymatic activity by at least 50%, or more preferably an increase of expression and/or the enzymatic activity by at least 100%, or more preferably an increase of the expression and/or of the enzymatic activity by at least 3 fold, for example at least 5 fold, or even more preferably an increase of the expression and/or enzymatic activity by at least 10 fold or even more preferably an increase of the expression and/or the enzymatic activity by at least 20 fold.

The increase of the expression and/or activity of the lpd gene and/or the zipA gene and/or the ygaW gene leads to an improved yield and/or productivity of alanine, pyruvate, succinate, aspartate, malate, lactate, valine and/or leucine, preferably succinate or alanine, more preferably alanine in the recombinant microorganism of the invention compared to a respective reference microorganism. Therefore the increase of the expression and/or activity of the lpd gene and/or the zipA gene and/or the ygaW gene may be determined by measuring alanine, pyruvate, succinate, aspartate, malate, lactate, valine and/or leucine, preferably succinate or alanine, more preferably alanine yield or productivity of the recombinant microorganism of the invention compared to a respective reference microorganism. Methods for fermentative production of metabolites, for example alanine are known to a skilled person and also described herein. Improved yield of e.g. alanine in fermentation by the microorganism of the invention compared to yield of alanine in fermentation by a respective reference microorganism is a measure for the increase of expression and or activity of the lpd gene and/or the zipA gene and/or the ygaW gene.

Methods for determining the lactate dehydrogenase (ldhA) expression or activity are, for example, disclosed by Bunch et al. in "The ldhA gene encoding the fermentative lactate de hydrogenase of *Escherichia Coli*", Microbiology (1997), Vol. 143, pages 187-155; or Bergmeyer, H. U., Bergmeyer J. and Grassi, M. (1983-1986) in "Methods of Enzymatic Analysis", 3rd Edition, Volume III, pages 126-133, Verlag Chemie, Weinheim; or Enzymes in Industry: Production and Applications, Second Edition (2004), Wolfgang Aehle, page 23. Preferred is the last method.

Methods for determining the pyruvate formate lyase I (pflB) expression or activity are, for example, disclosed in Knappe J, Blaschkowski H P, Grobner P, Schmitt T (1974). "Pyruvate formate-lyase of *Escherichia coli*: the acetyl-enzyme intermediate." Eur J Biochem 1974; 50(1); 253-63. PMID: 4615902; in KNAPPE, Joachim, et al. "Pyruvate Formate-Lyase of *Escherichia coli*: the Acetyl-Enzyme Intermediate." European Journal of Biochemistry 50.1 (1974): 253-263; in Wong, Kenny K., et al. "Molecular properties of pyruvate formate-lyase activating enzyme." Biochemistry 32.51 (1993): 14102-14110 and in Nnyepi, Mbako R., Yi Peng, and Joan B. Broderick. "Inactivation of *E. coli* pyruvate formate-lyase: Role of AdhE and small molecules." Archives of biochemistry and biophysics 459.1 (2007): 1-9.

Methods for determining the bifunctional acetaldehyde-CoA dehydrogenase/iron-dependent alcohol dehydrogenase/pyruvate-formate lyase deactivase (adhE) expression or activity are, for example, disclosed in Membrillo-Hernández, Jorge, et al. "Evolution of the adhE Gene Product of *Escherichia coli* from a Functional Reductase to a Dehydrogenase GENETIC AND BIOCHEMICAL STUDIES OF THE MUTANT PROTEINS." Journal of Biological Chemistry 275.43 (2000): 33869-33875 and in Mbako R. Nnyepi, Yi Peng, Joan B. Broderick, Inactivation of *E. coli* pyruvate formate-lyase: Role of AdhE and small molecules, Archives of Biochemistry and Biophysics, Volume 459, Issue 1, 1 Mar. 2007, Pages 1-9.

Methods for determining the phosphate acetyltransferase (pta) expression or activity are, for example, disclosed in Dittrich, Cheryl R., George N. Bennett, and Ka-Yiu San. "Characterization of the Acetate-Producing Pathways in *Escherichia coli*." Biotechnology progress 21.4 (2005): 1062-1067 and in Brown, T. D. K., M. C. Jones-Mortimer, and H. L. Kornberg. "The enzymic interconversion of acetate and acetyl-coenzyme A in *Escherichia coli*." Journal of general microbiology 102.2 (1977): 327-336.

Methods for determining the fumarate reductase (frdA) expression or activity are, for example, disclosed in Dickie, Peter, and Joel H. Weiner. "Purification and characterization of membrane-bound fumarate reductase from anaerobically grown *Escherichia coli*." Canadian journal of biochemistry 57.6 (1979): 813-821; in Cecchini, Gary, et al. "Reconstitution of quinone reduction and characterization of *Escherichia coli* fumarate reductase activity." Journal of Biological Chemistry 261.4 (1986): 1808-1814 or in Schröder, I., et al. "Identification of active site residues of *Escherichia coli* fumarate reductase by site-directed mutagenesis." Journal of Biological Chemistry 266.21 (1991): 13572-13579.

Methods for determining the alanine dehydrogenase (alaD) expression or activity are, for example, disclosed in Sakamoto, Y., Nagata, S., Esaki, N., Tanaka, H., Soda, K. "Gene cloning, purification and characterization of thermostable alanine dehydrogenase of *Bacillus stearothermophilus*" J Fermen. Bioeng. 69 (1990):154-158.

The term "reduced expression of an enzyme" includes, for example, the expression of the enzyme by said genetically manipulated (e.g., genetically engineered) microorganism at a lower level than that expressed by a respective reference microorganism for example the wild type of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more deleterious gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

A deleterious mutation according to this application is any mutation within a gene comprising promoter and coding region that lead to a decreased or deleted protein activity of the protein encoded by the coding region of the gene. Such deleterious mutations comprise for example frameshifts, introduction of stop-codons in the coding region, mutation of promoter elements such as the TATA box that prevent transcription and the like.

Microorganisms having an increased or enhanced expression and/or activity of the enzyme encoded by the lpd-gene and/or the zipA-gene and/or the ygaW-gene may occur naturally, i.e. due to spontaneous mutations. A microorganism can be modified to have significantly increased activity of the enzyme that is encoded by one or more of said genes by various techniques, such as chemical treatment or radiation. To this end, microorganisms will be treated by, e.g., a mutagenizing chemical agent, X-rays, or UV light. In a subsequent step, those microorganisms which have an increased expression and/or activity of the enzyme that is encoded by one or more of said genes will be selected. Recombinant microorganisms are also obtainable by homologous recombination techniques which aim to substitute one or more of said genes with a corresponding gene that encodes for an enzyme which, compared to the enzyme encoded by the wild type gene, has an increased expression and/or activity.

According to one embodiment of the recombinant microorganism according to the present invention, an increase of the expression and/or activity of the enzyme encoded by the lpd-gene and/or the zipA-gene and/or the ygaW-gene may be achieved by a modification of the lpd-gene and/or the zipA-gene and/or the ygaW-gene, wherein this/these gene modification(s) is(are) preferably realized by multiplication of the copy-number of the lpd gene and/or the zipA-gene and/or the ygaW-gene in the genome of the microorganism, by introducing the gene on a self-replicating expression vector into the microorganism, by exchanging the promoter of the lpd-gene and/or the zipA-gene and/or the ygaW-gene against a stronger promoter or by converting the endogenous promoter of the gene into a stronger promoter, e.g. by introducing point-mutations into the promoter sequence.

Further the activity of the lpd-gene and/or the zipA-gene and/or the ygaW-gene may be enhanced by mutating the gene in order to achieve amino acid exchanges in the protein which improve activity of the gene. Such methods are known to a skilled person.

A mutation into the above-gene can be introduced, for example, by site-directed or random mutagenesis, followed by an introduction of the modified gene into the genome of the microorganism by recombination. Variants of the genes can be are generated by mutating the gene sequences by means of PCR. The "Quickchange Site-directed Mutagenesis Kit" (Stratagene) can be used to carry out a directed mutagenesis. A random mutagenesis over the entire coding sequence, or else only part thereof, can be performed with the aid of the "GeneMorph II Random Mutagenesis Kit" (Stratagene). The mutagenesis rate is set to the desired amount of mutations via the amount of the template DNA used. Multiple mutations are generated by the targeted combination of individual mutations or by the sequential performance of several mutagenesis cycles.

In the following, a suitable technique for recombination, in particular for introducing a mutation or for deleting sequences, is described.

This technique is also sometimes referred to as the "Campbell recombination" herein (Leenhouts et al., *Appl Env Microbiol.* (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

In one embodiment the induction of the expression and/or activity of lpd is achieved by an activation of the lpd-gene which encodes the lipoamide dehydrogenase.

In one embodiment the induction of the expression and/or activity of zipA is achieved by an activation of the zipA-gene which encodes the cell division protein involved in Z ring assembly.

The terms "alanine, pyruvate, succinate, aspartate, malate, lactate, valine and/or leucine", as used in the context of the present invention, has to be understood in their broadest sense and also encompasses salts thereof, as for example alkali metal salts, like $Na^+$ and $K^+$-salts, or earth alkali salts, like $Mg^{2+}$ and $Ca^{2+}$-salts, or ammonium salts or anhydrides of alanine, pyruvate, succinate, aspartate, malate, lactate, valine and/or leucine.

Preferably, alanine, pyruvate, succinate, aspartate, malate, lactate, valine and/or leucine, preferably succinate or alanine, more preferably alanine is produced under microaerobic conditions. Aerobic or anaerobic conditions may be also used.

Microaerobic means that the concentration of oxygen is less than that in air. According to one embodiment microaerobic means oxygen tension between 5 and 27 mm Hg, preferably between 10 and 20 Hg (Megan Falsetta et al. (2011), The composition and metabolic phenotype of *Neisseria gonorrhoeae* biofilms, Frontiers in Microbiology, Vol 2, page 1 to 11). Preferably the microaerobic conditions are established with 0.1 to 1 vvm air flow.

Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

According to one embodiment of the process according to the present invention the assimilable carbon source may be glucose, glycerin, glucose, maltose, maltodextrin, fructose, galactose, mannose, xylose, sucrose, arabinose, lactose, raffinose and combinations thereof.

In a preferred embodiment the assimilable carbon source is glucose, sucrose, xylose, arabinose, glycerol or combinations thereof. Preferred carbon sources are glucose, sucrose, glucose and sucrose, glucose and xylose and/or glucose, arabinose and xylose. According to one embodiment of the process according to the present invention the assimilable carbon source may be sucrose, glycerin and/or glucose.

The initial concentration of the assimilable carbon source, preferably the initial concentration is, preferably, adjusted to a value in a range of 5 to 250 g/l, preferably 50 to 200 g/l and more preferably 125 to 150 g/l, most preferably about 140 g/l and may be maintained in said range during cultivation. The pH of the reaction medium may be controlled by addition of suitable bases as for example, gaseous ammonia, $NH_4OH$, $NH_4HCO_3$, $(NH_4)_2CO_3$, $NaOH$, $Na_2CO_3$, $NaHCO_3$, $KOH$, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, $CaO$, $CH_6N_2O_2$, $C_2H_7N$ and/or mixtures thereof.

Another embodiment of the invention is a process for fermentative production of alanine, pyruvate, succinate, aspartate, malate, lactate, valine and/or leucine, preferably succinate or alanine, more preferably alanine, most preferably L-alanine comprising the steps of
I) growing the microorganism according to the invention as defined above in a fermenter and
II) recovering alanine, pyruvate, succinate, aspartate, malate, lactate, valine and/or leucine, preferably succinate or alanine, more preferably alanine, most preferably L-alanine from the fermentation broth obtained in I).

The fermentation step I) according to the present invention can, for example, be performed in stirred fermenters, bubble columns and loop reactors. A comprehensive overview of the possible method types including stirrer types and geometric designs can be found in Chmiel: "*Bioprozesstechnik: Einführung in die Bioverfahrenstechnik*", Volume 1. In the process according to the present invention, typical variants available are the following variants known to those skilled in the art or explained, for example, in Chmiel, Hammes and Bailey: "*Biochemical Engineering*", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing alanine, pyruvate, succinate, aspartate, malate, lactate, valine and/or leucine, preferably succinate or alanine, more preferably alanine, most preferably L-alanine in process step I) are:

Assimilable carbon source: glucose
Temperature: 30 to 45° C.
pH: 6.0 to 7.0
Microaerobic conditions In process step II) the product is recovered from the fermentation broth obtained in process step I).

Usually, the recovery process comprises the step of separating the recombinant microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the fermentation product is further purified. If, however, the fermentation product is converted into a secondary organic product by chemical reactions, a further purification of the fermentation product might, depending on the kind of reaction and the reaction conditions, not necessarily be required. For the purification of the fermentation product obtained in process step II) methods known to the person skilled in the art can be used, as for example crystallization, filtration, electrodialysis and chromatography. The resulting solution may be further purified by means of ion exchange chromatography in order to remove undesired residual ions.

In one embodiment, the enhanced or increased expression and/or activity of the lpd gene is achieved by introducing a mutation into the wild-type gene. Preferably it is achieved by introducing a specific mutation in the codon at position 208-210 of the wild type gene having SEQ ID NO: 1 or a functional variant thereof.

Therefore a further embodiment of the invention is a recombinant nucleic acid molecule having a sequence selected from the group of
(1) a nucleic acid molecule comprising a sequence of SEQ ID NO: 49, or
(2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 49, or
(3) a nucleic acid molecule hybridizing to a nucleic acid molecule having SEQ ID NO: 49 under medium stringent conditions, more preferably under high stringent conditions, most preferably under very high stringent conditions, or
(4) a nucleic acid molecule encoding a polypeptide of SEQ ID NO: 50, or (5) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 50, and wherein the codon of the genes under (1) to (5) corresponding to position 208-210 of SEQ ID NO: 49 is not encoding amino acid alanine and is not a stop codon or the amino acid of the proteins encoded by the genes under (1) to (5) corresponding to position 70 of SEQ ID NO: 50 is not alanine, and wherein the protein encoded by the gene as defined above in (1) to (5) has an enhanced or increased activity compared to the protein having SEQ ID NO: 50, and wherein the microorganism comprising the mutated gene and/or protein as defined above has an improved Alanine yield in fermentation.

Preferably, the recombinant nucleic acid molecule is having a sequence selected from the group of (6) a nucleic acid molecule comprising a sequence of SEQ ID NO: 51, or (7) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 51, or (8) a nucleic acid molecule hybridizing to a nucleic acid molecule having SEQ ID NO: 51 under medium stringent conditions, more preferably under high stringent conditions, most preferably under very high stringent conditions, or (9) a nucleic acid molecule encoding a polypeptide of SEQ ID NO: 52, or

(10) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 52, wherein the codon of the genes under (7) to (10) corresponding to position 208-210 of SEQ ID NO: 51 is encoding amino acid proline or the amino acid of the proteins encoded by the genes under (7) to (10) corresponding to position 70 of SEQ ID NO: 52 is proline, and wherein the protein encoded by the gene as defined above in (7) to (10) has an enhanced or increased activity compared to the protein having SEQ ID NO: 52, and wherein the microorganism comprising the mutated gene and/or protein as defined above has an improved Alanine yield in fermentation.

In another embodiment, the enhanced, increased or altered expression and/or activity of the zipA gene is achieved by introducing a mutation into the wild-type gene. Preferably it is achieved by introducing a specific mutation in the codon at position 913-915 of the wild type gene having SEQ ID NO: 45 or a functional variant thereof.

Therefore a further embodiment of the invention is a recombinant nucleic acid molecule having a sequence selected from the group of (1) a nucleic acid molecule comprising a sequence of SEQ ID NO: 45, or (2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 45, or (3) a nucleic acid molecule hybridizing to a nucleic acid molecule having SEQ ID NO: 45 under medium stringent conditions, more preferably under high stringent conditions, most preferably under very high stringent conditions, or (4) a nucleic acid molecule encoding a polypeptide of SEQ ID NO: 46, or (5) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 46, and wherein the codon of the genes under (1) to (5) corresponding to position 913-915 of SEQ ID NO: 45 is not encoding amino acid arginine and is not a stop codon or the amino acid of the proteins encoded by the genes under (1) to (5) corresponding to position 305 of SEQ ID NO: 46 is not arginine, and wherein the protein encoded by the gene as defined above in (1) to (5) has an enhanced or increased or altered activity compared to the protein having SEQ ID NO: 46, and wherein the microorganism comprising the mutated gene and/or protein as defined above has an improved Alanine yield in fermentation.

Preferably, the recombinant nucleic acid molecule is having a sequence selected from the group of (6) a nucleic acid molecule comprising a sequence of SEQ ID NO: 47, or (7) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 47, or (8) a nucleic acid molecule hybridizing to a nucleic acid molecule having SEQ ID NO: 47 under medium stringent conditions, more preferably under high stringent conditions, most preferably under very high stringent conditions, or (9) a nucleic acid molecule encoding a polypeptide of SEQ ID NO: 48, or

(10) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 48, wherein the codon of the genes under (7) to (10) corresponding to position 913-915 of SEQ ID NO: 47 is encoding amino acid glycine or a related amino acid or another aliphatic amino acid or the amino acid of the proteins encoded by the genes under (7) to (10) corresponding to position 305 of SEQ ID NO: 48 is glycine or a related amino acid or another aliphatic amino acid, and wherein the protein encoded by the gene as defined above in (7) to (10) has an enhanced, increased or altered activity compared to the protein having SEQ ID NO: 48, and wherein the microorganism comprising the mutated gene and/or protein as defined above has an improved Alanine yield in fermentation.

In one embodiment, the enhanced or increased yield and/or productivity of alanine or related compounds is achieved by introducing a mutation into the wild-type ygaW gene.

Therefore one embodiment of the invention is a recombinant nucleic acid molecule having a sequence selected from the group of
(1) a nucleic acid molecule comprising a sequence of SEQ ID NO: 1, or
(2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, or
(3) a nucleic acid molecule hybridizing to a nucleic acid molecule having SEQ ID NO: 1 under medium stringent conditions, more preferably under high stringent conditions, most preferably under very high stringent conditions, or
(4) a nucleic acid molecule encoding a polypeptide of SEQ ID NO: 2, or
(5) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 2, and
wherein the codon of the genes under (1) to (5) corresponding to position 13-15 of SEQ ID NO: 1 is not encoding amino acid glutamine and is not a stop codon or the amino acid of the proteins encoded by the genes under (1) to (5) corresponding to position 5 of SEQ ID NO: 2 is not glutamine, and
wherein the protein encoded by the gene as defined above in (1) to (5) has an altered activity and/or expression compared to the protein having SEQ ID NO: 2, and
wherein the microorganism comprising the mutated gene and/or protein as defined above has an improved alanine yield in fermentation.

Preferably, the recombinant nucleic acid molecule is having a sequence selected from the group of
(6) a nucleic acid molecule comprising a sequence of SEQ ID NO: 3, 56, 58 or 60, or
(7) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 56, 58 or 60, or
(8) a nucleic acid molecule hybridizing to a nucleic acid molecule having SEQ ID NO: 3, 56, 58 or 60 under medium stringent conditions, more preferably under high stringent conditions, most preferably under very high stringent conditions, or
(9) a nucleic acid molecule encoding a polypeptide of SEQ ID NO: 4, 57, 59, or 60, or
(10) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 4, 57, 59, or 60,
wherein the codon of the genes under (7) to (10) corresponding to position 13-15 of SEQ ID NO: 3 is encoding amino acid histidine or a related amino acid or another basic amino acid or is encoding amino acid asparagine or a related amino acid or another aliphatic amino acid or is encoding the amino acid arginine or a related amino acid or another aliphatic amino acid or is encoding amino acid tyrosine or a related amino acid or another aromatic amino acid or the amino acid of the proteins encoded by the genes under (7) to (10) corresponding to position 5 of SEQ ID NO: 2 is histidine or a related amino acid or another basic amino acid or is asparagine or a related amino acid or another aliphatic amino acid or is arginine or a related amino acid or another aliphatic amino acid or is tyrosine or a related amino acid or another aromatic amino acid, and
wherein the protein encoded by the gene as defined above in (7) to (10) has an altered activity and/or expression compared to the protein having SEQ ID NO: 2, and
wherein the microorganism comprising the mutated gene and/or protein as defined above has an improved alanine yield in fermentation.

The term "related amino acid" or "conservative amino acid substitution" means that an amino acid is replaced by an amino acid having a similar side-chain. A list of related amino acids is given in the table 2 below. Conservative substitution tables are well known in the art (see for example Creighton (1984) Proteins. W.H. Freeman and Company (Eds) and Table 2 below).

TABLE 2

| Examples of conserved amino acid substitutions | |
|---|---|
| Residue | Conservative Substitutions |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

In a preferred embodiment the recombinant nucleic acid molecule has SEQ ID NO: 3, 56, 58, 60, 47 or 51 and is encoding a protein having SEQ ID NO: 4, 57, 59, 61, 48 or 52.

A further embodiment of the invention is a recombinant amino acid molecule having a sequence selected from the group of
(11) an amino acid molecule comprising a sequence of SEQ ID NO: 52, or
(12) an amino acid molecule having 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 52,
wherein the amino acid of the protein under (12) corresponding to position 70 of SEQ ID NO: 52 is proline, and wherein the protein as defined above in (12) has an enhanced or increased activity compared to the protein having SEQ ID NO: 50, and
wherein the microorganism comprising the mutated gene and/or protein as defined above has an improved Alanine yield in fermentation.

Preferably the recombinant amino acid molecule of the invention has SEQ ID NO: 52.

A further embodiment of the invention is a recombinant amino acid molecule having a sequence selected from the group of
(11) an amino acid molecule comprising a sequence of SEQ ID NO: 48, or
(12) an amino acid molecule having 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 48,
wherein the amino acid of the protein under (12) corresponding to position 305 of SEQ ID NO: 48 is glycine or a related amino acid or another aliphatic amino acid, and
wherein the protein as defined above in (12) has an enhanced, increased or latered activity compared to the protein having SEQ ID NO: 46, and
wherein the microorganism comprising the mutated gene and/or protein as defined above has an improved Alanine yield in fermentation.

Preferably the recombinant amino acid molecule of the invention has SEQ ID NO: 48.

A further embodiment of the invention is a recombinant amino acid molecule having a sequence selected from the group of
(11) an amino acid molecule comprising a sequence of SEQ ID NO: 4, 57, 59 or 61 or
(12) an amino acid molecule having 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 4, 57, 59 or 61
wherein the amino acid of the protein under (12) corresponding to position 5 of SEQ ID NO: 4 is histidine or a related amino acid or another basic amino acid, and
wherein the amino acid of the protein under (12) corresponding to position 5 of SEQ ID NO: 57 is asparagine or a related amino acid or another aliphatic amino acid, and
wherein the amino acid of the protein under (12) corresponding to position 5 of SEQ ID NO: 59 is arginine or a related amino acid or another aliphatic amino acid and
wherein the amino acid of the protein under (12) corresponding to position 5 of SEQ ID NO: 61 is tyrosine or a related amino acid or another aromatic amino acid, and
wherein the protein as defined above in (12) has an altered activity and/or expression compared to the protein having SEQ ID NO: 2, and
wherein the microorganism comprising the mutated gene and/or protein as defined above has an improved alanine yield in fermentation.

Preferably the recombinant amino acid molecule of the invention has SEQ ID NO: 4, 57, 59 or 61.

A further embodiment of the invention is a recombinant expression construct comprising a promoter functional in a microorganism operably linked to the nucleic acid as defined in above in (1) to (5).

A further embodiment of the invention is a recombinant vector comprising the nucleic acid molecule as defined above in (1) to (5) or the recombinant expression construct as defined above.

A further embodiment of the invention is a promoter functional in a microorganism, for example E. coli having a sequence selected from the group of
(I) a nucleic acid molecule comprising a sequence of SEQ ID NO: 54 or 55, or
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 54 or 55, or
(III) a nucleic acid molecule hybridizing to a nucleic acid molecule having SEQ ID NO: 54 or 55 under medium stringent conditions, more preferably under high stringent conditions, most preferably under very high stringent conditions, or
(IV) a fragment of at least 10 nucleotides, preferably at least 20 nucleotides, at least 30 nucleotides or at least 40 nucleotides, more preferably a fragment of at least 50 nucleotides, at least 75 nucleotides or at least 100 nucleotides, even more preferably at least 150 or at least 200 nucleotides of the nucleic acid molecule having SEQ ID NO: 54 or 55. Preferably the fragment of SEQ ID NO: 54 or 55 is a fragment comprising the 3' region of SEQ ID NO: 54 or 55, therefore the fragment comprises a deletion at the 5' end of SEQ ID NO: 54 or 55.

Preferably the nucleic acid molecules as defined in (II) t (IV) have promoter activity in microorganisms as defined herein.

A further embodiment of the invention is a recombinant expression construct comprising a promoter as defined above in (I) to (IV) functional in a microorganism operably linked to nucleic acid to be expressed heterologous to the promoter as defined in (I) to (IV).

A further embodiment of the invention is a recombinant vector comprising the nucleic acid molecule as defined above in (I) to (IV) or the recombinant expression construct as defined above.

A further embodiment of the invention is a recombinant microorganism comprising the recombinant expression construct as defined above or the vector as defined above. Preferably the microorganism is selected from the group of microorganisms as listed herein.

A further embodiment of the invention is a method for expressing a nucleic acid molecule in a microorganism comprising the steps of functionally linking of the promoter as defined above to a heterologous nucleic acid molecule to be expressed, thereby creating a recombinant expression construct and introducing said expression construct into a microorganism. The promoter of the invention may be functionally linked to the nucleic acid molecule to be expressed with means of recombinant DNA technologies outside the microorganism and subsequently introduced into the microorganism or it may be functionally linked by introducing the nucleic acid to be expressed into the genome of a microorganism in the vicinity of the promoter of the invention present in the microorganism, thereby linking the nucleic acid to be expressed to the promoter of the invention.

A further embodiment of the invention is the use of the promoter as defined above, the recombinant expression construct as defined above or the vector as defined above for expressing a nucleic acid molecule in a microorganism.

Definitions

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as start codon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self-replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41$ (% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6. Suitable hybridization conditions are for example hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. (low stringency) to a nucleic acid molecule comprising at least 50, preferably at least 100, more preferably at least 150, even more preferably at least 200, most preferably at least 250 consecutive nucleotides of the complement of a sequence. Other suitable hybridizing conditions are hybridization in 7% sodium dodecyl sulfate (SDS), 0.5 M NaPO4, 1 mM EDTA at 50° C. with washing in 1×SSC, 0.1% SDS at 50° C. (medium stringency) or 65° C. (high stringency) to a nucleic acid molecule comprising at least 50, preferably at least 100, more preferably at least 150, even more preferably at least 200, most preferably at least 250 consecutive nucleotides of a complement of a sequence. Other suitable hybridization conditions are hybridization in 7% sodium dodecyl sulfate (SDS), 0.5 M NaPO4, 1 mM EDTA at 50° C. with washing in 0.1×SSC, 0.1% SDS at 65° C. (very high stringency) to a nucleic acid molecule comprising at least 50, preferably at least 100, more preferably at least 150, even more preferably at least 200, most preferably at least 250 consecutive nucleotides of a complement of a sequence.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably if referring to nucleic acid sequences) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are identical at this position. The percentage identity between the two sequences is a function of the number of identical positions shared by the sequences (i.e. % identity=number of identical positions/total number of positions×100). The terms "homology" and "identity" are thus to be considered as synonyms when referring to nucleic acid sequences. When referring to amino acid sequences the term identity refers to identical amino acids at a specific position in a sequence, the term homology refers to homologous amino acids at a specific position in a sequence. Homologous amino acids are amino acids having a similar side chain. Families of amino acid residues having similar side chains have been defined in the art.

A nucleic acid molecule encoding a protein homologous to a protein of the invention can be created by introducing one or more nucleotide substitutions, additions or deletions into a nucleotide sequence such that one or more amino acid substitutions, additions or deletions are introduced into the encoded protein. Mutations can be introduced into one of the sequences of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a protein of the invention is preferably replaced with another amino acid residue from the same side chain family.

Alternatively, in another embodiment, mutations can be introduced randomly along all or part of a coding sequence, such as by saturation mutagenesis, and the resultant mutants can be screened for the respective activity described herein to identify mutants that retain their activity. Following mutagenesis of one of the sequences of the invention, the encoded protein can be expressed recombinantly and the activity of the protein can be determined using, for example, assays described herein.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -l Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the identity is calculated on the complete length of the query sequence, for example SEQ ID NO:1.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and antisense strands (i.e., the nucleic acid sequence may be double-stranded).

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. The term also comprises nucleic acid molecules which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or -5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the latter being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used inter-changeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, alanine) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e. g., when the genetic modification affects coding nucleic acid sequences of the microorganism) as compared to the wild type microorganism from which it was derived. A recombinant microorganism comprises at least one recombinant DNA molecule.

The term "recombinant" with respect to DNA refers to DNA molecules produced by man using recombinant DNA techniques. The term comprises DNA molecules which as such do not exist in nature or do not exist in the organism from which the DNA is derived, but are modified, changed, mutated or otherwise manipulated by man. Preferably, a "recombinant DNA molecule" is a non-naturally occurring nucleic acid molecule that differs in sequence from a naturally occurring nucleic acid molecule by at least one nucleic acid. A "recombinant DNA molecule" may also comprise a "recombinant construct" which comprises, preferably operably linked, a sequence of nucleic acid molecules not naturally occurring in that order. Preferred methods for producing said recombinant DNA molecule may comprise cloning techniques, directed or non-directed mutagenesis, gene synthesis or recombination techniques.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

An example of such a recombinant DNA is a plasmid into which a heterologous DNA-sequence has been inserted or a gene or promoter which has been mutated compared to gene or promoter from which the recombinant DNA derived. The mutation may be introduced by means of directed mutagenesis technologies known in the art or by random mutagenesis technologies such as chemical, UV light or x-ray mutagenesis or directed evolution technologies.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

Figure 1:
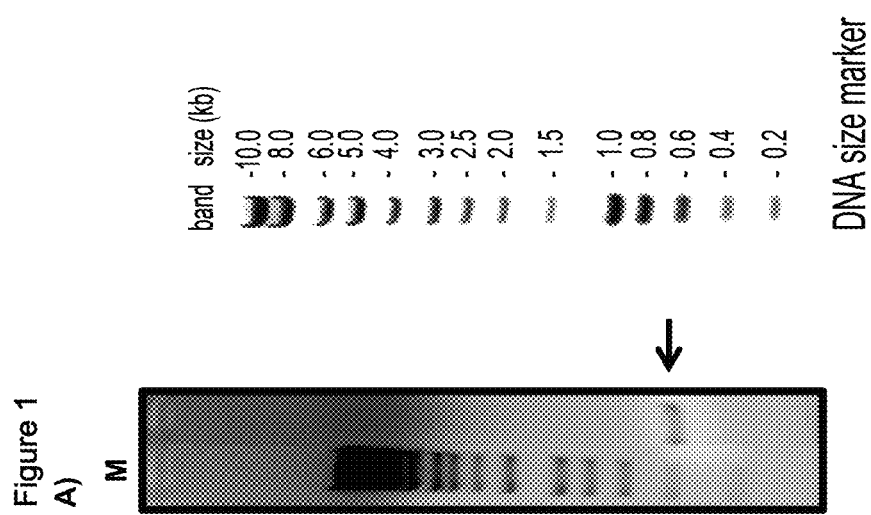
FIGS. 1A and 1B

Clone validation after inactivation of the ackA-pta genes.

FIG. 1A: PCR amplicon obtained from genomic DNA of *E. coli* W ΔackA-pta::FRT with primers P395-ackA-pta-check2 and P395-ackA-pta-check5 (338 bp). M: DNA size marker. FIG. 1B: Sequencing of the PCR amplicon with P395-ackA-pta-check2 and P395-ackA-pta-check5 confirmed basepair-precise modification of the ackA-pta locus. Nucleotides that were confirmed by sequencing are shown in italics. The remaining FRT site is shown in green, flanking primer binding sites are shown in red. upper case: coding sequence. lower case: intergenic regions (nucleotide sequence: SEQ ID NO: 115, protein sequence: SEQ ID NO: 123).

FIGS. 2A and 2B

Clone validation after inactivation of the adhE gene.

FIG. 2A: PCR amplicon obtained from genomic DNA of *E. coli* W ΔackA-pta::FRT ΔadhE::FRT with primers P395-adhE-check2 and P395-adhE-check5 (569 bp). M: DNA size marker. FIG. 2B: Sequencing of the PCR amplicon with P395-adhE-check2 and P395-adhE-check5 con-firmed basepair-precise modification of the adhE locus. Nucleotides that were confirmed by sequencing are shown in italics. The remaining FRT site is shown in green, flanking primer binding sites are shown in red. upper case: coding sequence. lower case: intergenic regions (nucleotide sequence: SEQ ID NO: 116, protein sequence: SEQ ID NO: 124).

FIGS. 3A and 3B

Clone validation after inactivation of the frdABCD genes.

FIG. 3A: PCR amplicon obtained from genomic DNA of *E. coli* W ΔackA-pta::FRT ΔadhE::FRT ΔfrdABCD::FRT with primers P395-frd-check1 and P395-frd-check4 (797 bp). M: DNA size marker. FIG. 3B: Sequencing of the PCR amplicon with P395-frd-check1 and P395-frd-check4 confirmed basepair-precise modification of the frd locus. Nucleotides that were confirmed by sequencing are shown in italics. The remaining FRT site is shown in green, flanking pri-mer binding sites are shown in red. upper case: coding sequence. lower case: intergenic regions (nucleotide sequence: SEQ ID NO: 117, protein sequence: SEQ ID NO: 125).

FIGS. 4A and 4B

Clone validation after inactivation of the pflB gene.

FIG. 4A: PCR amplicon obtained from genomic DNA of *E. coli* W ΔackA-pta::FRT ΔadhE::FRT ΔfrdABCD::FRT ΔpflB::FRT with primers P395-pflB-check1 and P395-pflB-check3 (511 bp). M: DNA size marker. FIG. 4B: Sequencing of the PCR amplicon with P395-pflB-check1 and P395-pflB-check3 confirmed basepair-precise modification of the pflB locus. Nucleotides that were confirmed by sequencing are shown in italics. The remaining FRT site is shown in green, flanking primer binding sites are shown in red. upper case: coding sequence. lower case: intergenic regions (nucleotide sequence: SEQ ID NO: 118, protein sequence: SEQ ID NO: 126).

FIGS. 5A and 5B

Clone validation after integration of the alaD-gstear gene.

FIG. 5A: PCR amplicon obtained from genomic DNA of *E. coli* W ΔackA-pta::FRT ΔadhE::FRT ΔfrdABCD::FRT ΔpflB::FRT ΔldhA::alaD-gstear with primers P395-ldhA-check1 and P395-ldhA-check2 (1833 bp). M: DNA size marker. FIG. 5B: Sequencing of the PCR amplicon with P395-ldhA-check1 and P395-ldhA-check2 confirmed basepair-precise modification of the ldhA locus and integration of alaD-gstear. Nucleotides that were confirmed by sequencing are shown in italics. The alaD-gstear ORF is shown in cyan, the remaining FRT site is shown in green, flanking primer binding sites are shown in red. upper case: coding sequence. lower case: intergenic regions (nucleotide sequence: SEQ ID NO: 119, protein sequence: SEQ ID NO: 16).

FIG. 6

Biosynthesis route of alanine in *E. coli* strain Ex1 (interchangeably named QZ16), which is comprising all mutations as described in Example 1.

FIG. 7

Genomic organization of the new locus at the insertion site of alaD gene in stem Ev3 (interchangeably named QZ20) comprising a partial deletion of the ydbH coding region and deletion of the ldhA promoter (which was driving expression of the alaD gene in stem QZ16) (Ex1: SEQ ID NO: 120; Ex2: SEQ ID NO: 121; and Ex3: SEQ ID NO: 122).

FIG. 8

SDS-PAGE analysis of soluble protein fractions of *E. coli* W, *E. coli* QZ16, *E. coli* QZ20, and *E. coli* QZ32 grown over night in LB medium at 37 C. The 39.37 kDa alanine dehydrogenase (AlaD) band is framed in white. *E. coli* cultures were normalized to OD600 before cells were lysed. M: Marker

FIG. 9

Volumetric alanine dehydrognease (alaD) activity was monitored in an in vitro assay with *E. coli* crude cell lysates. The conversion of L-alanine to pyruvate was monitored spectrophotometrically via the formation of NADH at 340 nm.

FIG. 10

Relative gene expression analysis of alaD in *E. coli* QZ16 and QZ20 at 8 h, 11 h and 28 during batch-fermentation relative to *E. coli* QZ16 8 h. All qPCR-derived data were normalized versus the rrsA gene as reference.

FIG. 11

Batch fermentation of *E. coli* QZ16, *E. coli* QZ32 and *E. coli* QZ63 in 500 mL NBS medium with 80 g/L glucose. The fermentation was controlled at 37 C, 400 rpm, at pH 6.8 with 5 N $NH_4OH$ without aeration. The graph depicts the formation of alanine correlated from alanine concentrations of samples and $NH_4OH$ consumption rate.

FIG. 12

The volumetric alanine productivity (space-time-yield), defined as the amount of product generated divided by reactor volume and by time, of *E. coli* QZ16 (over 50 h) and QZ32 (ΔydbH-lpdA) and QZ63 (ΔlpdA) until full glucose consumption was reached during batch-fermentation in 500 mL NBS medium with 80 g/L glucose as carbon source.

FIG. 13

Batch fermentation of *E. coli* QZ33 (ΔydbH-lpdA, ygaW Q5H) and *E. coli* QZ32 (ΔydbH-lpdA) in 500 mL NBS medium with 80 g/L glucose. The fermentation was controlled at 37 C, 400 rpm, at pH 6.8 with 5 N NH4OH without aeration. The graph depicts the formation of alanine correlated from alanine concentrations of samples and $NH_4OH$ consumption rate.

FIG. 14

The volumetric alanine productivity (space-time-yield), defined as the amount of product generated divided by reactor volume and by time, of *E. coli* QZ32 (ΔydbH-ldhA), QZ60 (ΔydbH-ldhA, ygaW Q5N), QZ61 (ΔydbH-ldhA, ygaW Q5R), QZ62 (ΔydbH-ldhA, ygaW Q5Y) and QZ33 (ΔydbH-ldhA, ygaW Q5H), until full glucose consumption was reached during batch fermentation in 500 mL NBS medium with 80 g/L glucose as carbon source.

FIG. 15

Batch fermentation of *E. coli* QZ60 (ΔydbH-lpdA, ygaW Q5N), *E. coli* QZ61 (ΔydbH-lpdA, ygaW Q5R) and *E. coli* QZ62 (ΔydbH-lpdA, ygaW Q5Y) compared with *E. coli* QZ32 (ΔydbH-lpdA) and *E. coli* QZ33 (ΔydbH-lpdA, ygaW Q5H) in 500 mL NBS medium with 80 g/L glucose. The fermentation was controlled at 37 C, 400 rpm, at pH 6.8 with 5 N NH4OH without aeration. (A) depicts the biomass formation throughout the fermentation. (B) depicts the formation of alanine correlated from alanine concentrations of samples and NH4OH consumption rate.

FIG. 16

Relative gene expression analysis of ygaW in *E. coli* QZ16 and QZ20 at 8 h, 11 h and 28 of batch-fermentation in relation to *E. coli* QZ16 8 h as determined by RT-qPCR. All qPCR-derived data were normalized versus the rrsA gene as reference.

FIG. 17

Batch fermentation of *E. coli* QZ41 (ΔydbH-ldhA, ygaW Q5H, zipA SNP) and *E. coli* QZ33 (ΔydbH-ldhA, ygaW Q5H) in 500 mL NBS medium with 80 g/L glucose. The fermentation was controlled at 37 C, 400 rpm, at pH 6.8 with 5 N NH4OH without aeration. The graph depicts the formation of alanine correlated from alanine concentrations of samples and NH4OH consumption rate.

FIG. 18

The volumetric alanine productivity (space-time-yield), defined as the amount of product generated divided by reactor volume and by time, of *E. coli* QZ33 (ΔydbH-ldhA, ygaW Q5H) and QZ 41 (ΔydbH-ldhA, ygaW Q5H, zipA SNP) until full glucose consumption during batch-fermentation in 500 mL NBS medium with 80 g/L glucose as carbon source.

FIG. 19

Batch fermentation of *E. coli* QZ52 (ΔydbH-ldhA, ygaW Q5H, lpd SNP) and *E. coli* QZ33 (ΔydbH-ldhA, ygaW Q5H) in 500 mL NBS medium with 100 g/L glucose. The fermentation was controlled at 37 C, 400 rpm, at pH 6.8 with 5 N NH4OH without aeration. (A) depicts the biomass formation of both strains throughout the fermentation. (B) depicts the formation of alanine correlated from alanine concentrations of samples and NH4OH consumption rate.

FIG. 20

The volumetric alanine productivity (space-time-yield), defined as the amount of product generated divided by reactor volume and by time, of *E. coli* QZ33 (ΔydbH-ldhA, ygaW Q5H) and QZ52 (ΔydbH-ldhA, ygaW Q5H, lpd SNP) after 41 h of batch-fermentation in 500 mL NBS medium with 100 g/L glucose as carbon source. While QZ53 had fully consumed all glucose after 41 h, QZ33 was not able to fully consume the glucose under the tested conditions up to 53 h.

FIG. 21

The volumetric alanine productivity (space-time-yield), defined as the amount of product generated divided by reactor volume and by time, of *E. coli* QZ32 (ΔydbH-ldhA), QZ33 (ΔydbH-ldhA, ygaW Q5H), QZ41 (ΔydbH-ldhA, ygaW Q5H, zipA SNP) and QZ53 (ΔydbH-ldhA, ygaW Q5H, zipA SNP, lpd SNP) until full glucose consumption was reached during batch fermentation in 500 mL NBS medium with 80 g/L glucose as carbon source.

FIG. 22

Batch fermentation of *E. coli* QZ53 (ΔydbH-ldhA, ygaW Q5H, zipA SNP, lpd SNP) and *E. coli* QZ41 (ΔydbH-ldhA, ygaW Q5H, zipA SNP) in 500 mL NBS medium with 100 g/L glucose. The fermentation was controlled at 37 C, 400 rpm, at pH 6.8 with 5 N NH4OH without aeration. The graph depicts the formation of alanine titer correlated from alanine concentrations of samples and NH4OH consumption rate.

FIG. 23

The volumetric alanine productivity (space-time-yield), defined as the amount of product generated divided by reactor volume and by time, of *E. coli* QZ53 (ΔydbH-ldhA, ygaW Q5H, zipA SNP, lpd SNP) and QZ41 (ΔydbH-ldhA, ygaW Q5H, zipA SNP) until full glucose consumption during batch-fermentation in 500 mL NBS medium with 80 g/L glucose as carbon source was reached.

FIG. 24

Batch fermentation of *E. coli* QZ33 (ΔydbH-ldhA, ygaW Q5H) with control plasmid pACYC184 and *E. coli* QZ33 with plasmid pACYC184-lpd with an additional copy of the lpd ORF in 500 mL NBS medium with 80 g/L glucose. The fermentation was controlled at 37 C, 400 rpm, at pH 6.8 with 5 N NH4OH without aeration. The graph depicts the formation of alanine titer correlated from alanine concentrations of samples and NH4OH consumption rate.

FIG. 25

The volumetric alanine productivity (space-time-yield), defined as the amount of product generated divided by reactor volume and by time, of *E. coli* QZ33 (ΔydbH-ldhA, ygaW Q5H) with control plasmid pACYC184 and *E. coli* QZ33 with plasmid pACYC184-lpd with an additional copy of the lpd ORF until full glucose consumption during batch-fermentation in 500 mL NBS medium with 80 g/L glucose as carbon source was reached.

EXAMPLES

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells are performed as described (Sambrook et al., 1989). Sequence analyses of recombinant DNA are performed with a laser fluorescence DNA sequencer (Applied Biosystems, Foster City, Calif., USA) using the Sanger technology (Sanger et al., 1977). Unless described otherwise, chemicals and reagents are obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases are from New England Biolabs (Ipswich, Mass., USA) or Roche Diagnostics GmbH (Penzberg, Germany). Oligonucleotides are synthesized by Eurofins MWG Operon (Ebersberg, Germany).

Example 1

*E. coli* W (LU17032) was engineered for L-alanine production by inactivation of the ackA-pta, adhE, frdABCD and pflB ORFs and replacement of the ldhA ORF by a codon-optimized variant of the alaD gene (alaD-gstear).

The ackA-pta, adhE, frdABCD and pflB ORFs were inactivated by insertion of an FRT-flanked kanamycin resistance cassette, followed by removal of the antibiotic resistance cassette by FLP recombination.

The ldhA gene was replaced by alaD-gstear and a downstream FRT-flanked zeocin resistance cassette, which was finally removed by FLP recombination.

Materials and Methods

Bacterial Culture

*E. coli* W (LU17032) was cultured in Luria-Bertani (LB) liquid medium or on Luria-Bertani solid medium. Occasionally, clones were passaged over M9 minimal agar containing 10 mM Sucrose to confirm W strain identity. Antibiotics were added to the liquid and solid media as appropriate, to final concentrations of 15 µg/ml (kanamycin, chloramphenicol), 25 µg/ml (zeocin) or 3 µg/ml (tetracyclin).

Red/ET Recombination

Red/ET recombination was performed using standard protocols of Gene Bridges GmbH (www.genebridges.com). Briefly, Red/ET-proficient *E. coli* W was aerobically grown at 30° C. to an OD600 nm of ~0.3. Expression of red genes was induced by adding 50 µl of 10% (w/v) L-arabinose, followed by a temperature increase to 37° C. Arabinose was omitted from uninduced control cultures. After 35 min of incubation at 37° C. the cells were washed twice with ice cold 10% (v/v) glycerol and electroporated with 500 ng of PCR product at 1.35 kV, 10 µF, 600Ω. The cells were then resuspended in 1 ml ice-cold LB medium and aerobically grown at 37° C. for approximately 1.5 h. Cultures were then plated on LB agar containing 15 µg/ml kanamycin (knockouts) or 25 µg/ml zeocin (knockin).

FLP Recombination

Flanking FRT sites allowed removal of antibiotic resistance markers by FLP recombination following modification of the E. coli chromosome. FLP recombination leaves a single FRT site (34 bp) as well as short flanking sequences (approx. 20 bp each) which are used as primer binding sites in the amplification of the cassettes.

To perform FLP recombination, plasmid 708-FLPe (Tab. 1) encoding FLP recombinase was introduced into the Red/ET recombinants by electroporation. KanR CmR or ZeoR CmR transformants were used to inoculate 0.2 ml LB cultures, which were incubated at 30° C. for 3 h. FLP activity was then induced by a temperature shift to 37° C., followed by a three-hour incubation at 37° C. Single colonies obtained from these cultures were subsequently screened for a CmS and KanS or ZeoS phenotype.

DNA Preparation and Analysis

E. coli genomic DNA (gDNA) was isolated from overnight cultures with the Gentra Puregene Yeast/Bact. Kit B (Qiagen, Hilden, Germany). PCR products harbouring knockout or knockin cassettes were amplified from template plasmids with PRECISOR high-fidelity DNA polymerase (BioCat, Heidelberg) and analytical PCR reactions were performed with the PCR Extender System (5PRIME GmbH, Hamburg, Germany), according to the manufacturer's recommendations. PCR amplicons were purified using the GeneJET PCR Purification Kit or the GeneJET Gel Extraction Kit (Fermentas, St. Leon-Rot, Germany) and sequencing was performed by GATC BioTech (Konstanz, Germany) or BioSpring (Frankfurt am Main, Germany).

TABLE 1

Plasmids and primers

| plasmids | Relevant characteristics/ oligo sequences (5'→3') | Source |
|---|---|---|
| pRed/ET | red expression plasmid, pSC101-based, Tc$^R$ | Gene Bridges |
| 708-FLPe | FLP recombinase expression plasmid, pSC101-based, Cm$^R$ | Gene Bridges |
| pQZ11 | puC57-based plasmid with chloramphenicol acetyltransferase (cat)-levansucrase (sacB) cassette, ampR | Genescript |
| pACYC184 | E. coli cloning vector, p15A ori Cm$^R$, TC$^R$ | NEB |
| pACYC184-Ipd | Ipd ORF expression plamid, p15A ori, Cm$^R$ | in house |
| primers (BioSpring) | Sequence | SEQ ID NO |
| P395-ackA-pta-check1 | 5'-ACTGCGGTAGTTCTTCACTG-3' | SEQ ID NO: 17 |
| P395-ackA-pta-check2 | 5'-AGTACCTTTCTGGTTTAGCCG-3' | SEQ ID NO: 18 |
| P395-ackA-pta-check3 | 5'-GATAGCAGAAACGGAACCAC-3' | SEQ ID NO: 19 |
| P395-ackA-pta-check4 | 5'-GGTGCTGTTCACACTACCGC-3' | SEQ ID NO: 20 |
| P395-ackA-pta-check5 | 5'-TGACGAGATTACTGCTGCTG-3' | SEQ ID NO: 21 |
| P395-ackA-pta-check6 | 5'-ATTTCCGGTTCAGATATCCGC-3' | SEQ ID NO: 22 |
| P395-adhE-check1 | 5'-GGGTTGACCAGCGCAAATAAC-3' | SEQ ID NO: 23 |
| P395-adhE-check2 | 5'-CAGAAGTGAGTAATCTTGCTTAC-3' | SEQ ID NO: 24 |
| P395-adhE-check3 | 5'-GATCACTTTATCTTCGACGATAC-3' | SEQ ID NO: 25 |
| P395-adhE-check4 | 5'-GCGAACGTGGATAAACTGTCTG-3' | SEQ ID NO: 26 |
| P395-adhE-check5 | 5'-GCTCTTAAGCACCGACGTTGAC-3' | SEQ ID NO: 27 |
| P395-adhE-check6 | 5'-GTCGGCTCATTAACGGCTATTC-3' | SEQ ID NO: 28 |
| P395-frd-check1 | 5'-GACGGATCTCCGCCATAATC-3' | SEQ ID NO: 29 |
| P395-frd-check2 | 5'-TCGCCACCCGCTACTGTATC-3' | SEQ ID NO: 30 |
| P395-frd-check3 | 5'-CAAAGCGTTCTGACGAACCGG-3' | SEQ ID NO: 31 |
| P395-frd-check4 | 5'-TGTGCGATGCACAATATCGTTG-3' | SEQ ID NO: 32 |
| P395-pflB-check1 | 5'-TTGGTTGGGTTGACATACTGG-3' | SEQ ID NO: 33 |

TABLE 1-continued

Plasmids and primers

| | | |
|---|---|---|
| P395-pflB-check2 | 5'-TGAACTTCATCACTGATAACC-3' | SEQ ID NO: 34 |
| P395-pflB-check3 | 5'-TTCAAAGGAGTGAATGCGACC-3' | SEQ ID NO: 35 |
| P395-pflB-check4 | 5'-GTCGCGGTTATGACAATACAGG-3' | SEQ ID NO: 36 |
| P395-ldhA-check1 | 5'-TACCGTGCCGACGTTCAATAAC-3' | SEQ ID NO: 37 |
| P395-ldhA-check2 | 5'-CATCAGCAGGCTTAGCGCAAC-3' | SEQ ID NO: 38 |
| P395-ldhA-check3 | 5'-ACCTTTACGCGTAATGCGTG-3' | SEQ ID NO: 39 |
| P395-ldhA-check4 | 5'-ACCGTTTACGCTTTCCAGCAC-3' | SEQ ID NO: 40 |
| P395-csc-check1 | 5'-CGAATTATCGATCTCGCTCAAC-3' | SEQ ID NO: 41 |
| P395-csc-check2 | 5'-CGTCTATATTGCTGAAGGTACAG-3' | SEQ ID NO: 42 |
| P395-csc-check3 | 5'-TCGAAGGTCCATTCACGCAAC-3' | SEQ ID NO: 43 |
| P395-csc-check4 | 5'-GATTCCCACCGCAACGTTAG-3' | SEQ ID NO: 44 |
| Rec1_1_F | GTTTTCCCTGCCATTCCTGCCAGGG AGAAAAAATCAGTTTATCGATATTGA TGATATCGGAAGCCCTGGGCCAAC | SEQ ID NO: 62 SEQ ID NO: 63 |
| Rec1_1_R | CTTTCTCCAGTGATGTTGAATCACA TTTAAGCTACTAAAAATATTTTACAA ACACCTGAGACAACTTGTTACAGCTC | SEQ ID NO: 64 |
| Rec1_2_F | GTTTTCCCTGCCATTCCTGCCAGGG AGAAAAAATCAGTTTATCGATATTGAT TTTGTAAAATATTTTTAGTAGC | |
| Rec1_2_R | ATTTTCATAAGACTTTCTCCAGTGATG TTGAATCACATTTAAGCTACTAAAAATA TTTTACAAAATCAATATCG | SEQ ID NO: 65 |
| Rec1_seq_F | ACGCGACGACATCCAGTTCG | SEQ ID NO: 66 |
| Rec1_seq_R | CCGGCACCCGCTTCGGTTTCG | SEQ ID NO: 67 |
| Rec1B_1_F | ATTGTGGCATGTTTAACCGTTCAGTT GAAGGTTGCGCCTACACTAAGCATG ATATCGGAAGCCCTGGGCCAAC | SEQ ID NO: 68 |
| B1R_1_R | TTCAAATATAATTGAAAGCTATGGCG ATATTGAAAAATTCATCAACAACTCA CCTGAGACAACTTGTTACAGCTC | SEQ ID NO: 69 |
| Rec1B_2_F | CATTCAATACGGGTATTGTGGCATG TTTAACCGTTCAGTTGAAGGTTGCG CCTACACTAAGCATTATTGATTTTG | SEQ ID NO: 70 |
| Rec1B_2_R | GACTTTCTCCAGTGATGTTGAATCAC ATTTAAGCTACTAAAAATATTTTACAA AATCAATAATGCTTAGTGTAGG | SEQ ID NO: 71 |
| Rec1B_seq_F | ATAATCAGTAATAACAGCGCGAG | SEQ ID NO: 72 |
| Rec1B_seq_R | CCGGCACCCGCTTCGGTTTCG | SEQ ID NO: 73 |
| Rec1C_1_F | CACCAGCGGCTGGAATACAGTCAG TGATTGTTTTGGCCACCAGGCGTTA CCGCGATATCGGAAGCCCTGGGCCAAC | SEQ ID NO: 74 |
| Rec1C_1_R | GGTGAGATTGGCCCGGTTCGGGTA AATGGTCGCTGGGACGGTATTCGTC TGCCACCTGAGACAACTTGTTACAGCTC | SEQ ID NO: 75 |
| Rec1C_2_F | GGCGTACAGGCAGCCAGCATAAAAG ATGACGTCAACGCAGCCAGTAAAATT TGGGTAGTTAATATCCTGATTTAGCG | SEQ ID NO: 76 |
| Rec1C_2_R | CAATACCCGTATTGAATGCTTAATTTT TCGCTAAATCAGGATATTAACTACC CAAATTTTACTGGCTGCGTTGACGTC | SEQ ID NO: 77 |

TABLE 1-continued

Plasmids and primers

| | | |
|---|---|---|
| Rec1C_seq_F | CGTTCATATTGATAGTGATCGGTTCCTTGG | SEQ ID NO: 78 |
| Rec1C_seq_R | CATCAACAACTATGCTTAGTGTAGGCGCAA | SEQ ID NO: 79 |
| Rec2_1_F | GTTTTCATCTCCATTAACATCCCAT<br>TACGCTTTTATTAAGGAGCATTAGC<br>GATATCGGAAGCCCTGGGCCAAC | SEQ ID NO: 80 |
| Rec2_1_R | ATGTTCACGACAGAACAGTAAACAA<br>CCATCGCGAACGTATCTGCAACTGC<br>CACCTGAGACAACTTGTTACAGCTC | SEQ ID NO: 81<br>SEQ ID NO: 82 |
| ReC2_2_F | GTTTTCATCTCCATTAACATCCCATT<br>ACGCTTTTATTAAGGAGCATTAGCAT<br>GTTCTCACCGCATTCACGCTTGC | |
| ReC2_2_R | ATGTTCACGACAGAACAGTAAACAA<br>CCATCGCGAACGTATCTGCAACTGC<br>ATGACGCAAGCGTGAATGCGGTGAG | SEQ ID NO: 83 |
| Rec2_seq_F | CAAAAAACGAGCCGTTACGG | SEQ ID NO: 84 |
| Rec2_seq_R | GACGGGCTAACTTTGCGTGC | SEQ ID NO: 85 |
| Rec3_seq_F | CAGGTCGTGGTACTTGGGGC | SEQ ID NO: 86 |
| Rec3B_seq_R | GTCTGACATTCGCCGTCTGG | SEQ ID NO: 87 |
| Rec3B_1_F | GGCCGGCTTTTTTCTGGTAATCTCA<br>TGAATGTATTGAGGTTATTAGCGAA<br>GATATCGGAAGCCCTGGGCCAAC | SEQ ID NO: 88 |
| Rec3B_1_R | TACAAAATTGTTAACAATTTTTAAAC<br>AACAAACGGCAACCGATTTGTCTAC<br>ACCTGAGACAACTTGTTACAGCTC | SEQ ID NO: 89 |
| Rec3B_2_F | GAATGTATTGAGGTTATTAGCG | SEQ ID NO: 90 |
| Rec3B_2_R | ACGAATCTTGTCAATATCGG | SEQ ID NO: 91 |
| Rec4_seq_F | TCGTCATCTTAGCCCGGATG | SEQ ID NO: 92 |
| Rec4_seq_R | TGATGGCGAAGCGTCGTTCG | SEQ ID NO: 93 |
| Rec4B_1_F | TGCGCGAGTACCAGGACATCATC<br>CGCGAAGTCAAAGACGCCAACG<br>CCTGAGATATCGGAAGCCCTGGGCCAAC | SEQ ID NO: 94 |
| Rec4B_1_R | AACCCCCGACAAGCGGGGGTTCGA<br>AGAGGAGTTAAATTTGCCTTAAGTGTA<br>CACCTGAGACAACTTGTTACAGCTC | SEQ ID NO: 95 |
| Rec4B_2_F | AAGCTGATGCTGCAATCTGC | SEQ ID NO: 96 |
| Rec4B_2_R | GCTAAAAACCCCCGACAAGC | SEQ ID NO: 97 |
| ygaW Q5N | GTTTTCATCTCCATTAACATCCCAT<br>TACGCTTTTATTAAGGAGCATTAGC<br>atgTTCTCACCGaacTCACGCTTGCG<br>TCATGCAGTTGCAGATACGTTCGCG<br>ATGGTTGTTTACTGTTCTGTCGTGAACAT | SEQ ID NO: 98 |
| ygaW Q5R | GTTTTCATCTCCATTAACATCCCATT<br>ACGCTTTTATTAAGGAGCATTAGCatg<br>TTCTCACCGcgtTCACGCTTGCGTCAT<br>GCAGTTGCAGATACGTTCGCGATGG<br>TTGTTTACTGTTCTGTCGTGAACAT | SEQ ID NO: 99 |
| ygaW Q5Y | GTTTTCATCTCCATTAACATCCCATTA<br>CGCTTTTATTAAGGAGCATTAGCatgTT<br>CTCACCGtatTCACGCTTGCGTCATGC<br>AGTTGCAGATACGTTCGCGATGGTTG<br>TTTACTGTTCTGTCGTGAACAT | SEQ ID NO: 100 |
| IdhA_RT_F | CAAGAAGTACCTGCAACAGGTGAACG | SEQ ID NO: 101 |
| IdhA_RT_R | ATACCGCTTCGCAGCCATTGG | SEQ ID NO: 102 |

TABLE 1-continued

Plasmids and primers

| alaD_RT_F | TGCGGTTATTGTGACTAAGGCG | SEQ ID NO: 103 |
| --- | --- | --- |
| alaD_RT_R | GTGAACAAAATCAGACCCGG | SEQ ID NO: 104 |
| ygaW_RT_F | GCGATGGTTGTTTACTGTTCTGTCG | SEQ ID NO: 105 |
| ygaW_RT_R | CCGGAATCGCTACCAATCTGG | SEQ ID NO: 106 |
| lpd_RT_F | TTACTCCGCTGCCTTCCGTTGC | SEQ ID NO: 107 |
| lpd_RT_R | AGGGATACAGCCGACGTTCAGG | SEQ ID NO: 108 |
| zipA_RT_F | GCCATAATCGCTTTACTGGTACATGG | SEQ ID NO: 109 |
| zipA_RT_R | TCGTCACGTTTTGACTTCATTCG | SEQ ID NO: 110 |
| rrsA_RT_F | CTCTTGCCATCGGATGTGCCCAG | SEQ ID NO: 111 |
| rrsA_RT_R | CCAGTGTGGCTGGTCATCCTCTCA | SEQ ID NO: 112 |
| lpd-pACYC_F | TATCATCGATAAGCTTCTCATGAAT GTATTGAGGTTATTAGCG | SEQ ID NO: 113 |
| lpd-pACYC_R | AAGGGCATCGGTCGACGGCGACA GGAAAGGTAAATTGC | SEQ ID NO: 114 |

1.1. ackA-pta Locus—Targeting of ackA-Pta

Approximately 500 ng of the ΔackA-pta PCR construct (1737 bp) were electroporated into Red/ET-proficient *E. coli* W cells. Eight KanR transformants were analysed for correct integration of the resistance marker cassette by PCR with genome-specific primers. Three clones were subjected to FLP recombination, which was performed as described in Material and Methods (data not shown).

Clone validation. Inactivation of the ackA-pta locus and removal of the kanamycin resistance cassette were confirmed by PCR across the remaining FRT scar. One clone that yielded the correct PCR signal was also confirmed by sequencing (FIG. 1).

1.2 adhE Locus—Targeting of adhE

Approximately 500 ng of the ΔadhE PCR construct (1093 bp) were electroporated into Red/ET-proficient *E. coli* W cells harbouring the ΔackA-pta::FRT modification. Eight KanR transformants were analysed for correct integration of the resistance marker cassette by PCR with genome-specific primers. Two clones were subjected to FLP recombination, which was performed as described in Material and Methods (data not shown).

Figure 2:
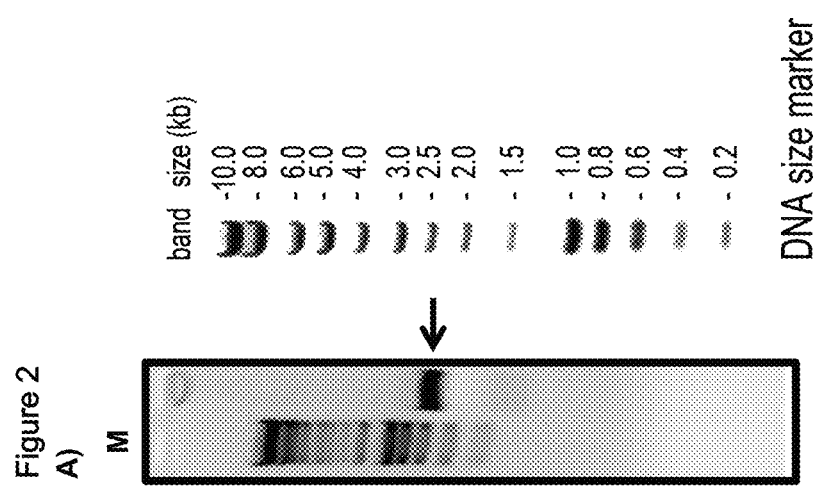

Clone validation. Inactivation of the adhE locus and removal of the kanamycin resistance cassette were confirmed by PCR across the remaining FRT scar. One clone that yielded the correct PCR signal was also confirmed by sequencing (FIG. 2).

1.3 Frd Locus—Targeting of frdABCD

Approximately 500 ng of the ΔfrdABCD PCR construct (1093 bp) were electroporated into Red/ET-proficient *E. coli* W cells harbouring the ΔackA-pta::FRT and ΔadhE::FRT modifications. Eight KanR transformants were analysed for correct integration of the resistance marker cassette by PCR with genome-specific primers. One clone was subjected to FLP recombination, which was performed as described in material and Methods (data not shown).

Figure 3:
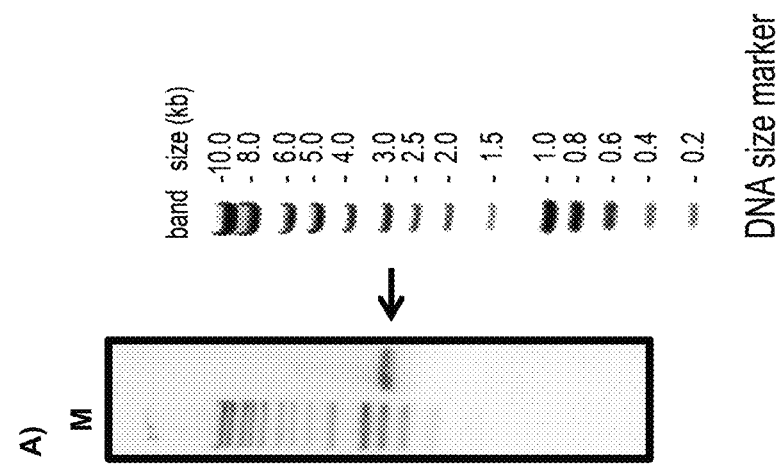

Clone validation. Inactivation of the frd locus and removal of the kanamycin resistance cassette were confirmed by PCR across the remaining FRT scar. One clone that yielded the correct PCR signal was also confirmed by sequencing (FIG. 3).

1.4 pflB Locus—Targeting of pflB

Approximately 500 ng of the ΔpflB PCR construct (1093 bp) were electroporated into Red/ET-proficient *E. coli* W cells harbouring the ΔackA-pta::FRT, ΔadhE::FRT and ΔfrdABCD::FRT modifications. Eight KanR transformants were analysed for correct integration of the resistance marker cassette by PCR with genome-specific primers. Four clones were subjected to FLP recombination, which was performed as described in Material and Methods (data not shown).

Figure 4:
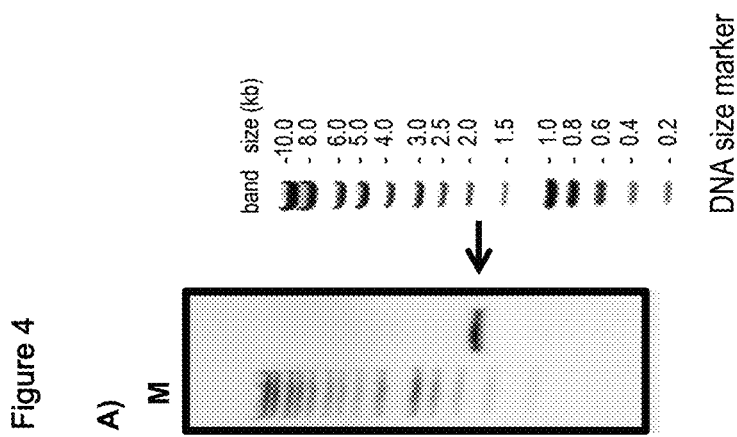

Clone validation. Inactivation of the pflB locus and removal of the kanamycin resistance cassette were confirmed by PCR across the remaining FRT scar. One clone that yielded the correct PCR signal was also confirmed by sequencing (FIG. 4).

1.5 ldhA Locus—Knockin of alaD-gstear

Approximately 500 ng of the ΔldhA::alaD-gstear PCR construct (1783 bp) were electroporated into Red/ET-proficient *E. coli* W cells harbouring the ΔackA-pta::FRT, ΔadhE::FRT, ΔfrdABCD::FRT and ΔpflB::FRT modifications. Four ZeoR transformants were analysed for correct integration of the resistance marker cassette by PCR with genome-specific primers. One clone was subjected to FLP recombination, which was performed as described in material and Methods (data not shown).

Figure 5:
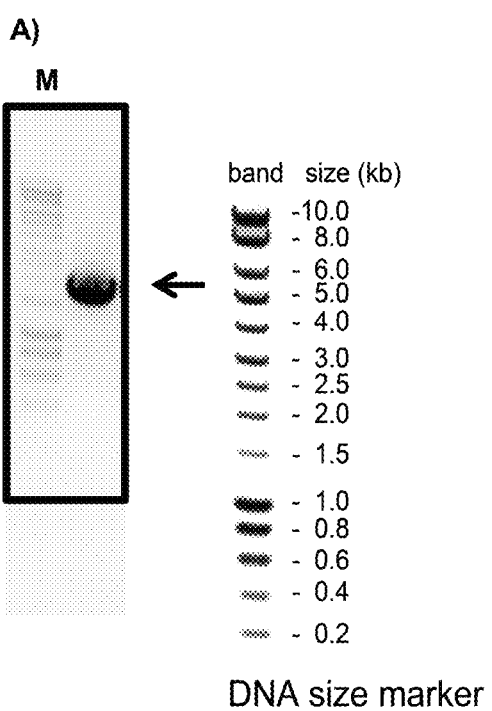
Figure 6:
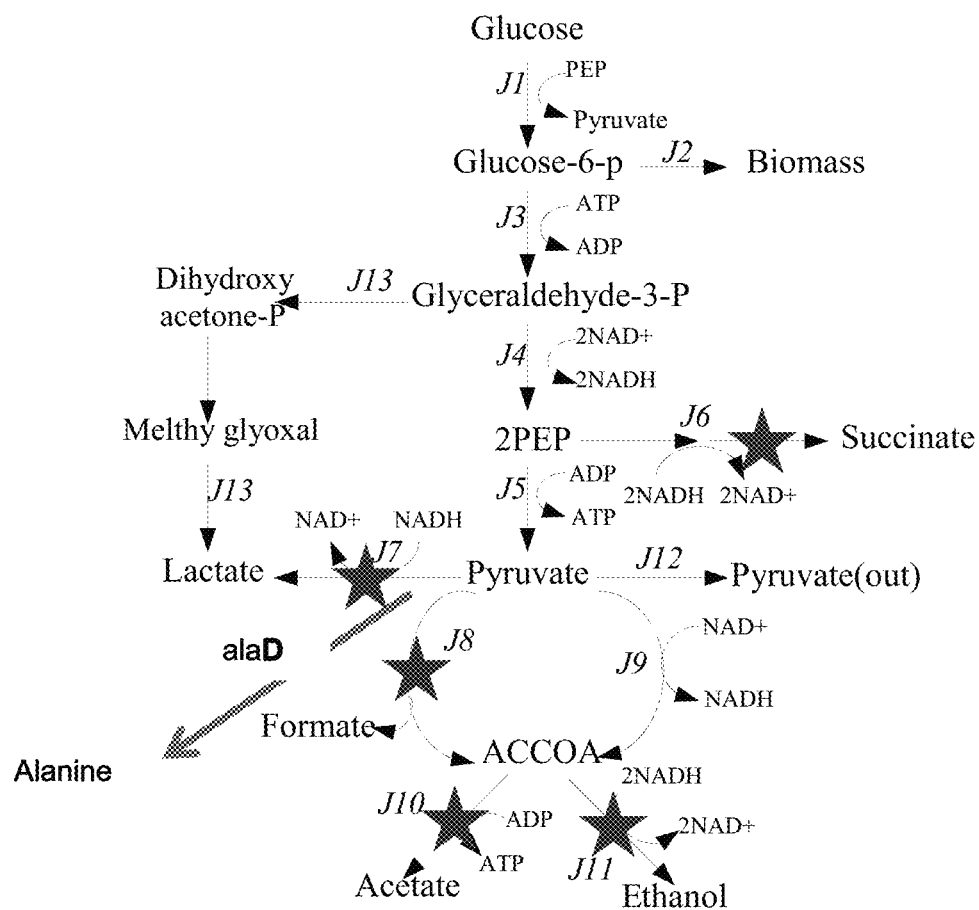

Clone validation. Integration of alaD-gstear and removal of the zeocin resistance cassette were confirmed by PCR across the remaining FRT scar. One clone that yielded the correct PCR signal was also confirmed by sequencing (FIG. 5).

Example 2 HPLC Detection and Quantification of Alanine

The following HPLC method for the alanine detection in the cell culture media was used:

Column: Aminex HPX-87C column (Bio-Rad), 300×7.8 mm, i.d. particle size 9 μm

Mobile phase: Ca(NO3)2 at 0.1 mol/L 90%, Acetonitrile 10%

Flow rate: 0.6 mL/min
Column temperature: 60° C.
Detection: Refractive index detector Under above method, major estimated components in the cell culture sample matrix can be well separated from alanine, without interfering alanine's quantitation.

The amount of the alanine in the sample was determined by external standard calibration method. Standard samples containing alanine from 0.5 to 10.0 g/L were injected and the peak areas were used for calibration. Linear regression coefficient of the calibration curve was 0.9995.

Samples are injected once at 20 µL. Peak areas are used to calculate the amount presenting in the sample by Waters LC Millenium software.

Example 3 HPLC Detection and Quantification of Glucose, Succinate, Lactate, Formate, Acetate and Ethanol HPLC method used
Column: Aminex HPX-87H column (Bio-Rad), 300×7.8 mm, i.d. particle size 9 µm
Mobile phase: H2SO4 4 mM
Flow rate: 0.4 mL/min
Column temperature: 45° C.
Detection: Refractive index detector The amount of the analytes was determined by external standard calibration method. Standard samples containing glucose from 0.1 to 38.0 g/L, succinate, lactate, formate, acetate and ethanol from 0.05 to 10.0 g/L were injected and the peak areas were used for calibration. Linear regression coefficients for all six calibration curves were better than 0.999.

Samples are injected once at 20 µL. Peak areas are used to calculate the amount presenting in the sample by Waters LC Millenium software.

Example 4 Metabolic Evolution of the *E. coli* W Stem Derived from Example 1 for Improved Alanine Yield The *E. coli* stem comprising all mutations as described in Example 1, named *E. coli* Ex1 or QZ16, was used for a metabolic evolution procedure in order to improve the alanine yield of the *E. coli* Ex1 stem.

The metabolic evolution was performed as follows: In a first and second evolution round continuous evolution was performed for 500 hours and 750 hours respectively in NBS medium 5% glucose.

NBS Medium:
3.5 g KH2PO4
5.0 g K2HPO4
3.5 g (NH4)2HPO4
0.25 g MgSO4-7H2O
15 mg CaCL2-2H2O
0.5 mg Thiamine
1 ml trace metal stock The trace metal stock was prepared in 0.1 M HCL, 1.6 g FeCL$_3$-6H$_2$O; 0.2 g CoCl$_2$-6H$_2$O; 0.1 g CuCl$_2$-2H$_2$O; 0.2 g ZnCl$_2$; 0.2 g NaMoO4-2H$_2$O; 0.05 g H$_3$BO$_3$.

Cells were streaked on LB plates and tested for alanine yield. The best *E. coli* stem (*E. coli* Ev1 or QZ17) resulted in fermentation with NBS medium comprising 5% glucose for 24 and 48 h at 37° C. in alanine yield between 84%-86% compared to the alanine yield of the starting stem *E. coli* Ex1 resulting in 80%-83%.

*E. coli* Ev1 was used for further evolution steps which were performed as batch evolution for 20 days. 5% of the cells were reinoculated in fresh medium every 24 h, 48 h, 72 h and so forth in AM1 medium comprising 14% glucose at 37° C.

AM1 Medium:
19.92 mm (NH4)2HPO4=2.6 g/L MW: 132.07
7.56 mm NH4H2PO4=0.87 g/L MW: 115
2.0 mm KCl=0.15 g/L MW: 74.55
1.5 mm MgSO4-7H2O=0.37 g/L MW: 246.5
15 g/L Ammonium sulfate was added in the last step
1 mm betain
1 ml Trace metal stock"

To make 1 L trace metal stock:
The trace metal stock was prepared in 0.12 M HCL, 2.4 g FeCL$_3$-6H$_2$O; 0.3 g CoCl$_2$-6H$_2$O; 0.21 g CuCl$_2$-2H$_2$O; 0.3 g ZnCl$_2$; 0.27 g NaMoO4-2H$_2$O; 0.068 g H$_3$BO$_3$; 0.5 g MnCl2-4H2O From this evolution the stem *E. coli* Ev2, also named QZ18 was isolated. This stem was tested in fermentation which was performed in a fermenter with AM1 medium 14% glucose. The stem *E. coli* Ev2 had an alanine yield between 92%-94% compared to an alanine yield of *E. coli* Ev1 of 91%-92% under same conditions.

After further batch evolution steps for 300 h in AM1 medium comprising 12% glucose and subsequent 10 batch evolution steps in the AM1 comprising 12% glucose, the stem *E. coli* Ev3, also named QZ20 was isolated.

Testing for alanine yield revealed that the stem *E. coli* Ev3 had an alanine yield between 94%-96% in AM1 medium comprising 12% glucose compared to an alanine yield of *E. coli* Ev2 of 92%-93% under same conditions.

Example 5 Determination of Mutations in the Stem *E. coli* Ev3 Compared to *E. coli* Ex1

The genomes of the *E. coli* stems *E. coli* Ex1 and *E. coli* Ev3 were sequenced and the results compared in order to determine the mutations that lead to the increased alanine yield of stem *E. coli* Ev3.

A mutation in the lpd gene was identified, which changed the sequence of the lpd gene from SEQ ID NO 49, encoding the protein having SEQ ID NO 50 in stem *E. coli* Ex1 to SEQ ID NO 51, encoding the protein having SEQ ID NO 52 in stem *E. coli* Ev3.

Further a mutation in the zipA gene was identified which changed the sequence of the zipA gene from SEQ ID NO 45, encoding the protein having SEQ ID NO 46 in stem *E. coli* Ex1 to SEQ ID NO 47, encoding the protein having SEQ ID NO 48 in stem *E. coli* Ev3.

Also a mutation in the ygaW gene was identified which changed the sequence of the ygaW gene from SEQ ID NO 1, encoding the protein having SEQ ID NO 2 in stem *E. coli* Ex1 to SEQ ID NO 3, encoding the protein having SEQ ID NO 4 in stem *E. coli* Ev3.

Moreover a partial deletion of the ydbH coding region and deletion of the ldhA promoter driving expression of the alaD gene and a partial deletion of the 5' coding region of the ydbH gene in front of the alaD gene was identified which brought the alaD gene under control of a promoter having SEQ ID NO: 55. For details of the genomic organization of the new locus see FIG. 7.

Example 6 Confirming the Effect of the Mutated Promoter of the alaD Gene on Alanine Yield In order to confirm the effect of the deletion upstream of the alaD gene that had been detected in *E. coli* Ev3/QZ20 on alanine yield and productivity, the deletion was introduced into the genome of the *E. coli* Ex1 (QZ16) to generate *E. coli* QZ32.

Strain Construction of *E. coli* QZ32

The ydbH-ldhA-cat-sacB cassette (3091 bp) with selectable chloramphenicol resistance marker and counter-selectable sacB marker (confers sucrose sensitivity) was amplified from template vector pQZ11 (Genescript) with primers Rec1_1_F and Rec 1_1_R with Phusion Hot Start High-Fidelity DNA Polymerase (Thermo). The PCR product was Dpnl (NEB) digested at 37 C for 1 h to reduce plasmid template background and gel extracted from a 1% agarose gel with the QIAquick Gel Extraction Kit (Qiagen). The ydbH-ldhA deletion cassette (116 bp) was amplified from a set of self-annealing primers Rec1_2_F and Rec 1_2_R with Phusion Hot Start High-Fidelity DNA Polymerase (Thermo) and purified with the QIAquick PCR Purification Kit (Qiagen).

For Red/ET recombination the Genebridges Red/ET Recombination Kit was used according to manufacturer's protocol. Approximately 200 ng of the ydbH-ldhA-cat-sacB PCR product were electroporated into Red/ET-proficient *E. coli* Ex1 cells. Cultures were plated on LB agar plates with 10 ug/mL chloramphenicol for selection of positive transformants after electroporation. Several colonies were screened for integration of the marker cassette by PCR with the genome-specific primers Rec1_seq_F and Rec1_seq_R. A PCR confirmed clone was used for a second Red/ET recombination with the ydbH-ldhA deletion cassette to replace the cat-sacB marker cassette. Cultures were plated on LB agar plates with 6% sucrose without NaCl for selection of positive transformants after electroporation. Several clones were tested with the genome-specific primers Rec1_seq_F and Rec1_seq_R for loss of the cat-sacB marker cassette. At least one clone that yielded a PCR product of the correct size was also confirmed by sequencing (Genewiz) The heat-sensitive recombineering plasmid pRedET (amp) was cured from strains at 42 C overnight on LB plates before strains were tested in the bioreactor. The ydbH-ldhA deletion was introduced into strain *E coli* Ex1 (QZ16). The resulting strain QZ16 with the ydbH-ldhA promoter deletion was designated as QZ32.

Determination of the Roles of the ydbH Deletion and the New alaD Promoter

In order to further characterize the mechanism by which overexpression of alaD is achieved due to the 529 bp ydbH-ldhA promoter deletion and to determine if the deletion of the partial ydbH gene has a roll in it, two strains based on *E. coli* QZ16 were constructed. In *E. coli* QZ63 only the 50 bp ldhA promoter sequence was deleted and the additional base pairs TATTG that were predicted to complement the new alaD promoter sequence were added instead to form the new promoter (SEQ ID NO: 55). In *E. coli* QZ64 the whole ydbH gene was deleted, while the original ldhA promoter remains undisturbed.

Strain Construction of *E. coli* QZ63 and *E. coli* QZ64

Strain construction for *E. coli* QZ63 and *E. coli* QZ64 was conducted as described previously. The ΔlPdhA-cat-sacB cassette (3091 bp) was amplified with primers Rec1B_1_F and Rec1B_1_R and the ΔydbH-cat-sacB cassette (3091 bp) with primers Rec1C_1_F and Rec1C_1_R. The generated PCR amplicons were used as substrates for Red/ET recombination in *E. coli* QZ16. The PldhA-deletion cassette (125 bp) and the ydbH-deletion cassette (108 bp) were amplified with the self-annealing primers Rec1B_2_F and Rec1B_2_R and Rec1C_2_F and Rec1C_2_R, respectively. The PCR amplicons were used to replace the cat-sacB marker cassettes and to generate the desired genotypes of *E. coli* QZ63 and *E. coli* QZ64. Colonies of *E. coli* QZ63 were tested via PCR with the genome-specific primers Rec1B_seq_F and Rec1B_seq_R and at least one positive clone confirmed by sequencing. Colonies of *E. coli* QZ64 were tested via PCR with the genome-specific primers Rec1C_seq_F and Rec1C_seq_R and at least one positive clone confirmed by sequencing.

SDS-PAGE Analysis

To test the effect of the ydbH-ldhA promoter deletion on the expression level of alaD, SDS-PAGE analysis of the generated *E. coli* QZ32 was performed in comparison to *E. coli* W, *E. coli* QZ16 and *E. coli* QZ20. Cells from an overnight culture in LB medium at 37 C, 200 rpm, were normalized to OD600, harvested and lysed. Soluble protein fractions were loaded onto an SDS-PAGE for comparison.

Figure 8:
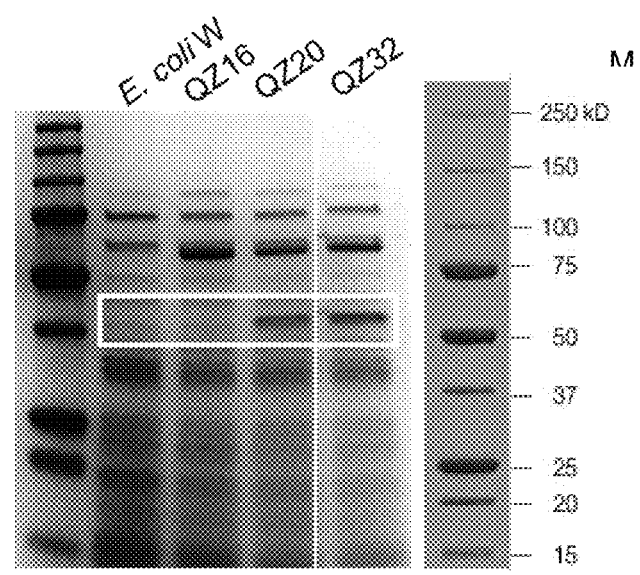

The amount of expressed alaD (39.37 kDa) in the strain with the 529 bp ydbH-ldhA promoter deletion (QZ32) as found in *E. coli* QZ20 was significantly higher than in QZ16 and comparable to AlaD expression levels in QZ20 (FIG. 8). This result shows that the 529 bp deletion found in *E. coli* QZ20 upstream of alaD causes a significant overexpression of the alaD gene.

AlaD Enzymatic In Vitro Assay

*E. coli* QZ32 was tested for AlaD activity in crude cell lysates in vitro in comparison to *E. coli* W, *E. coli* QZ16 and *E. coli* QZ20 cell lysates.

Crude lysates were prepared from overnight cultures grown at 37 C in LB medium. Cells were pelleted by centrifugation and lysed using BugBuster (Novagen) detergent according to the manufacturer's recommended protocol. Total protein concentrations of the crude lysates were determined using a Bradfrod Assay (Amresco) and a bovine serum albumin (BSA) standard curve. The reaction catalyzed by alaD (L-alanine+$H_2O$+$NAD^+$⇌pyruvate+$NH_3$+NADH+$H^+$) is reversible and the reverse conversion of L-alanine to pyruvate was monitored indirectly via the formation of NADH with a spectrophotometer at $\lambda$=340 nm.

The in vitro assay reaction contained 125 mM glycine/KOH (pH 10.2), 100 mM L-alanine in 125 mM glycine/KOH (pH 10.2), 1.25 mM $NAD^+$ in 10 mM Tris-HCl (pH 7.0) and 10 μL crude cell lysate normalized to OD600 in glycine/KOH (total assay volume 300 μL). Assay components were assembled on ice and the reaction started by adding NAD. The kinetic read ($\lambda$=340 nm) was carried out at 37° C.×15 min (every 30 sec).

Figure 9:
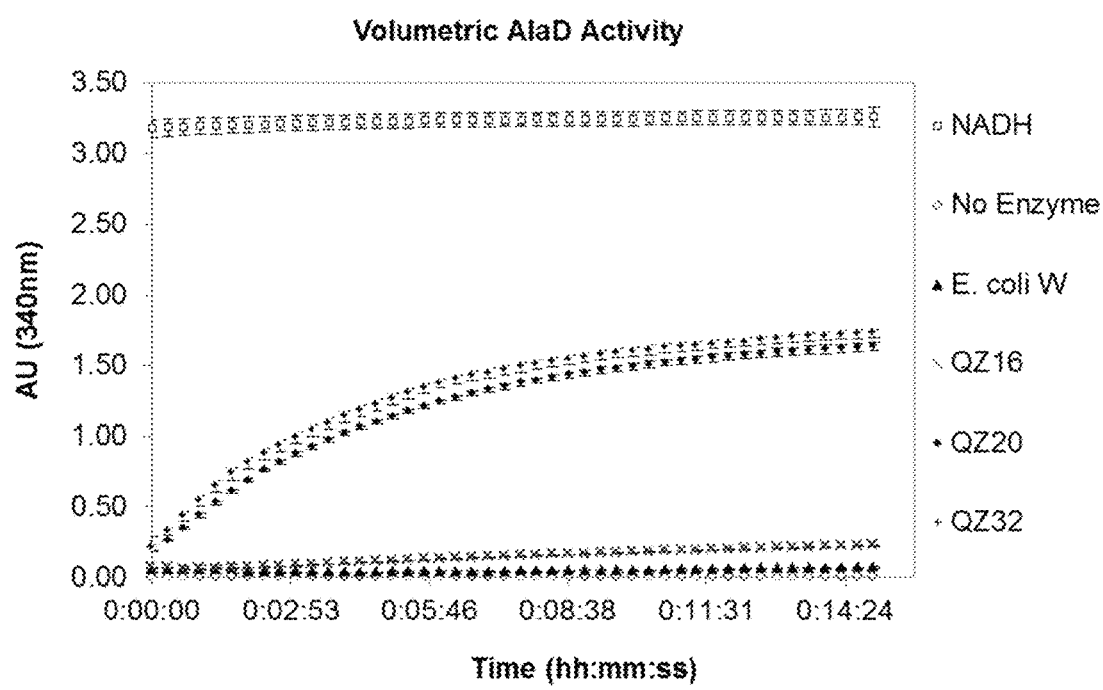

Crude lysate of *E. coli* W, which does not contain an alaD gene, produced results similar to the negative control without crude cell lysate (FIG. 9). As expected from SDS-PAGE analysis (FIG. 8) *E. coli* QZ16, in which the ldhA gene was replaced with the alaD gene, showed only little alaD enzyme activity compared to *E. coli* W. QZ20 with the ydbH-alaD promoter deletion showed a significantly higher volumetric alaD enzyme activity compared to *E. coli* QZ16 as expected from the observed increase in AlaD expression. The volumetric alaD enzyme activity of *E. coli* QZ32 was close to the *E. coli* QZ20 enzyme activity.

RT-qPCR Analysis of alaD Gene Transcription Levels

Beside SDS-PAGE analysis to monitor alaD protein expression alaD transcription levels were determined via quantitative reverse transcription PCR (RT-qPCR). The iTaq Universal One-Step Kit from Biorad was used for SYBR Green-based one-step reverse transcription (RT)-qPCR reactions. From a parallel batch-fermentation of *E. coli* QZ16 and *E. coli* QZ20 that was conducted as described previously, culture samples were taken at 8, 11, 22, 28 and 48 h. Samples were immediately treated with RNAprotect Bacteria Reagent (Qiagen) to stabilize the RNA. RNA was extracted from the samples with the AurumTotal RNA Mini Kit (Biorad) according to the manufacturer's manual. The isolated RNA was further treated with the DNA-free DNA Removal Kit (lifetechnologies) to remove contaminating genomic DNA and reduce background during qPCR. The RNA was quantified spectrophotometrically at $\lambda=260$ nm.

Figure 10:
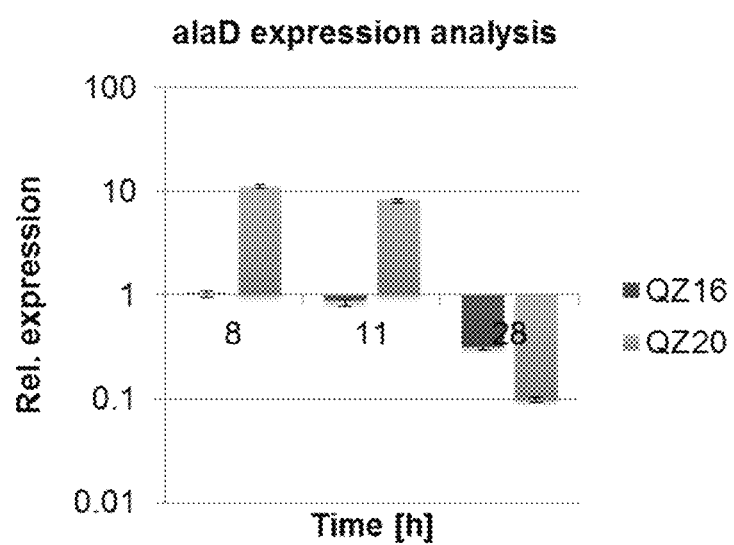

A 7-step 10-fold dilution series of 100 ng *E. coli* QZ16 RNA was tested with the RT-qPCR primers (Table 1)) alaD_RT_F and alaD_RT_R, specific for the alaD gene, and rrsA_RT_F and rrsA_RT_R, specific for the ribosomal 16 S RNA coding rrsA gene, which served as a reference gene during qPCR trials. The suitable linear dynamic range of RNA dilutions that led to signal amplification efficiencies 90%<E<110% and a linear regression factor $R^2$>0.985 were determined for each RT-qPCR primer set. rrsA was tested for its suitability as an internal reference gene for normalization and found to be expressed stable among all the tested samples (data not shown). RT-qPCR reactions were carried out with the CFX96 Touch Real-Time PCR Detection System (Biorad) according to the manufacturer's protocol. Relative quantification of gene expression was calculated with *E. coli* QZ16 8 h RNA as the internal calibrator according to the $\Delta\Delta$Ct method.

alaD shows an 11-fold higher expression in *E. coli* QZ20 compared to *E. coli* QZ16 (FIG. 10) at 8 h. This is another confirmation of the impact of the ydbH-ldhA promoter deletion on alaD gene expression.

Fermentation Trial of *E. coli* QZ32 in Comparison to *E. coli* QZ16

*E. coli* strain QZ32 was tested for its performance during fermentation in a lab-scale bioreactor. Alanine formation was monitored in comparison to *E. coli* strains QZ16 and QZ20. Precultures were grown in shake flasks with LB medium, 20% filling volume at 37 C and 200 rpm overnight. The fermentation was performed in the DASGIP 1.5 L parallel bioreactor system (Eppendorf) in 500 mL NBS medium (3.50 g/L $KH_2PO_4$, 5.00 g/L $K_2HPO_4$, 0.25 g/L $MgSO_4.7 H_2O$, 3.50 g/L $(NH_4)2HPO_4$, 0.5 mg/L Thiamine, 15.00 mg/L $CaCl_2.2 H_2O$, 15.00 g/L $(NH_4)_2SO_4$, 153.61 mg/L Betaine, 1 ml/L trace metal stock solution). The trace metal stock comprised 1.6 g/L $FeCL_3.6 H_2O$; 0.2 g/L $CoCl_2.6 H_2O$; 0.1 g/L $CuCl_2.2 H_2O$; 0.2 g/L $ZnCl_2$; 0.2 g/L $NaMoO_4.2 H_2O$; 0.05 g/L $H_3BO_3$, 0.1 M HCL. 80 g/L Glucose were used as the carbon source in the fermentation medium.

*E. coli* cells equivalent to an OD600•mL of 7 were harvested via centrifugation and resuspended in 5 mL NBS medium. # OD600•mL=(OD600 of undiluted culture)×(culture volume in mL). The 5 mL resuspended cells were used to inoculate the 500 mL fermentation medium in the 1.5 L DASGIP bioreactor. Each strain was run in duplicates at 37 C and 400 rpm stirrer speed. 5N NH4OH was used to control the pH to 6.8 and provide the culture with ammonium as an alanine precursor throughout the fermentation. No air was sparged during the fermentation and the vessel was not pressurized so that after the initial consumption of dissolved oxygen in the medium by the cells the fermentation was run under microaerobic conditions. Samples were taken throughout the fermentation and analyzed by HPLC for alanine and glucose concentrations.

Figure 11:
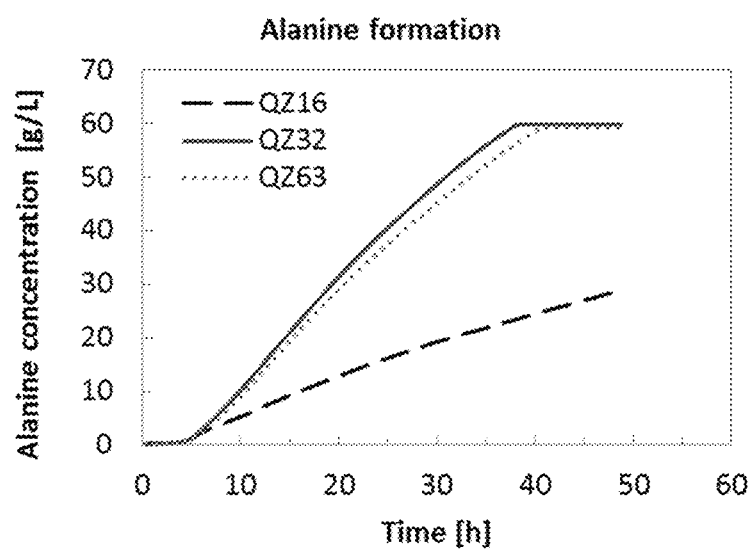
Figure 12:
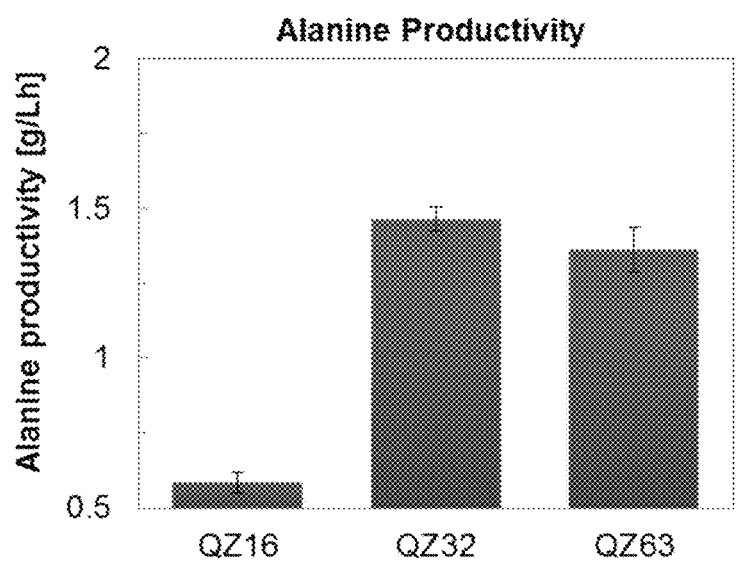

It was obvious that the ydbH-ldhA promoter deletion and the resulting higher expression level of the key enzyme alaD in QZ32 had a strong influence on alanine formation (FIG. 11). A significantly higher maximal volumetric alanine formation rate of 2.00±0.07 g/(Lh) was reached with *E. coli* QZ32 compared to *E. coli* QZ16, which exhibited a maximum volumetric alanine formation rate of about 0.74±0.02 g/(Lh). *E. coli* QZ16 was not able to fully consume the 80 g/L glucose in the fermentation medium, even after an elongated fermentation time of >50 h. The volumetric alanine productivity (space-time-yield), defined as the amount of product generated divided by reactor volume and by time, of QZ16 after 50 h was 0.58±0.04 g/(Lh). *E. coli* QZ32 showed an overall volumetric alanine productivity of 1.47±0.04 g/(Lh) at glucose depletion (FIG. 12).

Fermentation Trial of *E. coli* QZ63 and *E. coli* QZ64

The fermentation was conducted as previously. *E. coli* QZ63, *E. coli* QZ64, *E. coli* QZ16 and *E. coli* QZ32 were run in parallel in duplicates.

The ydbH gene deletion in QZ64 did not lead to an increase in alanine productivity compared to QZ16 (data not shown). However, the replacement of the 50 bp in the wt ldhA promoter with the TATTG nts that are predicted to complement the new alaD promoter, led to a significant increase in alanine formation of QZ63 compared to QZ16 (FIG. 11). Alanine formation of QZ63 was comparable to QZ32, which carries the extended 529 bp ydbH-ldhA promoter deletion. QZ63 also showed a similar volumetric alanine productivity of 1.36±0.08 g/(Lh) to QZ32 with 1.47±0.05 g/(Lh) (FIG. 12).

This shows that only the new promoter upstream of alaD is responsible for increased alaD expression and thus better alanine productivity.

Example 7 Confirming the Effect of the SNP in the ygaW Gene on Alanine Yield

In the *E. coli* QZ20 genome sequence a GIST in the ygaW gene was identified that leads to a Q5H amino acid exchange. YgaW, also termed alaE was previously determined to be an alanine exporter. It was shown that overexpression of ygaW from a plasmid led to alanine excretion (WO2012/172822). To test the influence of the SNP in the ygaW gene on alanine yield the respective mutation was introduced into the *E. coli* QZ32 genetic background with enhanced alaD expression compared to QZ16. Further mutations were introduced into the same codon in order to test whether other amino acid exchanges have a beneficial effect on alanine yield.

Strain Construction of *E. coli* QZ33, QZ60, QZ61, QZ62

The strain construction was performed as described previously. The ygaW-cat-sacB cassette (3091 bp) was amplified with primers Rec2_1_F and Rec2_1_R. The ygaW-SNP-cassette (130 bp) was amplified with the self-annealing primers Rec2_2_F and Rec2_2_R. Control PCRs were performed with the genome-specific primers Rec2_seq_F and Rec2_seq_R. The generated strain with ydbH-ldhA promoter deletion and YgaW Q5H SNP was termed QZ33.

Like-wise alternative amino acid substitutions were introduced into *E. coli* QZ32. Double-stranded DNA (gBlocks) containing the mutation of interest were ordered from IDT Technologies and used to replace the cat-sacB marker cassette during Red/ET recombination. *E. coli* QZ60 harbors an YgaW Q5N mutation, *E. coli* QZ61 an YgaW Q5R mutation and *E. coli* QZ62 an YgaW Q5Y mutation.

Fermentation Trial of *E. coli* QZ32, QZ60, QZ61 and QZ62, QZ33

Strain QZ33 (ygaW Q5H, ydhB-ldha deletion mutant) was tested for its performance during fermentation in comparison to *E. coli* QZ32. The batch fermentation was conducted as described previously.

The ygaW Q5H mutation led to a further increase of the alanine formation of *E. coli* QZ33 compared to *E. coli* QZ32

Figure 13:
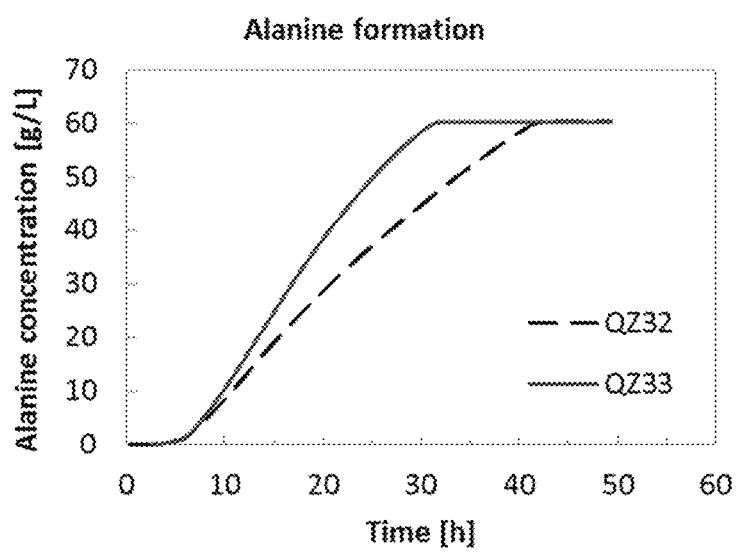
Figure 14:
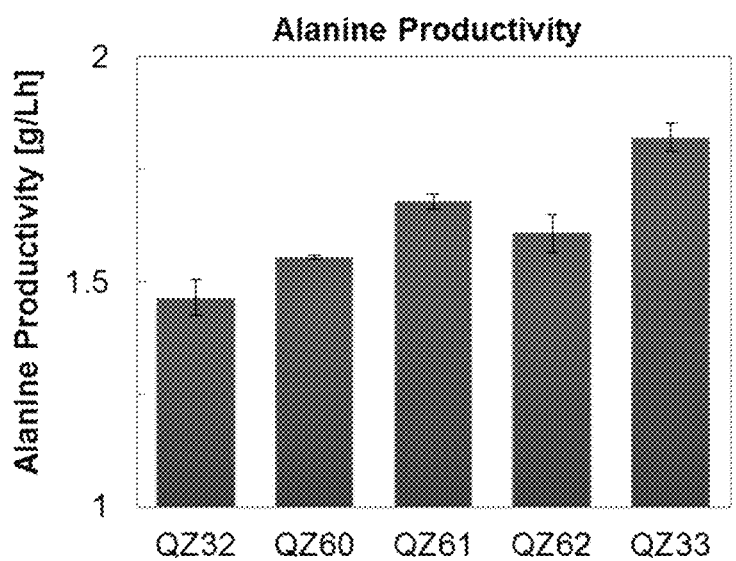

(FIG. 13). A further enhanced volumetric alanine productivity of 1.82±0.03 g/(Lh) was reached with *E. coli* QZ33 compared 1.47±0.05 g/(Lh) of *E. coli* QZ32 (FIG. 14).

Figure 15:
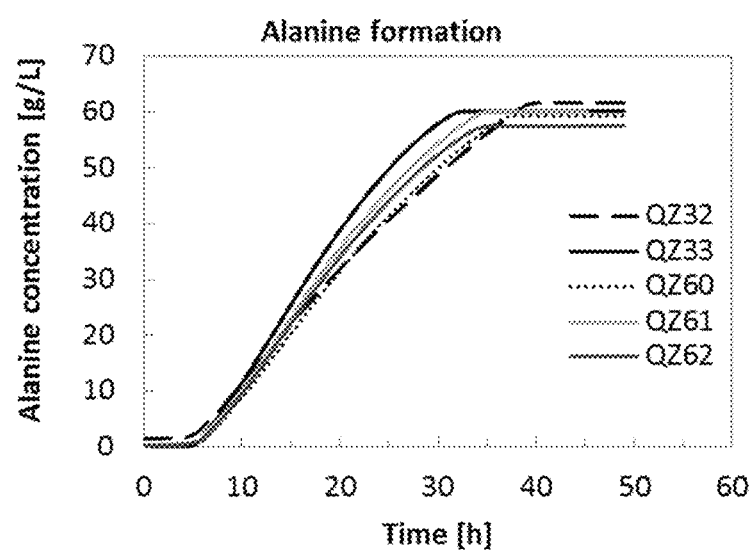

The strains with the alternative Q5 mutations were tested under identical conditions during batch fermentation. All three alternative mutations showed a higher max alanine formation rate compared to *E. coli* QZ32 with the wild-type YgaW (FIG. 15). *E. coli* QZ60 (YgaW Q5N) showed a volumetric alanine productivity of 1.56±0.004 g/(Lh), *E. coli* QZ61 (YgaW Q5R) 1.68±0.02 g/(Lh) and QZ62 (YgaW Q5Y) 1.61±0.04 g/(Lh) compared to 1.47±0.04 g/(Lh) of QZ32 (FIG. 14). Accordingly, the arginine substitution had the strongest beneficial effect, followed by the tyrosine substitution and the asparagine substitution. However, *E. coli* QZ33 with the YgaW Q5H mutation found during the adaptive evolution outperformed each of the rationally designed mutants with an volumetric alanine productivity of 1.82±0.03 g/(Lh).

RT-qPCR Analysis of ygaW Gene Transcription Levels

The exact mechanism by which the single SNP in the N-terminal region of the YgaW confers enhanced alanine exporter activity is not known. We have tested the gene expression levels of ygaW in RNA samples of QZ16 and QZ20 via RT-qPCR as described previously with the gene-specific primers ygaW_RT_F and ygaW_RT_R (Table 1). Gene expression data was normalized with the rrsA as reference gene and calculated in relation ti gene expression levels in *E. coli* QZ16 8 h as calibrator.

Figure 16:
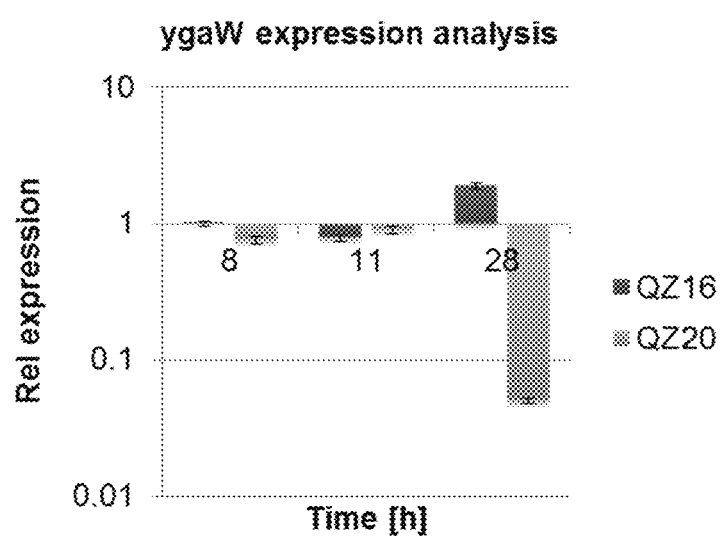

No significant up- or downregulation of ygaW gene expression was observed for the strain samples from 8 h and 11 h fermentation (FIG. 16). These results confirm that the effect of the YgaW Q5H mutation is not related to higher ygaW expression levels, but must directly influence YgaW activity or stability.

Example 8 Confirming the Effect of the SNP in the zipA Gene on Alanine Yield

To determine the role the zipA SNP plays for alanine productivity, the zipA SNP was introduced into *E. coli* Strain QZ33 (ydbH-ldhA promoter deletion, YgaW Q5H).

Strain Construction

Since zipA is an essential gene, the zipA cat-sacB integration cassette was designed to not interrupt zipA but integrate downstream of it. The cassette was amplified from vector pQZ11 (Genescript) with primers Rec4B_1_F/R (Table 1). The zipA SNP cassette (197 bp) was amplified from the genomic DNA of strain QZ20 with primers Rec4B_2_F/R. Red/ET was conducted as described previously. Clones were tested by colony PCR with Rec4_seq_F/R sequencing primers. The zipA SNP was introduced into *E. coli* QZ33 with the ldhA promoter deletion and the ygaW SNP. The generated strain was designated as QZ41.

Fermentation Trial of QZ33 and QZ41

Strain QZ41 (zipA SNP, ygaW Q5H, ΔIdha mutant) was tested for its performance during fermentation as described before. Alanine formation was monitored in comparison to strain QZ33.

Figure 17:
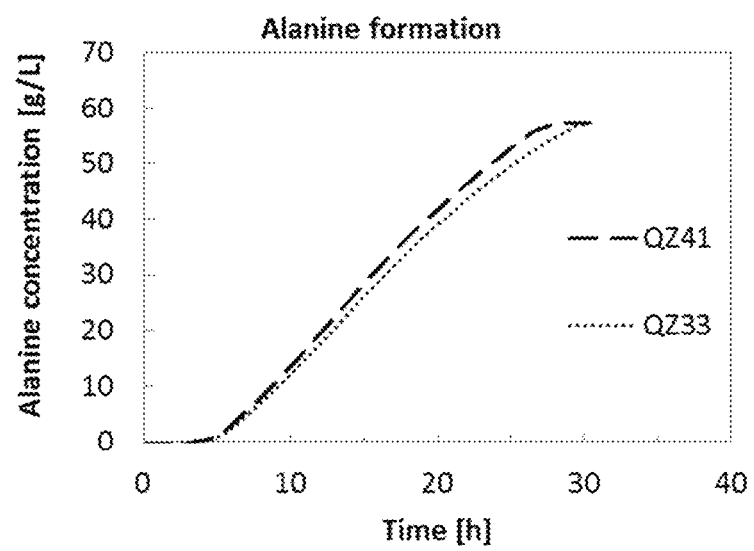
Figure 18:
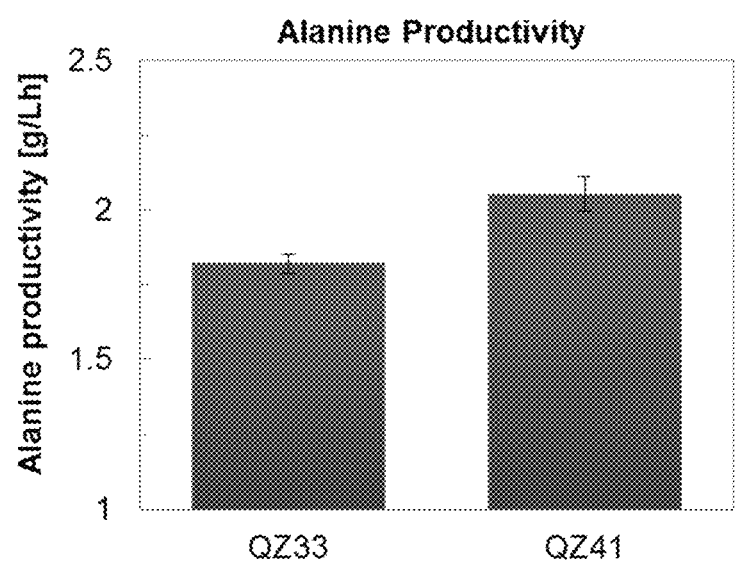

The zipA SNP led to a further increase in alanine formation compared to the progenitor strain QZ33 (FIG. 17). The volumetric alanine productivity of QZ41 was 2.06±0.06 g/(Lh) compared to 1.82±0.03 g/(Lh) (FIG. 18).

Example 9 Confirming the Effect of the SNP in the lpd Gene on Alanine Yield

In order to test the influence of the lpd SNP on alanine productivity, it was introduced into *E. coli* WZ33 ((ydbH-ldhA del, ygaW Q5H) to generate *E. coli* QZ52 and into *E. coli* QZ41 (ydbH-ldhA del, ygaW Q5H, zipA SNP) to generate *E. coli* strain QZ53.

Strain Construction

The lpd cat-sacB integration cassette (3087 bp) was designed to not interrupt lpd but integrate upstream of it. The cassette was amplified from vector pQZ11 (Genescript) with primers Rec3B_1_F/R (Table 1) and used to be integrated into strain QZ20, which carries the lpd SNP. The lpd_SNP-cat-sacB cassette (3527 bp) was amplified from the genomic DNA of strain QZ20 with the integrated cat-sacB cassette with primers Rec3B_2_F/R and used to integrate into *E. coli* QZ33 and *E. coli* QZ41, respectively. The cat-sacB replacement cassette was amplified with primers Rec3B_F/R primers from the genome of QZ20 and used to remove the cat-sacB marker cassette in QZ33 and QZ41. Red/ET was conducted as described previously. Clones were tested by colony PCR with Rec3_seq_F and Rec_3B_FR sequencing primers.

Fermentation Trial QZ33 Vs QZ52

Strain QZ52 (ΔydbH-ldha promoter, ygaW Q5H, lpd SNP) was tested for its performance during fermentation as described before with 10 g/L glucose as carbon source. Alanine formation was monitored in comparison to strain QZ33.

Figure 19:
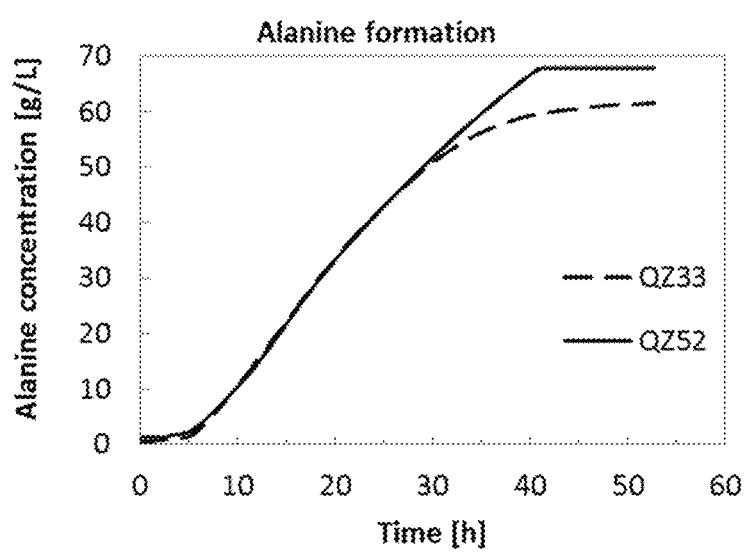
Figure 20:
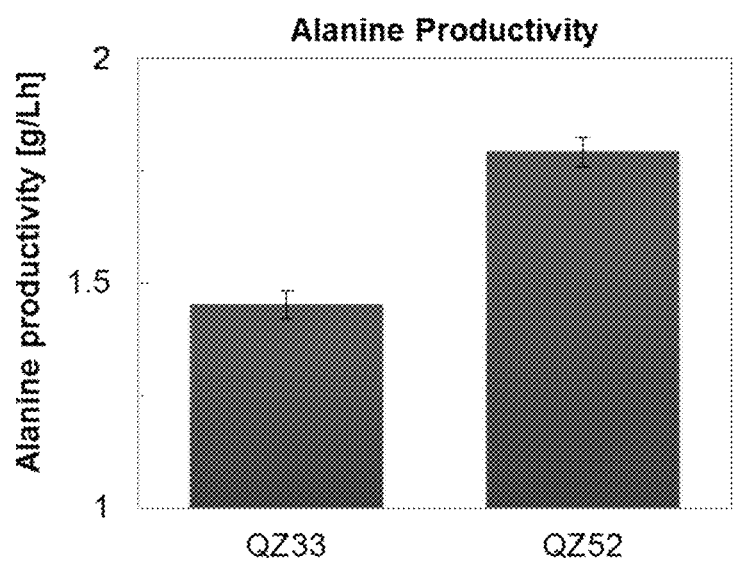

The lpd SNP had a significant positive effect on alanine formation compared to QZ33 (FIG. 19). QZ33 was not able to fully consume the 100 g/L glucose in the fermentation medium within the monitored time of 52 h. QZ52 fully consumed the available glucose within 41 h and reached a volumetric alanine productivity of 1.79±0.160 g/(Lh) compared to QZ33 with 1.45±0.007 g/(Lh) in the same amount of time (FIG. 20).

Fermentation Trial QZ41 Vs QZ53

Strain QZ53 (ΔydbH-ldha promoter, ygaW Q5H, zipA SNP, lpd SNP), in which the lpd SNP was introduced into *E. coli* QZ41 was tested for its performance during fermentation as described before. Alanine formation was monitored in comparison to strain QZ41.

Figure 22:
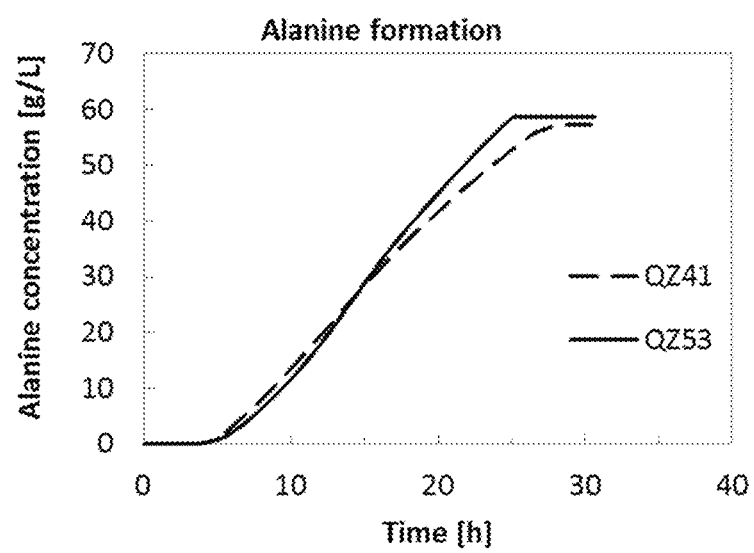
Figure 23:
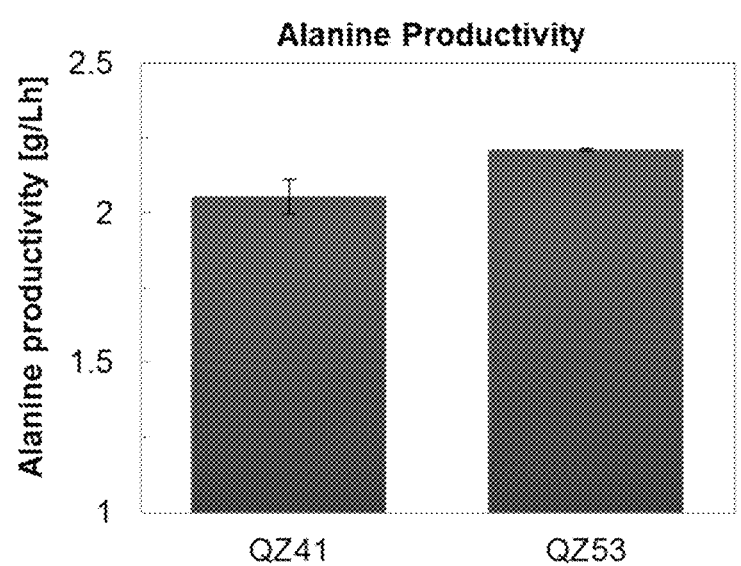

The lpd SNP in QZ53 also showed its positive effect on alanine formation compared to QZ41 (FIG. 22). The volumetric alanine productivity of QZ53 was 2.21±0.004 g/(Lh) compared to QZ41 with 2.06±0.06 g/(Lh) (FIG. 23).

Figure 21:
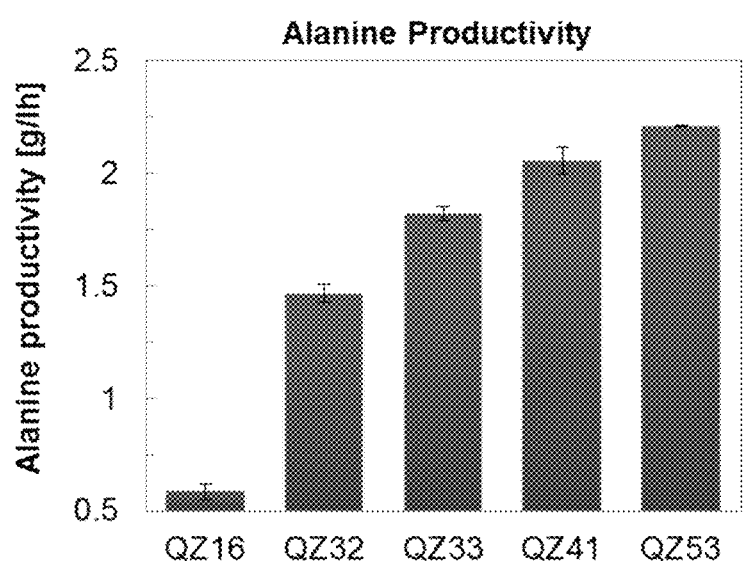

The overall improvement of volumetric alanine productivities as a result of the ydbH-ldhA promoter deletion, ygaW Q5H SNP, zipA SNP and lpd SNP are represented in FIG. 21.

Overexpression of the lpd Gene

An additional copy of lpd under the control of its native promoter was introduced into the pACYC184 plasmid. pACYC184-Lpd (p15 ori, Chl$^R$, ~15 copies per cell) was constructed via commercial InFusion cloning technology (Clontech, Mountain View, Calif., USA). First the vector pACYC184 (p15 ori, chl$^R$, tet$^R$) was obtained via NEB (Ipswich, Mass., USA) and linearized with HindIII and SalI restriction endonucleases, also from NEB. This digest removed most of the tetracycline-resistance gene. Separately, the lpd ORF was PCR amplified from wild-type *E. coli* W DNA with Phusion polymerase (Thermo Scientific, Waltham, Mass.) with the following primers (lpd-pACYC_F SEQ ID NO: 114 and lpd-pACYC_R SEQ ID NO: 115). The primers contained additional 15 bp overhangs homologous to the linearized vector ends to facilitate seamless cloning. The InFusion reaction was then performed as according to the manufacturer's protocol with both purified linearized vector backbone and lpd insert. The resulting InFusion products were then used to transform QZ33 (ydbH-ldhA promoter deletion, YgaW Q5H) via electroporation and selection on LB chloramphenicol plates. Positive clones were PCR identified, confirmed by DNA sequencing, and used in the fermentations for the overexpression studies.
Fermentation Comparison Between QZ33/pACYC184 and QZ33/pACYC184-lpd Alanine productivity of the strain comprising the lpd expression vector (QZ33/pACYC184-lpd) was compared to a strain comprising an empty control vector (QZ33/pACYC184). Precultures were grown in shake flasks with LB medium, 20% filling volume at 37 C and 200 rpm overnight. The fermentation was performed in the DASGIP 1.5 L parallel bioreactor system with 8% glucose of NBS medium. The other conditions were the same as before.

Figure 24:
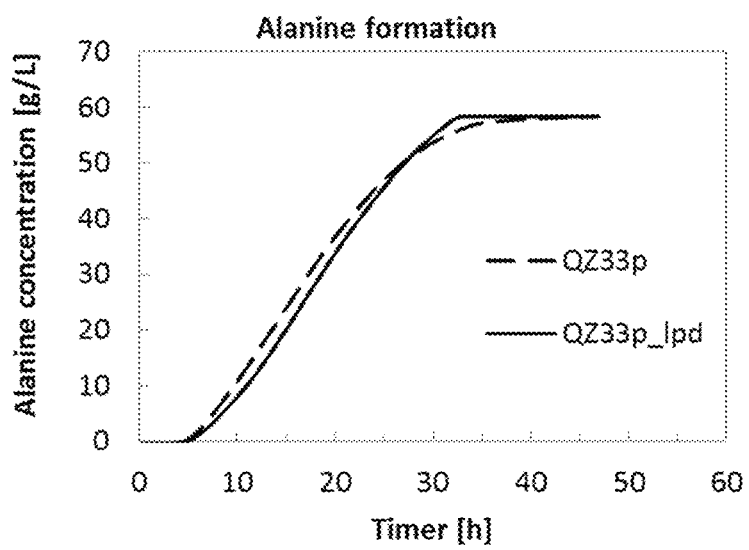

At the time point of 33 h, QZ33/pACYC184-lpd made 58.4 g/L alanine compared with the 57.1 g/L of QZ33/pACYC184 (FIG. 24).

Figure 25:
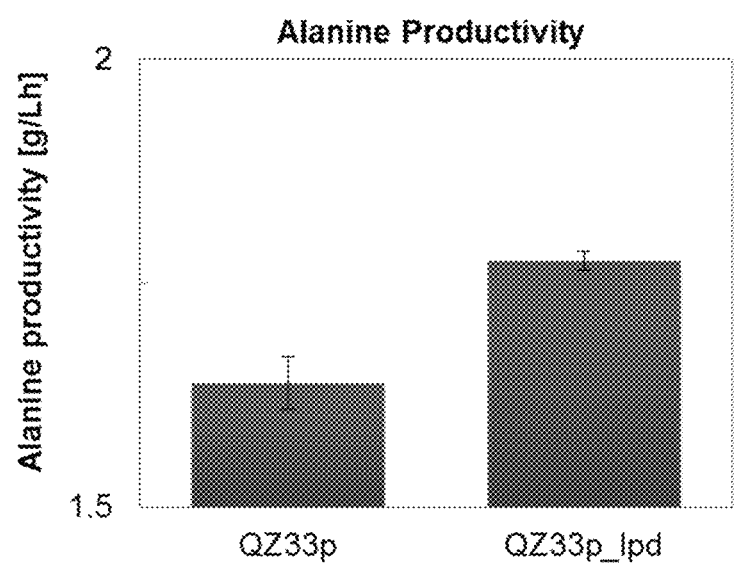

Compared with QZ33/pACYC184, the space time yield (productivity) of QZ33/pACYC184-lpd was also increased from 1.63 to 1.77 g/h/l (FIG. 25).

We claim:

1. A recombinant nucleic acid molecule encoding an alanine transporter and having a sequence selected from the group of
   (I) a nucleic acid molecule comprising the sequence of SEQ ID NO: 1, wherein the codon corresponding to position 13-15 of SEQ ID NO: 1 does not encode amino acid glutamine and is not a stop codon,
   (II) a nucleic acid molecule encoding a polypeptide having the sequence of SEQ ID NO: 2, wherein the amino acid of the polypeptide corresponding to position 5 of SEQ ID NO: 2 is not glutamine, and
   (III) a nucleic acid molecule encoding a polypeptide having at least 95% sequence identity to a polypeptide having the sequence of SEQ ID NO: 2, wherein the amino acid of the polypeptide corresponding to position 5 of SEQ ID NO: 2 is not glutamine.

2. The recombinant nucleic acid molecule of claim 1 having the sequence of SEQ ID NO: 1, wherein the nucleic acid molecule encodes, at a position corresponding to position 5 of SEQ ID NO: 2, the amino acid histidine or another basic amino acid, the amino acid asparagine or another aliphatic amino acid, the amino acid arginine or another aliphatic amino acid, or the amino acid tyrosine or another aromatic amino acid.

3. A recombinant expression construct comprising at least one promoter functional in a microorganism operably linked to the nucleic acid molecule of claim 1.

4. A recombinant vector comprising the nucleic acid molecule of claim 1.

5. A recombinant microorganism comprising the nucleic acid of claim 1.

6. A composition comprising the recombinant microorganism according to claim 5.

7. A method of producing pyruvate, succinate, aspartate, malate, lactate, valine, leucine and/or alanine comprising culturing the recombinant microorganism according to claim 5 under conditions that allow for the production of pyruvate, succinate, aspartate, malate, lactate, valine, leucine, and/or alanine.

8. A process for fermentative production of pyruvate, succinate, aspartate, malate, lactate, valine, leucine and/or alanine comprising the steps of
   I) growing the microorganism according to claim 5 in a fermenter and
   II) recovering pyruvate, succinate, aspartate, malate, lactate, valine, leucine and/or alanine from the fermentation broth obtained in I).

* * * * *

SEQUENCE LISTING

```
<160> NUMBER OF SEQ ID NOS: 126

<210> SEQ ID NO 1
<211> LENGTH: 450
<212> TYPE: DNA
<213> ORGANISM: Escherichia coli
<220> FEATURE:
<221> NAME/KEY: misc_feature
<223> OTHER INFORMATION: ygaW

<400> SEQUENCE: 1
atgttctcac cgcagtcacg cttgcgtcat gcagttgcag atacgttcgc gatggttgtt      60
tactgttctg tcgtgaacat gtgtattgaa gttttcctct ccggaatgag cttcgaacag     120
tctttttatt ccagattggt agcgattccg gtgaacatct taattgcatg gccatacggt     180
atgtaccgtg atctgtttat gcgcgcggca cgcaaagtta gcccgtcggg ctggataaaa     240
aatctggctg atatcctggc ttatgtgacg ttccagtcac cggtgtatgt ggcgatcttg     300
ttagtggtgg gcgcagactg gcatcagatt atggcggcgg tcagttcaaa catcgttgtt     360
tcgatgttga tggggcggt ttatggctac ttcctcgatt attgccgccg actgtttaaa     420
gtcagccgtt accagcaggt aaaagcctga                                      450

<210> SEQ ID NO 2
<211> LENGTH: 149
<212> TYPE: PRT
<213> ORGANISM: Escherichia coli
<220> FEATURE:
<221> NAME/KEY: misc_feature
<223> OTHER INFORMATION: ygaw

<400> SEQUENCE: 2

Met Phe Ser Pro Gln Ser Arg Leu Arg His Ala Val Ala Asp Thr Phe
1               5                   10                  15

Ala Met Val Val Tyr Cys Ser Val Val Asn Met Cys Ile Glu Val Phe
                20                  25                  30

Leu Ser Gly Met Ser Phe Glu Gln Ser Phe Tyr Ser Arg Leu Val Ala
            35                  40                  45

Ile Pro Val Asn Ile Leu Ile Ala Trp Pro Tyr Gly Met Tyr Arg Asp
        50                  55                  60

Leu Phe Met Arg Ala Ala Arg Lys Val Ser Pro Ser Gly Trp Ile Lys
65                  70                  75                  80

Asn Leu Ala Asp Ile Leu Ala Tyr Val Thr Phe Gln Ser Pro Val Tyr
                85                  90                  95

Val Ala Ile Leu Leu Val Val Gly Ala Asp Trp His Gln Ile Met Ala
            100                 105                 110

Ala Val Ser Ser Asn Ile Val Val Ser Met Leu Met Gly Ala Val Tyr
        115                 120                 125

Gly Tyr Phe Leu Asp Tyr Cys Arg Arg Leu Phe Lys Val Ser Arg Tyr
    130                 135                 140
```

Gln Gln Val Lys Ala
145

<210> SEQ ID NO 3
<211> LENGTH: 450
<212> TYPE: DNA
<213> ORGANISM: Escherichia coli
<220> FEATURE:
<221> NAME/KEY: misc_feature
<223> OTHER INFORMATION: ygaW Mut

<400> SEQUENCE: 3

```
atgttctcac cgcattcacg cttgcgtcat gcagttgcag atacgttcgc gatggttgtt      60
tactgttctg tcgtgaacat gtgtattgaa gttttcctct ccggaatgag cttcgaacag     120
tcttttatt ccagattggt agcgattccg gtgaacatct taattgcatg gccatacggt     180
atgtaccgtg atctgtttat gcgcgcggca cgcaaagtta gcccgtcggg ctggataaaa     240
aatctggctg atatcctggc ttatgtgacg ttccagtcac cggtgtatgt ggcgatcttg     300
ttagtggtgg gcgcagactg gcatcagatt atggcggcgg tcagttcaaa catcgttgtt     360
tcgatgttga tggggcggt ttatggctac ttcctcgatt attgccgccg actgtttaaa     420
gtcagccgtt accagcaggt aaaagcctga                                      450
```

<210> SEQ ID NO 4
<211> LENGTH: 149
<212> TYPE: PRT
<213> ORGANISM: Escherichia coli
<220> FEATURE:
<221> NAME/KEY: misc_feature
<223> OTHER INFORMATION: ygaW Mut

<400> SEQUENCE: 4

Met Phe Ser Pro His Ser Arg Leu Arg His Ala Val Ala Asp Thr Phe
1               5                   10                  15

Ala Met Val Val Tyr Cys Ser Val Val Asn Met Cys Ile Glu Val Phe
            20                  25                  30

Leu Ser Gly Met Ser Phe Glu Gln Ser Phe Tyr Ser Arg Leu Val Ala
        35                  40                  45

Ile Pro Val Asn Ile Leu Ile Ala Trp Pro Tyr Gly Met Tyr Arg Asp
    50                  55                  60

Leu Phe Met Arg Ala Ala Arg Lys Val Ser Pro Ser Gly Trp Ile Lys
65                  70                  75                  80

Asn Leu Ala Asp Ile Leu Ala Tyr Val Thr Phe Gln Ser Pro Val Tyr
                85                  90                  95

Val Ala Ile Leu Leu Val Val Gly Ala Asp Trp His Gln Ile Met Ala
            100                 105                 110

Ala Val Ser Ser Asn Ile Val Val Ser Met Leu Met Gly Ala Val Tyr
        115                 120                 125

Gly Tyr Phe Leu Asp Tyr Cys Arg Arg Leu Phe Lys Val Ser Arg Tyr
    130                 135                 140

Gln Gln Val Lys Ala
145

<210> SEQ ID NO 5
<211> LENGTH: 2283
<212> TYPE: DNA
<213> ORGANISM: Escherichia coli
<220> FEATURE:
<221> NAME/KEY: misc_feature
<223> OTHER INFORMATION: pflB

<400> SEQUENCE: 5

```
atgtccgagc ttaatgaaaa gttagccaca gcctgggaag gttttaccaa aggtgactgg      60
cagaatgaag taaacgtccg tgacttcatt cagaaaaact acactccgta cgagggtgac     120
gagtccttcc tggctggcgc tactgaagcg accaccaccc tgtgggacaa agtaatggaa     180
ggcgttaaac tggaaaaccg cactcacgcg ccagttgact ttgacaccgc tgttgcttcc     240
accatcacct ctcacgacgc tggctacatc aacaaagcgt tggaaaaagt tgttggtcta     300
cagactgaag ctccgctgaa acgtgctctt atcccgttcg gtggtatcaa atgatcgag      360
ggttcctgca aagcgtacaa ccgcgaactg gacccgatga tcaaaaaaat cttcactgaa     420
taccgtaaaa ctcacaacca gggcgtgttc gacgtttaca ctccggacat cctgcgttgc     480
cgtaaatccg gtgttctgac cggtctgcca gatgcttatg gccgtggccg tatcatcggt     540
gactaccgtc gcgttgcgct gtacggtatc gactacctga tgaaagacaa atacgctcag     600
ttcacctctc tgcaggctga tctggaaaac ggcgtaaacc tggaacagac tatccgtctg     660
cgcgaagaaa tcgctgaaca gcaccgcgct ctgggtcaga tgaaagaaat ggctgcgaaa     720
tacggctacg acatctctgg tccggctacc aacgctcagg aagctatcca gtggacttac     780
ttcggctacc tggctgctgt taagtctcag aacggtgctg caatgtcctt cggtcgtacc     840
tccaccttcc tggatgtgta catcgaacgt gacctgaaag ctggcaagat caccgaacaa     900
gaagcgcagg aaatggttga ccacctggtc atgaaactgc gtatggttcg cttcctgcgt     960
actccggaat acgatgaact gttctctggc gacccgatct gggcaaccga atctatcggt    1020
ggtatgggcc tcgacggtcg taccctggtt accaaaaaca gcttccgttt cctgaacacc    1080
ctgtacacca tgggtccgtc tccggaaccg aacatgacca ttctgtggtc tgaaaaactg    1140
ccgctgaact tcaagaaatt cgccgctaaa gtgtccatcg acacctcttc tctgcaatat    1200
gagaacgatg acctgatgcg tccggacttc aacaacgatg actacgctat tgcttgctgc    1260
gtaagcccga tgatcgttgg taaacaaatg cagttcttcg gtgcgcgtgc aaacctggcg    1320
aaaaccatgc tgtacgcaat caacggcggc gttgacgaaa aactgaaaat gcaggttggt    1380
ccgaagtctg aaccgatcaa aggcgatgtc ctgaactatg atgaagtgat ggagcgcatg    1440
gatcacttca tggactggct ggctaaacag tacatcactg cactgaacat catccactac    1500
atgcacgaca gtacagcta cgaagcctct ctgatggcgc tgcacgaccg tgacgttatc    1560
cgcaccatgg cgtgtggtat cgctggtctg tccgttgctg ctgactccct gtctgcaatc    1620
aaatatgcga agttaaaacc gattcgtgac gaagacggtc tggctatcga cttcgaaatc    1680
gaaggcgaat accgcagtt tggtaacaat gatccgcgtg tagatgacct ggctgttgac    1740
ctggtagaac gtttcatgaa gaaaattcag aaactgcaca cctaccgtga cgctatcccg    1800
actcagtctg ttctgaccat cacttctaac gttgtgtatg gtaagaaaac tggtaacacc    1860
ccagacggtc gtcgtgctgg cgcgccgttc ggaccgggtg ctaacccgat gcacggtcgt    1920
gaccagaaag gtgctgtagc gtctctgact tccgttgcta aactaccgtt tgcttacgct    1980
aaagatggta tctcctacac cttctctatc gttccgaacg cactgggtaa agacgacgaa    2040
gttcgtaaga ccaacctggc tggtctgatg gatggttact tccaccacga agcatccatc    2100
gaaggtggtc agcacctgaa cgttaacgtg atgaaccgtg aaatgctgct cgacgcgatg    2160
gaaaacccgg aaaaatatcc gcagctgacc atccgtgtat ctggctacgc agtacgtttc    2220
aactcgctga ctaaagaaca gcagcaggac gttattactc gtaccttcac tcaatctatg    2280
```

-continued tab 2283

<210> SEQ ID NO 6
<211> LENGTH: 760
<212> TYPE: PRT
<213> ORGANISM: Escherichia coli
<220> FEATURE:
<221> NAME/KEY: misc_feature
<223> OTHER INFORMATION: pflB

<400> SEQUENCE: 6

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Ala Leu Glu Lys
                85                  90                  95

Val Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Tyr Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350
```

```
Asn Ser Phe Arg Phe Leu Asn Thr Leu Tyr Thr Met Gly Pro Ser Pro
            355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
                420                 425                 430

Phe Gly Ala Arg Ala Asn Leu Ala Lys Thr Met Leu Tyr Ala Ile Asn
                435                 440                 445

Gly Gly Val Asp Glu Lys Leu Lys Met Gln Val Gly Pro Lys Ser Glu
                450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
                500                 505                 510

Ala Leu His Asp Arg Asp Val Ile Arg Thr Met Ala Cys Gly Ile Ala
                515                 520                 525

Gly Leu Ser Val Ala Ala Asp Ser Leu Ser Ala Ile Lys Tyr Ala Lys
                530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
                580                 585                 590

His Thr Tyr Arg Asp Ala Ile Pro Thr Gln Ser Val Leu Thr Ile Thr
                595                 600                 605

Ser Asn Val Val Tyr Gly Lys Lys Thr Gly Asn Thr Pro Asp Gly Arg
    610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
                660                 665                 670

Asn Ala Leu Gly Lys Asp Asp Glu Val Arg Lys Thr Asn Leu Ala Gly
                675                 680                 685

Leu Met Asp Gly Tyr Phe His His Glu Ala Ser Ile Glu Gly Gly Gln
                690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
                740                 745                 750

Thr Arg Thr Phe Thr Gln Ser Met
                755                 760
```

<210> SEQ ID NO 7
<211> LENGTH: 2676
<212> TYPE: DNA
<213> ORGANISM: Escherichia coli
<220> FEATURE:
<221> NAME/KEY: misc_feature
<223> OTHER INFORMATION: adhE

<400> SEQUENCE: 7

| | | | | | |
|---|---|---|---|---|---|
| atggctgtta | ctaatgtcgc | tgaacttaac | gcactcgtag | agcgtgtaaa | aaaagcccag | 60 |
| cgtgaatatg | ccagtttcac | tcaagagcaa | gtagacaaaa | tcttccgcgc | cgccgctctg | 120 |
| gctgctgcag | atgctcgaat | cccactcgcg | aaaatggccg | ttgccgaatc | cggcatgggt | 180 |
| atcgtcgaag | ataaagtgat | caaaaaccac | tttgcttctg | aatatatcta | caacgcctat | 240 |
| aaagatgaaa | aaacctgtgg | tgttctgtct | gaagacgaca | cttttggtac | catcactatc | 300 |
| gctgaaccaa | tcggtattat | tgcggtatc | gttccgacca | ctaacccgac | ttcaactgct | 360 |
| atcttcaaat | cgctgatcag | tctgaagacc | cgtaacgcca | ttatcttctc | cccgcacccg | 420 |
| cgtgcaaaag | atgccaccaa | caaagcggct | gatatcgttc | tgcaggctgc | tatcgctgcc | 480 |
| ggtgctccga | agatctgat | cggctggatc | gatcaacctt | ctgttgaact | gtctaacgca | 540 |
| ctgatgcacc | acccagacat | caacctgatc | ctcgcgactg | gtggtccggg | catggttaaa | 600 |
| gccgcataca | gctccggtaa | accagctatc | ggtgtaggcg | cgggcaacac | tccagttgtt | 660 |
| atcgatgaaa | ctgctgatat | caaacgtgca | gttgcatctg | tactgatgtc | caaaaccttc | 720 |
| gacaacggcg | taatctgtgc | ttctgaacag | tctgttgttg | ttgttgactc | tgtttatgac | 780 |
| gctgtacgtg | aacgttttgc | aacccacggc | ggctatctgt | gcagggtaa | agagctgaaa | 840 |
| gctgttcagg | atgttatcct | gaaaaacggt | gcgctgaacg | cggctatcgt | ggtcagcca | 900 |
| gcctataaaa | ttgctgaact | ggcaggcttc | tctgtaccag | aaaacaccaa | gattctgatc | 960 |
| ggtgaagtga | ccgttgttga | tgaaagcgaa | ccgttcgcac | atgaaaaact | gtccccgact | 1020 |
| ctggcaatgt | accgcgctaa | agatttcgaa | gacgcggtag | aaaaagcaga | gaaactggtt | 1080 |
| gctatgggcg | gtatcggtca | tacctcttgc | ctgtacactg | accaggataa | ccaaccggct | 1140 |
| cgcgtttctt | acttcggtca | gaaaatgaaa | acggctcgta | tcctgattaa | cacccccagcg | 1200 |
| tctcagggtg | gtatcggtga | cctgtataac | ttcaaactcg | caccttccct | gactctgggt | 1260 |
| tgtggttctt | ggggtggtaa | ctccatctct | gaaaacgttg | gtccgaaaca | cctgatcaac | 1320 |
| aagaaaaccg | ttgctaagcg | agctgaaaac | atgttgtggc | acaaacttcc | gaaatctatc | 1380 |
| tacttccgcc | gtggctccct | gccaatcgcg | ctggatgaag | tgattactga | tggccacaaa | 1440 |
| cgtgcgctca | tcgtgactga | ccgcttcctg | ttcaacaatg | ttatgctga | tcagatcact | 1500 |
| tccgtactga | aagcagcagg | cgttgaaact | gaagtcttct | tcgaagtaga | agcggacccg | 1560 |
| accctgagca | tcgttcgtaa | aggtgcagaa | ctggcaaact | ccttcaaacc | agacgtgatt | 1620 |
| atcgcgctgg | gtggtggttc | cccgatggac | gccgcgaaga | tcatgtgggt | tatgtacgaa | 1680 |
| catccggaaa | ctcacttcga | agagctggcg | ctgcgcttta | tggatatccg | taaacgtatc | 1740 |
| tacaagttcc | cgaaaatggg | cgtgaaagcg | aaaatgatcg | ctgtcaccac | cacttctggt | 1800 |
| acaggttctg | aagtcactcc | gtttgcggtt | gtaactgacg | acgctactgg | tcagaaatat | 1860 |
| ccgctggcag | actatgcgct | gactccggat | atggcgattg | tcgacgccaa | cctggttatg | 1920 |
| gacatgccga | agtccctgtg | tgctttcggt | ggtctggacg | cagtaactca | cgccatggaa | 1980 |
| gcttatgttt | ctgtactggc | atctgagttc | tctgatggtc | aggctctgca | ggcactgaaa | 2040 |

-continued

```
ctgctgaaag aatatctgcc agcgtcctac cacgaagggt ctaaaaatcc ggtagcgcgt    2100
gaacgtgttc acagtgcagc gactatcgcg ggtatcgcgt ttgcgaacgc cttcctgggt    2160
gtatgtcact caatggcgca caaactgggt tcccagttcc atattccgca cggtctggca    2220
aacgccctgc tgatttgtaa cgttattcgc tacaatgcga acgacaaccc gaccaagcag    2280
actgcattca gccagtatga ccgtccgcag gctcgccgtc gttatgctga aattgccgac    2340
cacttgggtc tgagcgcacc gggcgaccgt actgctgcta agatcgagaa actgctggca    2400
tggctggaaa cgctgaaagc tgaactgggt attccgaaat ctatccgtga agctggcgtt    2460
caggaagcag acttcctggc gaacgtggat aaactgtctg aagatgcgtt cgatgaccag    2520
tgcaccggcg ctaacccgcg ttacccgctg atctccgagc tgaaacagat cctgctggat    2580
acctactacg tcgtgatta tgtagaaggt gaaactgcag cgaaaaaaga agccgctccg    2640
gctaaagctg agaaaaaagc gaaaaaatcc gcttaa                              2676
```

<210> SEQ ID NO 8
<211> LENGTH: 891
<212> TYPE: PRT
<213> ORGANISM: Escherichia coli
<220> FEATURE:
<221> NAME/KEY: misc_feature
<223> OTHER INFORMATION: adhE

<400> SEQUENCE: 8

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
```

```
              245                 250                 255
Ser Val Tyr Asp Ala Val Arg Glu Arg Phe Ala Thr His Gly Gly Tyr
            260                 265                 270
Leu Leu Gln Gly Lys Glu Leu Lys Ala Val Gln Asp Val Ile Leu Lys
            275                 280                 285
Asn Gly Ala Leu Asn Ala Ala Ile Val Gly Gln Pro Ala Tyr Lys Ile
            290                 295                 300
Ala Glu Leu Ala Gly Phe Ser Val Pro Glu Asn Thr Lys Ile Leu Ile
305                 310                 315                 320
Gly Glu Val Thr Val Val Asp Glu Ser Glu Pro Phe Ala His Glu Lys
                325                 330                 335
Leu Ser Pro Thr Leu Ala Met Tyr Arg Ala Lys Asp Phe Glu Asp Ala
                340                 345                 350
Val Glu Lys Ala Glu Lys Leu Val Ala Met Gly Gly Ile Gly His Thr
                355                 360                 365
Ser Cys Leu Tyr Thr Asp Gln Asp Asn Gln Pro Ala Arg Val Ser Tyr
            370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                405                 410                 415
Leu Thr Leu Gly Cys Gly Ser Trp Gly Gly Asn Ser Ile Ser Glu Asn
                420                 425                 430
Val Gly Pro Lys His Leu Ile Asn Lys Lys Thr Val Ala Lys Arg Ala
            435                 440                 445
Glu Asn Met Leu Trp His Lys Leu Pro Lys Ser Ile Tyr Phe Arg Arg
            450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
                485                 490                 495
Asp Gln Ile Thr Ser Val Leu Lys Ala Ala Gly Val Glu Thr Glu Val
            500                 505                 510
Phe Phe Glu Val Glu Ala Asp Pro Thr Leu Ser Ile Val Arg Lys Gly
            515                 520                 525
Ala Glu Leu Ala Asn Ser Phe Lys Pro Asp Val Ile Ile Ala Leu Gly
            530                 535                 540
Gly Gly Ser Pro Met Asp Ala Ala Lys Ile Met Trp Val Met Tyr Glu
545                 550                 555                 560
His Pro Glu Thr His Phe Glu Glu Leu Ala Leu Arg Phe Met Asp Ile
                565                 570                 575
Arg Lys Arg Ile Tyr Lys Phe Pro Lys Met Gly Val Lys Ala Lys Met
            580                 585                 590
Ile Ala Val Thr Thr Thr Ser Gly Thr Gly Ser Glu Val Thr Pro Phe
            595                 600                 605
Ala Val Val Thr Asp Asp Ala Thr Gly Gln Lys Tyr Pro Leu Ala Asp
            610                 615                 620
Tyr Ala Leu Thr Pro Asp Met Ala Ile Val Asp Ala Asn Leu Val Met
625                 630                 635                 640
Asp Met Pro Lys Ser Leu Cys Ala Phe Gly Gly Leu Asp Ala Val Thr
                645                 650                 655
His Ala Met Glu Ala Tyr Val Ser Val Leu Ala Ser Glu Phe Ser Asp
                660                 665                 670
```

Gly Gln Ala Leu Gln Ala Leu Lys Leu Leu Lys Glu Tyr Leu Pro Ala
              675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Glu Ala Ala Pro
865                 870                 875                 880

Ala Lys Ala Glu Lys Lys Ala Lys Lys Ser Ala
                885                 890

<210> SEQ ID NO 9
<211> LENGTH: 990
<212> TYPE: DNA
<213> ORGANISM: Escherichia coli
<220> FEATURE:
<221> NAME/KEY: misc_feature
<223> OTHER INFORMATION: ldhA

<400> SEQUENCE: 9

```
atgaaactcg ccgtttatag cacaaaacag tacgacaaga agtacctgca acaggtgaac    60
gagtcctttg gctttgagct ggaattttt gactttctgc tgacggaaaa aaccgctaaa    120
actgccaatg gctgcgaagc ggtatgtatt ttcgtaaacg atgacggcag ccgcccggtg    180
ctggaagagc tgaaaaagca cggcgttaaa tatatcgccc tgcgctgtgc cggttttcaat    240
aacgtcgacc ttgacgcggc aaaagaactg gggctgaaag tagtccgtgt tccagcctat    300
gatccagagg ccgttgctga acacgccatc ggtatgatga tgacgctgaa ccgccgtatt    360
caccgcgcgt atcagcgtac ccgtgacgct aacttctctc tggaaggtct gaccggcttt    420
actatgtatg gcaaaacggc aggcgttatc ggtaccggta aaatcggtgt ggcgatgctg    480
cgcattctga aaggttttgg tatgcgtctg ctggcgttcg atccgtatcc aagtgcagcg    540
gcgctggaac tcggtgtgga gtatgtcgat ctgccaaccc tgttctctga atcagacgtt    600
atctctctgc actgcccgct gacaccggaa aactaccatc tgttgaacga agccgccttc    660
gatcagatga aaaatggcgt gatgatcgtc aataccagtc gcggtgcatt gattgattct    720
caggcagcaa ttgaagcgct gaaaaatcag aaaattggtt cgttgggtat ggacgtgtat    780
```

```
gagaacgaac gcgatctatt ctttgaagat aaatccaacg acgtaattca ggatgacgta    840
ttccgtcgcc tgtctgcctg ccacaacgtg ctatttaccg ggcaccaggc attcctgaca    900
gcagaagctc tgaccagtat ttctcagact acgctgcaaa acttaagcaa tctggaaaaa    960
ggcgaaacct gcccgaacga actggtttaa                                     990

<210> SEQ ID NO 10
<211> LENGTH: 329
<212> TYPE: PRT
<213> ORGANISM: Escherichia coli
<220> FEATURE:
<221> NAME/KEY: misc_feature
<223> OTHER INFORMATION: ldhA

<400> SEQUENCE: 10
```

| Met | Lys | Leu | Ala | Val | Tyr | Ser | Thr | Lys | Gln | Tyr | Asp | Lys | Lys | Tyr | Leu |
|---|---|---|---|---|---|---|---|---|---|---|---|---|---|---|---|
| 1 | | | | 5 | | | | | 10 | | | | | 15 | |

| Gln | Gln | Val | Asn | Glu | Ser | Phe | Gly | Phe | Glu | Leu | Glu | Phe | Phe | Asp | Phe |
|---|---|---|---|---|---|---|---|---|---|---|---|---|---|---|---|
| | | | 20 | | | | | 25 | | | | | 30 | | |

| Leu | Leu | Thr | Glu | Lys | Thr | Ala | Lys | Thr | Ala | Asn | Gly | Cys | Glu | Ala | Val |
| | | 35 | | | | | 40 | | | | | 45 | | | |

| Cys | Ile | Phe | Val | Asn | Asp | Asp | Gly | Ser | Arg | Pro | Val | Leu | Glu | Glu | Leu |
| 50 | | | | | 55 | | | | | 60 | | | | | |

| Lys | Lys | His | Gly | Val | Lys | Tyr | Ile | Ala | Leu | Arg | Cys | Ala | Gly | Phe | Asn |
| 65 | | | | | 70 | | | | | 75 | | | | | 80 |

| Asn | Val | Asp | Leu | Asp | Ala | Ala | Lys | Glu | Leu | Gly | Leu | Lys | Val | Val | Arg |
| | | | | 85 | | | | | 90 | | | | | 95 | |

| Val | Pro | Ala | Tyr | Asp | Pro | Glu | Ala | Val | Ala | Glu | His | Ala | Ile | Gly | Met |
| | | | | 100 | | | | | 105 | | | | | 110 | |

| Met | Met | Thr | Leu | Asn | Arg | Arg | Ile | His | Arg | Ala | Tyr | Gln | Arg | Thr | Arg |
| | | | | 115 | | | | | 120 | | | | | 125 | |

| Asp | Ala | Asn | Phe | Ser | Leu | Glu | Gly | Leu | Thr | Gly | Phe | Thr | Met | Tyr | Gly |
| | | 130 | | | | | 135 | | | | | 140 | | | |

| Lys | Thr | Ala | Gly | Val | Ile | Gly | Thr | Gly | Lys | Ile | Gly | Val | Ala | Met | Leu |
| 145 | | | | | 150 | | | | | 155 | | | | | 160 |

| Arg | Ile | Leu | Lys | Gly | Phe | Gly | Met | Arg | Leu | Leu | Ala | Phe | Asp | Pro | Tyr |
| | | | | 165 | | | | | 170 | | | | | 175 | |

| Pro | Ser | Ala | Ala | Ala | Leu | Glu | Leu | Gly | Val | Glu | Tyr | Val | Asp | Leu | Pro |
| | | | | 180 | | | | | 185 | | | | | 190 | |

| Thr | Leu | Phe | Ser | Glu | Ser | Asp | Val | Ile | Ser | Leu | His | Cys | Pro | Leu | Thr |
| | | | | 195 | | | | | 200 | | | | | 205 | |

| Pro | Glu | Asn | Tyr | His | Leu | Leu | Asn | Glu | Ala | Ala | Phe | Asp | Gln | Met | Lys |
| | | 210 | | | | | 215 | | | | | 220 | | | |

| Asn | Gly | Val | Met | Ile | Val | Asn | Thr | Ser | Arg | Gly | Ala | Leu | Ile | Asp | Ser |
| 225 | | | | | 230 | | | | | 235 | | | | | 240 |

| Gln | Ala | Ala | Ile | Glu | Ala | Leu | Lys | Asn | Gln | Lys | Ile | Gly | Ser | Leu | Gly |
| | | | | 245 | | | | | 250 | | | | | 255 | |

| Met | Asp | Val | Tyr | Glu | Asn | Glu | Arg | Asp | Leu | Phe | Phe | Glu | Asp | Lys | Ser |
| | | | | 260 | | | | | 265 | | | | | 270 | |

| Asn | Asp | Val | Ile | Gln | Asp | Val | Phe | Arg | Arg | Leu | Ser | Ala | Cys | His |
| | | 275 | | | | | 280 | | | | | 285 | | | |

| Asn | Val | Leu | Phe | Thr | Gly | His | Gln | Ala | Phe | Leu | Thr | Ala | Glu | Ala | Leu |
| | | 290 | | | | | 295 | | | | | 300 | | | |

| Thr | Ser | Ile | Ser | Gln | Thr | Thr | Leu | Gln | Asn | Leu | Ser | Asn | Leu | Glu | Lys |
| 305 | | | | | 310 | | | | | 315 | | | | | 320 |

Gly Glu Thr Cys Pro Asn Glu Leu Val
            325

<210> SEQ ID NO 11
<211> LENGTH: 2145
<212> TYPE: DNA
<213> ORGANISM: Escherichia coli
<220> FEATURE:
<221> NAME/KEY: misc_feature
<223> OTHER INFORMATION: pta

<400> SEQUENCE: 11

| | | | | |
|---|---|---|---|---|
| gtgtcccgta | ttattatgct | gatccctacc | ggaaccagcg | tcggtctgac | cagcgtcagc | 60 |
| cttggcgtga | tccgtgcaat | ggaacgcaaa | ggcgttcgtc | tgagcgtttt | caaacctatc | 120 |
| gctcagccgc | gtaccggtgg | cgatgcgccc | gatcagacta | cgactatcgt | gcgtgcgaac | 180 |
| tcttccacca | cgacggccgc | tgaaccgctg | aaaatgagct | acgttgaagg | tctgctttcc | 240 |
| agcaatcaga | aagatgtgct | gatggaagag | atcgtcgcaa | actaccacgc | taacaccaaa | 300 |
| gacgctgaag | tcgttctggt | tgaaggtctg | gtcccgacac | gtaagcacca | gtttgcccag | 360 |
| tctctgaact | acgaaatcgc | taaaacgctg | aatgcgaaaa | tcgtcttcgt | tatgtctcag | 420 |
| ggcactgaca | ccccggaaca | gctgaaagag | cgtatcgaac | tgacccgcaa | cagcttcggc | 480 |
| ggtgccaaaa | acaccaacat | caccggcgtt | atcgttaaca | aactgaacgc | accggttgat | 540 |
| gaacagggtc | gtactcgccc | ggatctgtcc | gagatttttcg | acgactcttc | caaagctaaa | 600 |
| gtaaacaatg | ttgatccggc | gaagctgcaa | gaatccagcc | cgctgccggt | tctcggcgct | 660 |
| gtgccgtgga | gctttgacct | gatcgcgact | cgtgcgatcg | atatggctcg | ccacctgaat | 720 |
| gcgaccatca | tcaacgaagg | cgacatcaat | actcgccgcg | ttaaatccgt | cactttctgc | 780 |
| gcacgcagca | ttccgcacat | gctggagcac | ttccgtgccg | gttctctgct | ggtgacttcc | 840 |
| gcagaccgtc | ctgacgtgct | ggtggccgct | gcctggcag | ccatgaacgg | cgtagaaatc | 900 |
| ggtgccctgc | tgctgactgg | cggctacgaa | atggacgcgc | gcatttctaa | actgtgcgaa | 960 |
| cgtgctttcg | ctaccggcct | gccggtattt | atggtgaaca | ccaacacctg | gcagacctct | 1020 |
| ctgagcctgc | agagcttcaa | cctggaagtt | ccggttgacg | atcacgagcg | tatcgagaaa | 1080 |
| gttcaggaat | acgttgctaa | ctacatcaac | gctgactgga | tcgaatctct | gactgccact | 1140 |
| tctgagcgca | gccgtcgtct | gtctccgcct | gcgttccgtt | atcagctgac | tgaacttgcg | 1200 |
| cgcaaagcgg | gcaaacgtat | cgtactgccg | gaaggtgacg | aaccgcgtac | cgttaaagca | 1260 |
| gccgctatct | gtgctgaacg | tggtatcgca | acttgcgtac | tgctgggtaa | tccggcagag | 1320 |
| atcaaccgtg | ttgcagcgtc | tcagggtgta | gaactgggtg | cagggattga | aatcgttgat | 1380 |
| ccagaagtgg | ttcgcgaaag | ctatgttggt | cgtctggtcg | aactgcgtaa | gaacaaaggc | 1440 |
| atgaccgaaa | ccgttgcccg | cgaacagctg | gaagacaacg | tggtgctcgg | tacgctgatg | 1500 |
| ctggaacagg | atgaagttga | tggtctggtt | tccggtgctg | ttcacactac | cgcaaacacc | 1560 |
| atccgtccgc | cgctgcagct | gatcaaaact | gcaccgggca | gctccctggt | atcttccgtg | 1620 |
| ttcttcatgc | tgctgccgga | acaggttttac | gtttacggtg | actgtgcgat | caaccccggat | 1680 |
| ccgaccgctg | aacagctggc | agaaatcgcg | attcagtccg | ctgattccgc | tgcggccttc | 1740 |
| ggtatcgaac | cgcgcgttgc | tatgctctcc | tactccaccg | gtacttctgg | tgcaggtagc | 1800 |
| gacgtagaaa | aagttcgcga | agcaactcgt | ctggcgcagg | aaaaacgtcc | tgacctgatg | 1860 |
| atcgacggtc | cgctgcagta | cgacgctgcg | gtaatggctg | acgttgcgaa | atccaaagcg | 1920 |

-continued

```
ccgaactctc cggttgcagg tcgcgctacc gtgttcatct tcccggatct gaacaccggt      1980
aacaccacct acaaagcggt acagcgttct gccgacctga tctccatcgg cgccgatgctg     2040 cagggtatgc gcaagccggt taacgacctg tcccgtggcg cactggttga cgatatcgtc     2100
tacaccatcg cgctgactgc gattcagtct gcacagcagc agtaa                     2145
```

<210> SEQ ID NO 12
<211> LENGTH: 714
<212> TYPE: PRT
<213> ORGANISM: Escherichia coli
<220> FEATURE:
<221> NAME/KEY: misc_feature
<223> OTHER INFORMATION: pta

<400> SEQUENCE: 12

Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
                20                  25                  30

Arg Leu Ser Val Phe Lys Pro Ile Ala Gln Pro Arg Thr Gly Gly Asp
            35                  40                  45

Ala Pro Asp Gln Thr Thr Thr Ile Val Arg Ala Asn Ser Ser Thr Thr
        50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
    290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
            355                 360                 365

Ile Asn Ala Asp Trp Ile Glu Ser Leu Thr Thr Ser Glu Arg Ser
            370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ala Ile Cys Ala Glu Arg Gly Ile Ala Thr Cys
                420                 425                 430

Val Leu Leu Gly Asn Pro Ala Glu Ile Asn Arg Val Ala Ala Ser Gln
                435                 440                 445

Gly Val Glu Leu Gly Ala Gly Ile Glu Ile Val Asp Pro Glu Val Val
450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
                500                 505                 510

Ala Val His Thr Thr Ala Asn Thr Ile Arg Pro Pro Leu Gln Leu Ile
                515                 520                 525

Lys Thr Ala Pro Gly Ser Ser Leu Val Ser Ser Val Phe Phe Met Leu
530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
                580                 585                 590

Thr Gly Thr Ser Gly Ala Gly Ser Asp Val Glu Lys Val Arg Glu Ala
                595                 600                 605

Thr Arg Leu Ala Gln Glu Lys Arg Pro Asp Leu Met Ile Asp Gly Pro
                610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
                660                 665                 670

Leu Ile Ser Ile Gly Pro Met Leu Gln Gly Met Arg Lys Pro Val Asn
                675                 680                 685

Asp Leu Ser Arg Gly Ala Leu Val Asp Asp Ile Val Tyr Thr Ile Ala
                690                 695                 700

Leu Thr Ala Ile Gln Ser Ala Gln Gln Gln
705                 710

<210> SEQ ID NO 13
<211> LENGTH: 1809
<212> TYPE: DNA

<213> ORGANISM: Escherichia coli
<220> FEATURE:
<221> NAME/KEY: misc_feature
<223> OTHER INFORMATION: frdA

<400> SEQUENCE: 13

| | |
|---|---|
| gtgcaaacct tcaagccga tcttgccatt gtaggcgccg gtggcgcggg attacgtgct | 60 |
| gcaattgctg ccgcgcaggc aaatccgaat gcaaaaatcg cactaatctc aaaagtatac | 120 |
| ccgatgcgta gccataccgt tgctgcagaa gggggctccg ccgctgtcgc gcaggatcat | 180 |
| gacagcttcg aatatcactt tcacgataca gtagcgggtg gcgactggtt gtgtgagcag | 240 |
| gatgtcgtgg attatttcgt ccaccactgc caaccgaaa tgacccaact ggaactgtgg | 300 |
| ggatgcccat ggagccgtcg cccggatggt agcgtcaacg tacgtcgctt cggcggcatg | 360 |
| aaaatcgagc gcacctggtt cgccgccgat aagaccggct tccatatgct gcacacgctg | 420 |
| ttccagacct ctctgcaatt cccgcagatc cagcgttttg acgaacattt cgtgctggat | 480 |
| attctggttg atgatggtca tgttcgcggc ctggtagcaa tgaacatgat ggaaggcacg | 540 |
| ctggtgcaga tccgtgctaa cgcggtcgtt atggctactg gcggtgcggg tcgcgtttat | 600 |
| cgttacaaca ccaacggcgg catcgttacc ggtgacggta tgggtatggc gctaagccac | 660 |
| ggcgttccgc tgcgtgacat ggaattcgtt cagtatcacc caaccggtct gccaggttcc | 720 |
| ggtatcctga tgaccgaagg ctgccgcggt gaaggcggta ttctggtcaa caaaaatggc | 780 |
| taccgttatc tgcaagatta cggcatgggc ccggaaactc gctgggcga ccgaaaaac | 840 |
| aaatatatgg aactgggtcc acgcgacaaa gtttctcagg ccttctggca cgaatggcgt | 900 |
| aaaggcaaca ccatctccac gccgcgtggc gatgtggttt atctcgacct gcgtcacctc | 960 |
| ggcgagaaaa aactgcatga acgtctgccg ttcatctgcg aactggcgaa agcgtacgtt | 1020 |
| ggcgtcgatc cggttaaaga accgattccg gtacgtccga ccgcacacta ccatgggc | 1080 |
| ggtatcgaaa ccgatcagaa ctgtgaaacc cgcattaaag gtctgttcgc cgtgggtgaa | 1140 |
| tgttcctctg ttggtctgca cggtgcaaac cgtctgggtt ctaactccct ggcggaactg | 1200 |
| gtggtcttcg gccgtctggc cggtgaacaa gcgacagagc gtgcagcaac tgccggtaat | 1260 |
| ggcaacgaag cggcaattga agcgcaggca gctggcgttg aacaacgtct gaaagatctg | 1320 |
| gttaaccagg atggcggcga aaactggggcg aagatccgcg acgaaatggg cctggcaatg | 1380 |
| gaagaaggtt gcggtatcta ccgtacgccg gaactgatgc agaaaaccat cgacaagctg | 1440 |
| gcagagctgc aggaacgctt caagcgcgtg cgcatcaccg acacctccag cgtgttcaac | 1500 |
| accgacctgc tctacaccat tgaactgggc cacggtctga cgttgctga atgtatggcg | 1560 |
| cactccgcaa tggcacgtaa agagtcccgc ggcgcacacc agcgtctgga cgaaggttgc | 1620 |
| accgagcgtg acgacgtcaa cttcctcaaa cacacctcg ccttccgcga tgctgatggc | 1680 |
| acgactcgcc tggagtacag cgacgtgaag attactacgc tgccgccagc taaacgcgtt | 1740 |
| tacggtggcg aagcggatgc agccgataag gcggaagcag ccaataagaa ggagaaggcg | 1800 |
| aatggctga | 1809 |

<210> SEQ ID NO 14
<211> LENGTH: 602
<212> TYPE: PRT
<213> ORGANISM: Escherichia coli
<220> FEATURE:
<221> NAME/KEY: misc_feature
<223> OTHER INFORMATION: frdA

<400> SEQUENCE: 14

```
Met Gln Thr Phe Gln Ala Asp Leu Ala Ile Val Gly Ala Gly Gly Ala
1               5                   10                  15

Gly Leu Arg Ala Ala Ile Ala Ala Gln Ala Asn Pro Asn Ala Lys
            20                  25                  30

Ile Ala Leu Ile Ser Lys Val Tyr Pro Met Arg Ser His Thr Val Ala
                35                  40                  45

Ala Glu Gly Gly Ser Ala Ala Val Ala Gln Asp His Asp Ser Phe Glu
        50                  55                  60

Tyr His Phe His Asp Thr Val Ala Gly Gly Asp Trp Leu Cys Glu Gln
65                      70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
                100                 105                 110

Asn Val Arg Arg Phe Gly Gly Met Lys Ile Glu Arg Thr Trp Phe Ala
            115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
                180                 185                 190

Thr Gly Gly Ala Gly Arg Val Tyr Arg Tyr Asn Thr Asn Gly Gly Ile
            195                 200                 205

Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255

Asn Lys Asn Gly Tyr Arg Tyr Leu Gln Asp Tyr Gly Met Gly Pro Glu
            260                 265                 270

Thr Pro Leu Gly Glu Pro Lys Asn Lys Tyr Met Glu Leu Gly Pro Arg
    275                 280                 285

Asp Lys Val Ser Gln Ala Phe Trp His Glu Trp Arg Lys Gly Asn Thr
290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
            340                 345                 350

Pro Thr Ala His Tyr Thr Met Gly Gly Ile Glu Thr Asp Gln Asn Cys
        355                 360                 365

Glu Thr Arg Ile Lys Gly Leu Phe Ala Val Gly Glu Cys Ser Ser Val
    370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415
```

```
Thr Ala Gly Asn Gly Asn Glu Ala Ala Ile Glu Ala Gln Ala Ala Gly
            420                 425                 430

Val Glu Gln Arg Leu Lys Asp Leu Val Asn Gln Asp Gly Gly Glu Asn
        435                 440                 445

Trp Ala Lys Ile Arg Asp Glu Met Gly Leu Ala Met Glu Glu Gly Cys
    450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
            500                 505                 510

Leu Asn Val Ala Glu Cys Met Ala His Ser Ala Met Ala Arg Lys Glu
        515                 520                 525

Ser Arg Gly Ala His Gln Arg Leu Asp Glu Gly Cys Thr Glu Arg Asp
    530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
            580                 585                 590

Ala Ala Asn Lys Lys Glu Lys Ala Asn Gly
        595                 600

<210> SEQ ID NO 15
<211> LENGTH: 1119
<212> TYPE: DNA
<213> ORGANISM: Geobacillus stearothermophilus
<220> FEATURE:
<221> NAME/KEY: misc_feature
<223> OTHER INFORMATION: alaD

<400> SEQUENCE: 15
atgaaaattg gcatccctaa agagattaag aacaatgaaa accgtgtagc aatcaccccg      60
gcaggtgtta tgactctggt taaagcgggc cacgatgtgt acgtcgaaac cgaagcgggt     120
gccggcagcg gcttcagcga cagcgagtat gagaaggcgg gtgcggttat tgtgactaag     180
gcggaggacg cttgggcagc cgaaatggtt ctgaaggtga agaaccgct ggcggaggag      240 tttcgctatt ttcgtccggg tctgattttg ttcacctacc tgcacctggc tgcggccgag     300
gcgctgacca aggcactggt ggagcagaag gttgttggca tcgcgtacga aacggttcaa     360
ctggcgaatg gttccctgcc gctgctgacc cctatgtctg aagttgcggg tcgcatgagc     420
gttcaagtcg gcgctcagtt tctggagaaa ccgcacggtg gcaagggcat tttgctgggt     480
ggtgttccgg gtgtccgccg tggtaaagtg acgatcattg gcggtggtac ggccggtacg     540
aacgcggcca agattgccgt aggtctgggt gcagatgtga ccattctgga catcaacgcg     600
gaacgtttgc gtgagctgga cgacctgttt ggcgaccaag tcaccaccct gatgagcaac     660
agctaccaca tcgcggagtg cgtccgtgaa agcgatttgg tcgttggtgc ggtgctgatc     720
ccgggtgcaa agccccgaa actggtgacc gaggagatgt ccgtagcat gaccccgggt       780 tcggttctgg tcgacgtggc aattgaccag ggcggtatct tcgaaaccac cgaccgcgtc     840
acgacccatg atgacccgac ctatgtgaaa catggcgtgg ttcactatgc ggtcgcgaat     900
atgccgggtg cagtgccgcg cacgtccacg ttcgcgctga cgaacgtgac gattccatac     960
```

```
gctctgcaga tcgccaataa gggctatcgt gcggcgtgtc tggataatcc ggcattgctg    1020
aaaggcatca ataccctgga tggtcatatc gtttacgagg ctgtggctgc agcacacaac    1080
atgccgtaca ctgatgtcca tagcttgctg caaggctaa                          1119
```

<210> SEQ ID NO 16
<211> LENGTH: 372
<212> TYPE: PRT
<213> ORGANISM: Geobacillus stearothermophilus
<220> FEATURE:
<221> NAME/KEY: misc_feature
<223> OTHER INFORMATION: alaD

<400> SEQUENCE: 16

Met Lys Ile Gly Ile Pro Lys Glu Ile Lys Asn Asn Glu Asn Arg Val
1               5                   10                  15

Ala Ile Thr Pro Ala Gly Val Met Thr Leu Val Lys Ala Gly His Asp
            20                  25                  30

Val Tyr Val Glu Thr Glu Ala Gly Ala Gly Ser Gly Phe Ser Asp Ser
        35                  40                  45

Glu Tyr Glu Lys Ala Gly Ala Val Ile Val Thr Lys Ala Glu Asp Ala
    50                  55                  60

Trp Ala Ala Glu Met Val Leu Lys Val Lys Glu Pro Leu Ala Glu Glu
65                  70                  75                  80

Phe Arg Tyr Phe Arg Pro Gly Leu Ile Leu Phe Thr Tyr Leu His Leu
                85                  90                  95

Ala Ala Ala Glu Ala Leu Thr Lys Ala Leu Val Glu Gln Lys Val Val
            100                 105                 110

Gly Ile Ala Tyr Glu Thr Val Gln Leu Ala Asn Gly Ser Leu Pro Leu
        115                 120                 125

Leu Thr Pro Met Ser Glu Val Ala Gly Arg Met Ser Val Gln Val Gly
    130                 135                 140

Ala Gln Phe Leu Glu Lys Pro His Gly Gly Lys Gly Ile Leu Leu Gly
145                 150                 155                 160

Gly Val Pro Gly Val Arg Arg Gly Lys Val Thr Ile Ile Gly Gly Gly
                165                 170                 175

Thr Ala Gly Thr Asn Ala Ala Lys Ile Ala Val Gly Leu Gly Ala Asp
            180                 185                 190

Val Thr Ile Leu Asp Ile Asn Ala Glu Arg Leu Arg Glu Leu Asp Asp
        195                 200                 205

Leu Phe Gly Asp Gln Val Thr Thr Leu Met Ser Asn Ser Tyr His Ile
    210                 215                 220

Ala Glu Cys Val Arg Glu Ser Asp Leu Val Val Gly Ala Val Leu Ile
225                 230                 235                 240

Pro Gly Ala Lys Ala Pro Lys Leu Val Thr Glu Glu Met Val Arg Ser
                245                 250                 255

Met Thr Pro Gly Ser Val Leu Val Asp Val Ala Ile Asp Gln Gly Gly
            260                 265                 270

Ile Phe Glu Thr Thr Asp Arg Val Thr Thr His Asp Asp Pro Thr Tyr
        275                 280                 285

Val Lys His Gly Val Val His Tyr Ala Val Ala Asn Met Pro Gly Ala
    290                 295                 300

Val Pro Arg Thr Ser Thr Phe Ala Leu Thr Asn Val Thr Ile Pro Tyr
305                 310                 315                 320

Ala Leu Gln Ile Ala Asn Lys Gly Tyr Arg Ala Ala Cys Leu Asp Asn
                325                 330                 335

Pro Ala Leu Leu Lys Gly Ile Asn Thr Leu Asp Gly His Ile Val Tyr
                340                 345                 350

Glu Ala Val Ala Ala Ala His Asn Met Pro Tyr Thr Asp Val His Ser
            355                 360                 365

Leu Leu Gln Gly
    370

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ackA-pta-check1

<400> SEQUENCE: 17
actgcggtag ttcttcactg                                          20

<210> SEQ ID NO 18
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ackA-pta-check2

<400> SEQUENCE: 18
agtacctttc tggtttagcc g                                        21

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ackA-pta-check3

<400> SEQUENCE: 19
gatagcagaa acggaaccac                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ackA-pta-check4

<400> SEQUENCE: 20
ggtgctgttc acactaccgc                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ackA-pta-check5

<400> SEQUENCE: 21
tgacgagatt actgctgctg                                        20

<210> SEQ ID NO 22
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ackA-pta-check6

<400> SEQUENCE: 22
atttccggtt cagatatccg c                                      21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-adhE-check1

<400> SEQUENCE: 23
gggttgacca gcgcaaataa c                                      21

<210> SEQ ID NO 24
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-adhE-check2

<400> SEQUENCE: 24
cagaagtgag taatcttgct tac                                    23

<210> SEQ ID NO 25
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-adhE-check3

<400> SEQUENCE: 25
gatcacttta tcttcgacga tac                                    23

<210> SEQ ID NO 26
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-adhE-check4

<400> SEQUENCE: 26

-continued gcgaacgtgg ataaactgtc tg                                                22

<210> SEQ ID NO 27
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-adhE-check5

<400> SEQUENCE: 27
gctcttaagc accgacgttg ac                                                22

<210> SEQ ID NO 28
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-adhE-check6

<400> SEQUENCE: 28
gtcggctcat taacggctat tc                                                22

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-frd-check1

<400> SEQUENCE: 29
gacggatctc cgccataatc                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-frd-check2

<400> SEQUENCE: 30
tcgccacccg ctactgtatc                                                   20

<210> SEQ ID NO 31
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-frd-check3

<400> SEQUENCE: 31
caaagcgttc tgacgaaccg g                                                 21

<210> SEQ ID NO 32

```
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-frd-check4

<400> SEQUENCE: 32
tgtgcgatgc acaatatcgt tg                                              22

<210> SEQ ID NO 33
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-pflB-check1

<400> SEQUENCE: 33
ttggttgggt tgacatactg g                                               21

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-pflB-check2

<400> SEQUENCE: 34
tgaacttcat cactgataac c                                               21

<210> SEQ ID NO 35
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-pflB-check3

<400> SEQUENCE: 35
ttcaaaggag tgaatgcgac c                                               21

<210> SEQ ID NO 36
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-pflB-check4

<400> SEQUENCE: 36
gtcgcggtta tgacaataca gg                                              22

<210> SEQ ID NO 37
<211> LENGTH: 22
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<223> OTHER INFORMATION: P395-ldhA-check1

<400> SEQUENCE: 37
taccgtgccg acgttcaata ac                                              22

<210> SEQ ID NO 38
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ldhA-check2

<400> SEQUENCE: 38
catcagcagg cttagcgcaa c                                               21

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ldhA-check3

<400> SEQUENCE: 39
acctttacgc gtaatgcgtg                                                 20

<210> SEQ ID NO 40
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-ldhA-check4

<400> SEQUENCE: 40
accgtttacg ctttccagca c                                               21

<210> SEQ ID NO 41
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-csc-check1

<400> SEQUENCE: 41
cgaattatcg atctcgctca ac                                              22

<210> SEQ ID NO 42
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-csc-check2
```

```
<400> SEQUENCE: 42
cgtctatatt gctgaaggta cag                                              23

<210> SEQ ID NO 43
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P395-csc-check3

<400> SEQUENCE: 43
tcgaaggtcc attcacgcaa c                                                21

<210> SEQ ID NO 44
<211> LENGTH: 20
<212> TYPE: DNA
<213> ORGANISM: Artificial Sequencel
<220> FEATURE:
<223> OTHER INFORMATION: Synthetic polynucleotide
<220> FEATURE:
<221> NAME/KEY: misc_feature
<223> OTHER INFORMATION: P395-csc-check4

<400> SEQUENCE: 44
gattcccacc gcaacgttag                                                  20

<210> SEQ ID NO 45
<211> LENGTH: 987
<212> TYPE: DNA
<213> ORGANISM: Escherichia coli
<220> FEATURE:
<221> NAME/KEY: misc_feature
<223> OTHER INFORMATION: zipA

<400> SEQUENCE: 45
atgatgcagg atttgcgtct gatattaatc attgttggcg cgatcgccat aatcgcttta      60
ctggtacatg gtttctggac cagccgtaaa gaacgatctt ctatgttccg cgatcggcca     120
ttaaaacgaa tgaagtcaaa cgtgacgac gattcttatg acgaggatgt cgaagatgat     180
gagggcgttg gtgaggttcg tgttcaccgc gtgaatcatg ccccggctaa cgctcaggag     240
catgaggctg ctcgtccgtc gccgcaacac cagtaccaac gccttatgc gtctgcgcag     300 ccgcgtcaac cggtccagca gccgcctgaa gcgcaggtac gccgcaaca tgctccgcgt     360 ccagcgcagc cggtgcagca gcctgcctat cagccgcagc ctgaacagcc gttgcagcag     420
ccagtttcgc cacaggtcgc gccagcgccg cagcctgtgc attcagcacc gcaaccggca     480
caacaggctt tccagcctgc agaacccgta gcggcaccac agcctgagcc tgtagcggaa     540
ccggctccag ttatggataa accgaagcgc aaagaagcgg tgattatcat gaacgtcgcg     600
gcgcatcacg gtagcgagct aaacggtgaa ctgcttctta acagcattca acaagcgggc     660 ttcattttg gcgatatgaa tatttaccat cgtcatctta gcccggatgg cagcggcccg     720
gcgttattca gcctggcgaa tatggtgaaa ccgggaacct tgatcctga atgaaggat       780 ttcactactc cgggtgtcac catctttatg caggtaccgt cttacggtga cgagctgcag     840
aacttcaagc tgatgctgca atctgcgcag catattgccg atgaagtggg cggtgtcgtg     900
cttgacgatc agcgccgtat gatgactccg cagaaattgc gcgagtacca ggacatcatc     960
cgcgaagtca aagacgccaa cgcctga                                         987
```

-continued

```
<210> SEQ ID NO 46
<211> LENGTH: 328
<212> TYPE: PRT
<213> ORGANISM: Escherichia coli
<220> FEATURE:
<221> NAME/KEY: MISC_FEATURE
<223> OTHER INFORMATION: zipA

<400> SEQUENCE: 46

Met Met Gln Asp Leu Arg Leu Ile Leu Ile Ile Val Gly Ala Ile Ala
1               5                   10                  15

Ile Ile Ala Leu Leu Val His Gly Phe Trp Thr Ser Arg Lys Glu Arg
            20                  25                  30

Ser Ser Met Phe Arg Asp Arg Pro Leu Lys Arg Met Lys Ser Lys Arg
        35                  40                  45

Asp Asp Asp Ser Tyr Asp Glu Asp Val Glu Asp Glu Gly Val Gly
    50                  55                  60

Glu Val Arg Val His Arg Val Asn His Ala Pro Ala Asn Ala Gln Glu
65                  70                  75                  80

His Glu Ala Ala Arg Pro Ser Pro Gln His Gln Tyr Gln Pro Pro Tyr
                85                  90                  95

Ala Ser Ala Gln Pro Arg Gln Pro Val Gln Gln Pro Pro Glu Ala Gln
            100                 105                 110

Val Pro Pro Gln His Ala Pro Arg Pro Ala Gln Pro Val Gln Gln Pro
        115                 120                 125

Ala Tyr Gln Pro Gln Pro Glu Gln Pro Leu Gln Gln Pro Val Ser Pro
    130                 135                 140

Gln Val Ala Pro Ala Pro Gln Pro Val His Ser Ala Pro Gln Pro Ala
145                 150                 155                 160

Gln Gln Ala Phe Gln Pro Ala Glu Pro Val Ala Ala Pro Gln Pro Glu
                165                 170                 175

Pro Val Ala Glu Pro Ala Pro Val Met Asp Lys Pro Lys Arg Lys Glu
            180                 185                 190

Ala Val Ile Ile Met Asn Val Ala Ala His His Gly Ser Glu Leu Asn
        195                 200                 205

Gly Glu Leu Leu Leu Asn Ser Ile Gln Gln Ala Gly Phe Ile Phe Gly
    210                 215                 220

Asp Met Asn Ile Tyr His Arg His Leu Ser Pro Asp Gly Ser Gly Pro
225                 230                 235                 240

Ala Leu Phe Ser Leu Ala Asn Met Val Lys Pro Gly Thr Phe Asp Pro
                245                 250                 255

Glu Met Lys Asp Phe Thr Thr Pro Gly Val Thr Ile Phe Met Gln Val
            260                 265                 270

Pro Ser Tyr Gly Asp Glu Leu Gln Asn Phe Lys Leu Met Leu Gln Ser
        275                 280                 285

Ala Gln His Ile Ala Asp Glu Val Gly Gly Val Val Leu Asp Asp Gln
    290                 295                 300

Arg Arg Met Met Thr Pro Gln Lys Leu Arg Glu Tyr Gln Asp Ile Ile
305                 310                 315                 320

Arg Glu Val Lys Asp Ala Asn Ala
                325

<210> SEQ ID NO 47
<211> LENGTH: 987
<212> TYPE: DNA
```

<213> ORGANISM: Escherichia coli
<220> FEATURE:
<221> NAME/KEY: misc_feature
<223> OTHER INFORMATION: zipA Mut

<400> SEQUENCE: 47

```
atgatgcagg atttgcgtct gatattaatc attgttggcg cgatcgccat aatcgcttta    60
ctggtacatg gtttctggac cagccgtaaa gaacgatctt ctatgttccg cgatcggcca   120
ttaaaacgaa tgaagtcaaa acgtgacgac gattcttatg acgaggatgt cgaagatgat   180
gagggcgttg gtgaggttcg tgttcaccgc gtgaatcatg ccccggctaa cgctcaggag   240
catgaggctg ctcgtccgtc gccgcaacac cagtaccaac cgccttatgc gtctgcgcag   300
ccgcgtcaac cggtccagca gccgcctgaa gcgcaggtac cgccgcaaca tgctccgcgt   360
ccagcgcagc cggtgcagca gcctgcctat cagccgcagc ctgaacagcc gttgcagcag   420
ccagtttcgc cacaggtcgc gccagcgccg cagcctgtgc attcagcacc gcaaccggca   480
caacaggctt tccagcctgc agaacccgta gcggcaccac agcctgagcc tgtagcggaa   540
ccggctccag ttatggataa accgaagcgc aaagaagcgg tgattatcat gaacgtcgcg   600
gcgcatcacg gtagcgagct aaacggtgaa ctgcttctta acagcattca acaagcgggc   660
ttcattttg gcgatatgaa tatttaccat cgtcatctta gcccggatgg cagcggcccg   720
gcgttattca gcctggcgaa tatggtgaaa ccgggaacct ttgatcctga atgaaggat   780
ttcactactc cgggtgtcac catctttatg caggtaccgt cttacggtga cgagctgcag   840
aacttcaagc tgatgctgca atctgcgcag catattgccg atgaagtggg cggtgtcgtg   900
cttgacgatc agggccgtat gatgactccg cagaaattgc gcgagtacca ggacatcatc   960
cgcgaagtca agacgccaa cgcctga                                        987
```

<210> SEQ ID NO 48
<211> LENGTH: 328
<212> TYPE: PRT
<213> ORGANISM: Escherichia coli
<220> FEATURE:
<221> NAME/KEY: MISC_FEATURE
<223> OTHER INFORMATION: zipA Mut

<400> SEQUENCE: 48

```
Met Met Gln Asp Leu Arg Leu Ile Leu Ile Ile Val Gly Ala Ile Ala
1               5                   10                  15

Ile Ile Ala Leu Leu Val His Gly Phe Trp Thr Ser Arg Lys Glu Arg
            20                  25                  30

Ser Ser Met Phe Arg Asp Arg Pro Leu Lys Arg Met Lys Ser Lys Arg
        35                  40                  45

Asp Asp Asp Ser Tyr Asp Glu Asp Val Glu Asp Asp Glu Gly Val Gly
    50                  55                  60

Glu Val Arg Val His Arg Val Asn His Ala Pro Ala Asn Ala Gln Glu
65                  70                  75                  80

His Glu Ala Ala Arg Pro Ser Pro Gln His Gln Tyr Gln Pro Pro Tyr
                85                  90                  95

Ala Ser Ala Gln Pro Arg Gln Pro Val Gln Gln Pro Pro Glu Ala Gln
            100                 105                 110

Val Pro Pro Gln His Ala Pro Arg Pro Ala Gln Pro Val Gln Gln Pro
        115                 120                 125

Ala Tyr Gln Pro Gln Pro Glu Gln Pro Leu Gln Gln Pro Val Ser Pro
    130                 135                 140
```

```
Gln Val Ala Pro Ala Pro Gln Pro Val His Ser Ala Pro Gln Pro Ala
145                 150                 155                 160

Gln Gln Ala Phe Gln Pro Ala Glu Pro Val Ala Ala Pro Gln Pro Glu
                165                 170                 175

Pro Val Ala Glu Pro Ala Pro Val Met Asp Lys Pro Lys Arg Lys Glu
            180                 185                 190

Ala Val Ile Ile Met Asn Val Ala Ala His His Gly Ser Glu Leu Asn
        195                 200                 205

Gly Glu Leu Leu Asn Ser Ile Gln Gln Ala Gly Phe Ile Phe Gly
    210                 215                 220

Asp Met Asn Ile Tyr His Arg His Leu Ser Pro Asp Gly Ser Gly Pro
225                 230                 235                 240

Ala Leu Phe Ser Leu Ala Asn Met Val Lys Pro Gly Thr Phe Asp Pro
                245                 250                 255

Glu Met Lys Asp Phe Thr Thr Pro Gly Val Thr Ile Phe Met Gln Val
            260                 265                 270

Pro Ser Tyr Gly Asp Glu Leu Gln Asn Phe Lys Leu Met Leu Gln Ser
        275                 280                 285

Ala Gln His Ile Ala Asp Glu Val Gly Val Val Leu Asp Asp Gln
    290                 295                 300

Gly Arg Met Met Thr Pro Gln Lys Leu Arg Glu Tyr Gln Asp Ile Ile
305                 310                 315                 320

Arg Glu Val Lys Asp Ala Asn Ala
                325

<210> SEQ ID NO 49
<211> LENGTH: 1425
<212> TYPE: DNA
<213> ORGANISM: Escherichia coli
<220> FEATURE:
<221> NAME/KEY: misc_feature
<223> OTHER INFORMATION: lpd

<400> SEQUENCE: 49
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atccttctca aagcactgct gcacgtagca     180
aaagttatcg aagaagccaa agcgctggct gaacacggta tcgtcttcgg cgaaccgaaa     240
accgatattg acaagattcg tacctggaaa gagaaagtga tcaatcagct gaccggtggt     300
ctggctggta tggcgaaagg ccgcaaagtc aaagtggtca acggtctggg taaatttacc     360
ggggctaaca ccctggaagt tgaaggtgag aacggtaaaa ccgtgatcaa cttcgacaac     420
gcgatcattg cagcgggttc tcgcccgatc caactgccgt ttattccgca tgaagatccg     480
cgtatctggg actccactga cgcgctggaa ctgaaagaag taccagaacg cctgctggta     540
atgggtggcg gtatcatcgg tctggaaatg ggcaccgtat accacgcgct gggttcacag     600
attgacgtgg ttgaaatgtt cgaccaggtt atcccggcag ctgacaaaga catcgttaaa     660
gtcttcacca gcgtatcag caagaaattc aacctgatgc tggaaaccaa agttaccgcc     720
gttgaagcga agaagacgg tatttatgtg acgatggaag caaaaaagc acccgctgaa     780 ccgcagcgtt acgacgccgt gctggtagcg attggtcgtg tgccgaacgg taaaaaccct c    840 gacgcaggca agctggcgt ggaagtggac accgtggtt tcatccgcgt tgacaaacag     900
ctgcgtacca acgtaccgca catctttgct atcggcgata tcgtcggtca gccgatgctg     960
```

-continued

```
gcacacaaag gtgttcacga aggtcacgtt gccgctgaag ttatcgccgg taagaaacac     1020
tacttcgatc cgaaagttat cccgtccatc gcctataccg aaccagaagt tgcatgggta     1080
ggtctgactg agaaagaagc gaaagagaaa ggcatcagct atgaaaccgc caccttcccg     1140
tgggctgctt ctggtcgtgc tatcgcttcc gactgcgcag acggtatgac caagctgatt     1200
ttcgacaaag aatctcaccg tgtgatcggt ggtgcgattg tcggtaccaa cggcggcgag     1260
ctgctgggtg aaatcggcct ggcaatcgaa atgggttgtg atgctgaaga catcgcactg     1320
accatccacg cgcacccgac tctgcacgag tctgtgggcc tggcggcaga agtgttcgaa     1380
ggtagcatta ccgacctgcc gaacccgaaa gcgaagaaga agtaa                     1425
```

<210> SEQ ID NO 50
<211> LENGTH: 474
<212> TYPE: PRT
<213> ORGANISM: Escherichia coli
<220> FEATURE:
<221> NAME/KEY: MISC_FEATURE
<223> OTHER INFORMATION: lpd

<400> SEQUENCE: 50

```
Met Ser Thr Glu Ile Lys Thr Gln Val Val Leu Gly Ala Gly Pro
1               5                  10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
```

```
            275                 280                 285
Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 51
<211> LENGTH: 1425
<212> TYPE: DNA
<213> ORGANISM: Escherichia coli
<220> FEATURE:
<221> NAME/KEY: misc_feature
<223> OTHER INFORMATION: lpd Mut

<400> SEQUENCE: 51
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta agcactgct  gcacgtagca     180 aaagttatcg aagaagccaa agcgctgcct gaacacggta tcgtcttcgg cgaaccgaaa     240
accgatattg acaagattcg tacctggaaa gagaaagtga tcaatcagct gaccggtggt     300
ctggctggta tggcgaaagg ccgcaaagtc aaagtggtca acggtctggg taaatttacc     360
ggggctaaca ccctggaagt tgaaggtgag aacggtaaaa ccgtgatcaa cttcgacaac     420
gcgatcattg cagcgggttc tcgcccgatc caactgccgt ttattccgca tgaagatccg     480
cgtatctggg actccactga cgcgctggaa ctgaaagaag taccagaacg cctgctggta     540
atgggtggcg gtatcatcgg tctggaaatg ggcaccgtat accacgcgct gggttcacag     600
attgacgtgg ttgaaatgtt cgaccaggtt atcccggcag ctgacaaaga catcgttaaa     660
gtcttcacca agcgtatcag caagaaattc aacctgatgc tggaaccaa  agttaccgcc     720 gttgaagcga agaagacgg  tatttatgtg acgatggaag gcaaaaaagc acccgctgaa     780
ccgcagcgtt acgacgccgt gctggtagcg attggtcgtg tgccgaacgg taaaaacctc     840
gacgcaggca agctggcgt  ggaagtggac gaccgtggtt tcatccgcgt tgacaaacag     900
```

```
ctgcgtacca acgtaccgca catctttgct atcggcgata tcgtcggtca gccgatgctg    960
gcacacaaag gtgttcacga aggtcacgtt gccgctgaag ttatcgccgg taagaaacac   1020
tacttcgatc cgaaagttat cccgtccatc gcctataccg aaccagaagt tgcatgggta   1080
ggtctgactg agaagaagc gaaagagaaa ggcatcagct atgaaaccgc caccttcccg   1140
tgggctgctt ctggtcgtgc tatcgcttcc gactgcgcag acggtatgac caagctgatt   1200
ttcgacaaag aatctcaccg tgtgatcggt ggtgcgattg tcggtaccaa cggcggcgag   1260
ctgctgggtg aaatcggcct ggcaatcgaa atgggttgtg atgctgaaga catcgcactg   1320
accatccacg cgcacccgac tctgcacgag tctgtgggcc tggcggcaga agtgttcgaa   1380
ggtagcatta ccgacctgcc gaacccgaaa gcgaagaaga agtaa             1425
```

<210> SEQ ID NO 52
<211> LENGTH: 474
<212> TYPE: PRT
<213> ORGANISM: Escherichia coli
<220> FEATURE:
<221> NAME/KEY: MISC_FEATURE
<223> OTHER INFORMATION: lpd Mut

<400> SEQUENCE: 52

```
Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Pro Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270
```

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
                340                 345                 350

Thr Glu Pro Glu Val Ala Trp Val Gly Leu Thr Glu Lys Glu Ala Lys
                355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
                420                 425                 430

Cys Asp Ala Glu Asp Ile Ala Leu Thr Ile His Ala His Pro Thr Leu
                435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 53
<211> LENGTH: 210
<212> TYPE: DNA
<213> ORGANISM: Escherichia coli
<220> FEATURE:
<221> NAME/KEY: misc_feature
<223> OTHER INFORMATION: ldhA WT Promoter

<400> SEQUENCE: 53
catgggtagt taatatcctg atttagcgaa aaattaagca ttcaatacgg gtattgtggc      60
atgtttaacc gttcagttga aggttgcgcc tacactaagc atagttgttg atgaattttt     120
caatatcgcc atagctttca attatatttg aaattttgta aaatattttt agtagcttaa     180
atgtgattca acatcactgg agaaagtctt                                      210

<210> SEQ ID NO 54
<211> LENGTH: 269
<212> TYPE: DNA
<213> ORGANISM: Escherichia coli
<220> FEATURE:
<221> NAME/KEY: misc_feature
<223> OTHER INFORMATION: ldhA mut Promoter

<400> SEQUENCE: 54
catagtaaat tcccccacca gtttaaccgg cggctgattt tcaaacgcga cgacatccag      60
ttcgctgact gtaagttgtt gcccttcag ctggccttga aatttaactt tttcgccctg     120
ataacgcagt tgctggatat cagaggttaa tgcgagagag agttttccct gccattcctg     180
ccagggagaa aaaatcagtt tatcgatatt gattttgtaa aatattttta gtagcttaaa     240
tgtgattcaa catcactgga gaaagtctt                                       269

<210> SEQ ID NO 55
<211> LENGTH: 269
<212> TYPE: DNA
<213> ORGANISM: Escherichia coli
<220> FEATURE:
<221> NAME/KEY: misc_feature
<223> OTHER INFORMATION: ldhA mut Promoter fragment

<400> SEQUENCE: 55
catagtaaat tcccccacca gtttaaccgg cggctgattt tcaaacgcga cgacatccag    60
ttcgctgact gtaagttgtt gccctttcag ctggccttga aatttaactt tttcgccctg   120
ataacgcagt tgctggatat cagaggttaa tgcgagagag agttttccct gccattcctg   180
ccagggagaa aaaatcagtt tatcgatatt gattttgtaa aatattttta gtagcttaaa   240
tgtgattcaa catcactgga gaaagtctt                                     269

<210> SEQ ID NO 56
<211> LENGTH: 450
<212> TYPE: DNA
<213> ORGANISM: Escherichia coli
<220> FEATURE:
<221> NAME/KEY: misc_feature
<223> OTHER INFORMATION: ygaW Mut2

<400> SEQUENCE: 56
atgttctcac cgaactcacg cttgcgtcat gcagttgcag atacgttcgc gatggttgtt    60
tactgttctg tcgtgaacat gtgtattgaa gttttcctct ccggaatgag cttcgaacag   120 tcttttttatt ccagattggt agcgattccg gtgaacatct taattgcatg gccatacggt   180
atgtaccgtg atctgtttat gcgcgcggca cgcaaagtta gcccgtcggg ctggataaaa   240
aatctggctg atatcctggc ttatgtgacg ttccagtcac cggtgtatgt ggcgatcttg   300
ttagtggtgg gcgcagactg gcatcagatt atggcggcgg tcagttcaaa catcgttgtt   360
tcgatgttga tgggggcggt ttatggctac ttcctcgatt attgccgccg actgtttaaa   420
gtcagccgtt accagcaggt aaaagcctga                                    450

<210> SEQ ID NO 57
<211> LENGTH: 149
<212> TYPE: PRT
<213> ORGANISM: Escherichia coli
<220> FEATURE:
<221> NAME/KEY: MISC_FEATURE
<223> OTHER INFORMATION: ygaW Mut2

<400> SEQUENCE: 57

Met Phe Ser Pro Asn Ser Arg Leu Arg His Ala Val Ala Asp Thr Phe
1               5                   10                  15

Ala Met Val Val Tyr Cys Ser Val Val Asn Met Cys Ile Glu Val Phe
            20                  25                  30

Leu Ser Gly Met Ser Phe Glu Gln Ser Phe Tyr Ser Arg Leu Val Ala
        35                  40                  45

Ile Pro Val Asn Ile Leu Ile Ala Trp Pro Tyr Gly Met Tyr Arg Asp
    50                  55                  60

Leu Phe Met Arg Ala Ala Arg Lys Val Ser Pro Ser Gly Trp Ile Lys
65                  70                  75                  80

Asn Leu Ala Asp Ile Leu Ala Tyr Val Thr Phe Gln Ser Pro Val Tyr
                85                  90                  95

Val Ala Ile Leu Leu Val Val Gly Ala Asp Trp His Gln Ile Met Ala

```
            100                 105                 110
Ala Val Ser Ser Asn Ile Val Val Ser Met Leu Met Gly Ala Val Tyr
        115                 120                 125

Gly Tyr Phe Leu Asp Tyr Cys Arg Arg Leu Phe Lys Val Ser Arg Tyr
        130                 135                 140

Gln Gln Val Lys Ala
145

<210> SEQ ID NO 58
<211> LENGTH: 450
<212> TYPE: DNA
<213> ORGANISM: Escherichia coli
<220> FEATURE:
<221> NAME/KEY: misc_feature
<223> OTHER INFORMATION: ygaW Mut3

<400> SEQUENCE: 58
atgttctcac cgcgttcacg cttgcgtcat gcagttgcag atacgttcgc gatggttgtt      60
tactgttctg tcgtgaacat gtgtattgaa gtttcctct ccggaatgag cttcgaacag      120 tcttttatt ccagattggt agcgattccg gtgaacatct taattgcatg gccatacggt      180
atgtaccgtg atctgtttat gcgcgcggca cgcaaagtta gcccgtcggg ctggataaaa      240
aatctggctg atatcctggc ttatgtgacg ttccagtcac cggtgtatgt ggcgatcttg      300
ttagtggtgg gcgcagactg gcatcagatt atggcggcgg tcagttcaaa catcgttgtt      360
tcgatgttga tgggggcggt ttatggctac ttcctcgatt attgccgccg actgtttaaa      420
gtcagccgtt accagcaggt aaaagcctga                                       450

<210> SEQ ID NO 59
<211> LENGTH: 149
<212> TYPE: PRT
<213> ORGANISM: Escherichia coli
<220> FEATURE:
<221> NAME/KEY: MISC_FEATURE
<223> OTHER INFORMATION: ygaW Mut3

<400> SEQUENCE: 59

Met Phe Ser Pro Arg Ser Arg Leu Arg His Ala Val Ala Asp Thr Phe
1               5                   10                  15

Ala Met Val Val Tyr Cys Ser Val Val Asn Met Cys Ile Glu Val Phe
            20                  25                  30

Leu Ser Gly Met Ser Phe Glu Gln Ser Phe Tyr Ser Arg Leu Val Ala
        35                  40                  45

Ile Pro Val Asn Ile Leu Ile Ala Trp Pro Tyr Gly Met Tyr Arg Asp
    50                  55                  60

Leu Phe Met Arg Ala Ala Arg Lys Val Ser Pro Ser Gly Trp Ile Lys
65                  70                  75                  80

Asn Leu Ala Asp Ile Leu Ala Tyr Val Thr Phe Gln Ser Pro Val Tyr
                85                  90                  95

Val Ala Ile Leu Leu Val Val Gly Ala Asp Trp His Gln Ile Met Ala
            100                 105                 110

Ala Val Ser Ser Asn Ile Val Val Ser Met Leu Met Gly Ala Val Tyr
        115                 120                 125

Gly Tyr Phe Leu Asp Tyr Cys Arg Arg Leu Phe Lys Val Ser Arg Tyr
        130                 135                 140

Gln Gln Val Lys Ala
145
```

<210> SEQ ID NO 60
<211> LENGTH: 450
<212> TYPE: DNA
<213> ORGANISM: Escherichia coli
<220> FEATURE:
<221> NAME/KEY: misc_feature
<223> OTHER INFORMATION: ygaW Mut4

<400> SEQUENCE: 60

```
atgttctcac cgtattcacg cttgcgtcat gcagttgcag atacgttcgc gatggttgtt      60
tactgttctg tcgtgaacat gtgtattgaa gttttcctct ccggaatgag cttcgaacag     120
tcttttatt ccagattggt agcgattccg gtgaacatct taattgcatg gccatacggt     180
atgtaccgtg atctgtttat gcgcgcggca cgcaaagtta gcccgtcggg ctggataaaa     240
aatctggctg atatcctggc ttatgtgacg ttccagtcac cggtgtatgt ggcgatcttg     300
ttagtggtgg gcgcagactg gcatcagatt atggcggcgg tcagttcaaa catcgttgtt     360
tcgatgttga tggggcggt ttatggctac ttcctcgatt attgccgccg actgtttaaa     420
gtcagccgtt accagcaggt aaaagcctga                                     450
```

<210> SEQ ID NO 61
<211> LENGTH: 149
<212> TYPE: PRT
<213> ORGANISM: Escherichia coli
<220> FEATURE:
<221> NAME/KEY: MISC_FEATURE
<223> OTHER INFORMATION: ygaW Mut4

<400> SEQUENCE: 61

```
Met Phe Ser Pro Tyr Ser Arg Leu Arg His Ala Val Ala Asp Thr Phe
1               5                   10                  15

Ala Met Val Val Tyr Cys Ser Val Val Asn Met Cys Ile Glu Val Phe
                20                  25                  30

Leu Ser Gly Met Ser Phe Glu Gln Ser Phe Tyr Ser Arg Leu Val Ala
        35                  40                  45

Ile Pro Val Asn Ile Leu Ile Ala Trp Pro Tyr Gly Met Tyr Arg Asp
    50                  55                  60

Leu Phe Met Arg Ala Ala Arg Lys Val Ser Pro Ser Gly Trp Ile Lys
65                  70                  75                  80

Asn Leu Ala Asp Ile Leu Ala Tyr Val Thr Phe Gln Ser Pro Val Tyr
                85                  90                  95

Val Ala Ile Leu Leu Val Val Gly Ala Asp Trp His Gln Ile Met Ala
            100                 105                 110

Ala Val Ser Ser Asn Ile Val Val Ser Met Leu Met Gly Ala Val Tyr
        115                 120                 125

Gly Tyr Phe Leu Asp Tyr Cys Arg Arg Leu Phe Lys Val Ser Arg Tyr
    130                 135                 140

Gln Gln Val Lys Ala
145
```

<210> SEQ ID NO 62
<211> LENGTH: 75
<212> TYPE: DNA
<213> ORGANISM: Artificial sequence
<220> FEATURE:
<223> OTHER INFORMATION: Primer Rec1_1_F

<400> SEQUENCE: 62

```
gttttccctg ccattcctgc cagggagaaa aaatcagttt atcgatattg atgatatcgg      60
```

```
aagccctggg ccaac                                                          75

<210> SEQ ID NO 63
<211> LENGTH: 77
<212> TYPE: DNA
<213> ORGANISM: Artificial sequence
<220> FEATURE:
<223> OTHER INFORMATION: Primer Rec1_1_R

<400> SEQUENCE: 63
ctttctccag tgatgttgaa tcacattta gctactaaaa atattttaca aacacctgag         60
acaacttgtt acagctc                                                        77

<210> SEQ ID NO 64
<211> LENGTH: 74
<212> TYPE: DNA
<213> ORGANISM: Artificial sequence
<220> FEATURE:
<223> OTHER INFORMATION: Primer Rec1_2_F

<400> SEQUENCE: 64
gttttccctg ccattcctgc cagggagaaa aaatcagttt atcgatattg attttgtaaa         60 atattttag tagc                                                            74

<210> SEQ ID NO 65
<211> LENGTH: 74
<212> TYPE: DNA
<213> ORGANISM: Artificial sequence
<220> FEATURE:
<223> OTHER INFORMATION: Primer Rec1_2_R

<400> SEQUENCE: 65
attttcataa gactttctcc agtgatgttg aatcacattt aagctactaa aaatatttta         60
caaaatcaat atcg                                                           74

<210> SEQ ID NO 66
<211> LENGTH: 20
<212> TYPE: DNA
<213> ORGANISM: Artificial sequence
<220> FEATURE:
<223> OTHER INFORMATION: Primer Rec1_seq_F

<400> SEQUENCE: 66
acgcgacgac atccagttcg                                                     20

<210> SEQ ID NO 67
<211> LENGTH: 21
<212> TYPE: DNA
<213> ORGANISM: Artificial sequence
<220> FEATURE:
<223> OTHER INFORMATION: Primer Rec1_seq_R

<400> SEQUENCE: 67
ccggcacccg cttcggtttc g                                                   21

<210> SEQ ID NO 68
<211> LENGTH: 73
<212> TYPE: DNA
<213> ORGANISM: Artificial sequence
<220> FEATURE:
<223> OTHER INFORMATION: Primer Rec1B_1_F

<400> SEQUENCE: 68
```

```
attgtggcat gtttaaccgt tcagttgaag gttgcgccta cactaagcat gatatcggaa      60
gccctgggcc aac                                                         73
```

<210> SEQ ID NO 69
<211> LENGTH: 75
<212> TYPE: DNA
<213> ORGANISM: Artificial sequence
<220> FEATURE:
<223> OTHER INFORMATION: Primer Rec1B_1_R
<400> SEQUENCE: 69

```
ttcaaatata attgaaagct atggcgatat tgaaaaattc atcaacaact cacctgagac      60
aacttgttac agctc                                                       75
```

<210> SEQ ID NO 70
<211> LENGTH: 75
<212> TYPE: DNA
<213> ORGANISM: Artificial sequence
<220> FEATURE:
<223> OTHER INFORMATION: Primer Rec1B_2_F
<400> SEQUENCE: 70

```
cattcaatac gggtattgtg gcatgtttaa ccgttcagtt gaaggttgcg cctacactaa      60
gcattattga ttttg                                                       75
```

<210> SEQ ID NO 71
<211> LENGTH: 75
<212> TYPE: DNA
<213> ORGANISM: Artificial sequence
<220> FEATURE:
<223> OTHER INFORMATION: Primer Rec1B_2_R
<400> SEQUENCE: 71

```
gactttctcc agtgatgttg aatcacattt aagctactaa aaatatttta caaaatcaat      60
aatgcttagt gtagg                                                       75
```

<210> SEQ ID NO 72
<211> LENGTH: 23
<212> TYPE: DNA
<213> ORGANISM: Artificial sequence
<220> FEATURE:
<223> OTHER INFORMATION: Primer Rec1B_seq_F
<400> SEQUENCE: 72

```
ataatcagta ataacagcgc gag                                              23
```

<210> SEQ ID NO 73
<211> LENGTH: 21
<212> TYPE: DNA
<213> ORGANISM: Artificial sequence
<220> FEATURE:
<223> OTHER INFORMATION: Primer Rec1B_seq_R
<400> SEQUENCE: 73

```
ccggcacccg cttcggtttc g                                                21
```

<210> SEQ ID NO 74
<211> LENGTH: 76
<212> TYPE: DNA
<213> ORGANISM: Artificial sequence
<220> FEATURE:
<223> OTHER INFORMATION: Primer Rec1C_1_F
<400> SEQUENCE: 74

```
caccagcggc tggaatacag tcagtgattg ttttggccac caggcgttac cgcgatatcg    60
gaagccctgg gccaac                                                   76
```

<210> SEQ ID NO 75
<211> LENGTH: 77
<212> TYPE: DNA
<213> ORGANISM: Artificial sequence
<220> FEATURE:
<223> OTHER INFORMATION: Primer Rec1C_1_R

<400> SEQUENCE: 75

```
ggtgagattg gcccggttcg ggtaaatggt cgctgggacg gtattcgtct gccacctgag    60
acaacttgtt acagctc                                                  77
```

<210> SEQ ID NO 76
<211> LENGTH: 77
<212> TYPE: DNA
<213> ORGANISM: Artificial sequence
<220> FEATURE:
<223> OTHER INFORMATION: Primer Rec1C_2_F

<400> SEQUENCE: 76

```
ggcgtacagg cagccagcat aaaagatgac gtcaacgcag ccagtaaaat ttgggtagtt    60
aatatcctga tttagcg                                                  77
```

<210> SEQ ID NO 77
<211> LENGTH: 78
<212> TYPE: DNA
<213> ORGANISM: Artificial sequence
<220> FEATURE:
<223> OTHER INFORMATION: Primer Rec1C_2_R

<400> SEQUENCE: 77

```
caatacccgt attgaatgct taattttcg ctaaatcagg atattaacta cccaaatttt    60
actggctgcg ttgacgtc                                                 78
```

<210> SEQ ID NO 78
<211> LENGTH: 30
<212> TYPE: DNA
<213> ORGANISM: Artificial sequence
<220> FEATURE:
<223> OTHER INFORMATION: Primer Rec1C_seq_F

<400> SEQUENCE: 78

```
cgttcatatt gatagtgatc ggttccttgg                                    30
```

<210> SEQ ID NO 79
<211> LENGTH: 30
<212> TYPE: DNA
<213> ORGANISM: Artificial sequence
<220> FEATURE:
<223> OTHER INFORMATION: Primer Rec1C_seq_R

<400> SEQUENCE: 79

```
catcaacaac tatgcttagt gtaggcgcaa                                    30
```

<210> SEQ ID NO 80
<211> LENGTH: 73
<212> TYPE: DNA
<213> ORGANISM: Artificial sequence
<220> FEATURE:
<223> OTHER INFORMATION: Primer Rec2_1_F

```
<400> SEQUENCE: 80
gttttcatct ccattaacat cccattacgc ttttattaag gagcattagc gatatcggaa      60
gccctgggcc aac                                                        73

<210> SEQ ID NO 81
<211> LENGTH: 75
<212> TYPE: DNA
<213> ORGANISM: Artificial sequence
<220> FEATURE:
<223> OTHER INFORMATION: Primer Rec2_1_R

<400> SEQUENCE: 81
atgttcacga cagaacagta aacaaccatc gcgaacgtat ctgcaactgc cacctgagac      60
aacttgttac agctc                                                      75

<210> SEQ ID NO 82
<211> LENGTH: 75
<212> TYPE: DNA
<213> ORGANISM: Artificial sequence
<220> FEATURE:
<223> OTHER INFORMATION: Primer ReC2_2_F

<400> SEQUENCE: 82
gttttcatct ccattaacat cccattacgc ttttattaag gagcattagc atgttctcac      60
cgcattcacg cttgc                                                      75

<210> SEQ ID NO 83
<211> LENGTH: 75
<212> TYPE: DNA
<213> ORGANISM: Artificial sequence
<220> FEATURE:
<223> OTHER INFORMATION: Primer ReC2_2_R

<400> SEQUENCE: 83
atgttcacga cagaacagta aacaaccatc gcgaacgtat ctgcaactgc atgacgcaag      60
cgtgaatgcg gtgag                                                      75

<210> SEQ ID NO 84
<211> LENGTH: 20
<212> TYPE: DNA
<213> ORGANISM: Artificial sequence
<220> FEATURE:
<223> OTHER INFORMATION: Primer Rec2_seq_F

<400> SEQUENCE: 84
caaaaaacga gccgttacgg                                                  20

<210> SEQ ID NO 85
<211> LENGTH: 20
<212> TYPE: DNA
<213> ORGANISM: Artificial sequence
<220> FEATURE:
<223> OTHER INFORMATION: Primer Rec2_seq_R

<400> SEQUENCE: 85
gacgggctaa ctttgcgtgc                                                  20

<210> SEQ ID NO 86
<211> LENGTH: 20
<212> TYPE: DNA
<213> ORGANISM: Artificial sequence
<220> FEATURE:
<223> OTHER INFORMATION: Primer Rec3_seq_F
```

<400> SEQUENCE: 86
caggtcgtgg tacttggggc                                          20

<210> SEQ ID NO 87
<211> LENGTH: 20
<212> TYPE: DNA
<213> ORGANISM: Artificial sequence
<220> FEATURE:
<223> OTHER INFORMATION: Primer Rec3B_seq_R

<400> SEQUENCE: 87
gtctgacatt cgccgtctgg                                          20

<210> SEQ ID NO 88
<211> LENGTH: 73
<212> TYPE: DNA
<213> ORGANISM: Artificial sequence
<220> FEATURE:
<223> OTHER INFORMATION: Primer Rec3B_1_F

<400> SEQUENCE: 88
ggccggcttt tttctggtaa tctcatgaat gtattgaggt tattagcgaa gatatcggaa    60
gccctgggcc aac                                                      73

<210> SEQ ID NO 89
<211> LENGTH: 75
<212> TYPE: DNA
<213> ORGANISM: Artificial sequence
<220> FEATURE:
<223> OTHER INFORMATION: Primer Rec3B_1_R

<400> SEQUENCE: 89
tacaaaattg ttaacaattt ttaaacaaca acggcaacc gatttgtcta cacctgagac     60
aacttgttac agctc                                                    75

<210> SEQ ID NO 90
<211> LENGTH: 22
<212> TYPE: DNA
<213> ORGANISM: Artificial sequence
<220> FEATURE:
<223> OTHER INFORMATION: Primer Rec3B_2_F

<400> SEQUENCE: 90
gaatgtattg aggttattag cg                                       22

<210> SEQ ID NO 91
<211> LENGTH: 20
<212> TYPE: DNA
<213> ORGANISM: Artificial sequence
<220> FEATURE:
<223> OTHER INFORMATION: Primer Rec3B_2_R

<400> SEQUENCE: 91
acgaatcttg tcaatatcgg                                          20

<210> SEQ ID NO 92
<211> LENGTH: 20
<212> TYPE: DNA
<213> ORGANISM: Artificial sequence
<220> FEATURE:
<223> OTHER INFORMATION: Primer Rec4_seq_F

<400> SEQUENCE: 92

```
tcgtcatctt agcccggatg                                                   20
```

<210> SEQ ID NO 93
<211> LENGTH: 20
<212> TYPE: DNA
<213> ORGANISM: Artificial sequence
<220> FEATURE:
<223> OTHER INFORMATION: Primer Rec4_seq_R

<400> SEQUENCE: 93

```
tgatggcgaa gcgtcgttcg                                                   20
```

<210> SEQ ID NO 94
<211> LENGTH: 73
<212> TYPE: DNA
<213> ORGANISM: Artificial sequence
<220> FEATURE:
<223> OTHER INFORMATION: Primer Rec4B_1_F

<400> SEQUENCE: 94

```
tgcgcgagta ccaggacatc atccgcgaag tcaaagacgc caacgcctga gatatcggaa       60
gccctgggcc aac                                                          73
```

<210> SEQ ID NO 95
<211> LENGTH: 75
<212> TYPE: DNA
<213> ORGANISM: Artificial sequence
<220> FEATURE:
<223> OTHER INFORMATION: Primer Rec4B_1_R

<400> SEQUENCE: 95

```
aaccccgac aagcgggggt tcgaagagga gttaatttgc cttaagtgta cacctgagac        60
aacttgttac agctc                                                        75
```

<210> SEQ ID NO 96
<211> LENGTH: 20
<212> TYPE: DNA
<213> ORGANISM: Artificial sequence
<220> FEATURE:
<223> OTHER INFORMATION: Primer Rec4B_2_F

<400> SEQUENCE: 96

```
aagctgatgc tgcaatctgc                                                   20
```

<210> SEQ ID NO 97
<211> LENGTH: 20
<212> TYPE: DNA
<213> ORGANISM: Artificial sequence
<220> FEATURE:
<223> OTHER INFORMATION: Primer Rec4B_2_R

<400> SEQUENCE: 97

```
gctaaaaacc cccgacaagc                                                   20
```

<210> SEQ ID NO 98
<211> LENGTH: 130
<212> TYPE: DNA
<213> ORGANISM: Artificial sequence
<220> FEATURE:
<223> OTHER INFORMATION: Primer ygaW Q5N

<400> SEQUENCE: 98

```
gttttcatct ccattaacat cccattacgc ttttattaag gagcattagc atgttctcac       60
cgaactcacg cttgcgtcat gcagttgcag atacgttcgc gatggttgtt tactgttctg      120
```
tcgtgaacat                                                          130

<210> SEQ ID NO 99
<211> LENGTH: 130
<212> TYPE: DNA
<213> ORGANISM: Artificial sequence
<220> FEATURE:
<223> OTHER INFORMATION: Primer ygaW Q5R

<400> SEQUENCE: 99
gttttcatct ccattaacat cccattacgc ttttattaag gagcattagc atgttctcac       60
cgtattcacg cttgcgtcat gcagttgcag atacgttcgc gatggttgtt tactgttctg      120
tcgtgaacat                                                             130

<210> SEQ ID NO 100
<211> LENGTH: 130
<212> TYPE: DNA
<213> ORGANISM: Artificial sequence
<220> FEATURE:
<223> OTHER INFORMATION: Primer ygaW Q5Y

<400> SEQUENCE: 100
gttttcatct ccattaacat cccattacgc ttttattaag gagcattagc atgttctcac       60
cgcgttcacg cttgcgtcat gcagttgcag atacgttcgc gatggttgtt tactgttctg      120
tcgtgaacat                                                             130

<210> SEQ ID NO 101
<211> LENGTH: 26
<212> TYPE: DNA
<213> ORGANISM: Artificial sequence
<220> FEATURE:
<223> OTHER INFORMATION: RT-qPCR primers for gene expression analysis
      ldhA_RT_F

<400> SEQUENCE: 101
caagaagtac ctgcaacagg tgaacg                                            26

<210> SEQ ID NO 102
<211> LENGTH: 21
<212> TYPE: DNA
<213> ORGANISM: Artificial sequence
<220> FEATURE:
<223> OTHER INFORMATION: RT-qPCR primers for gene expression analysis
      ldhA_RT_R

<400> SEQUENCE: 102
ataccgcttc gcagccattg g                                                 21

<210> SEQ ID NO 103
<211> LENGTH: 22
<212> TYPE: DNA
<213> ORGANISM: Artificial sequence
<220> FEATURE:
<223> OTHER INFORMATION: RT-qPCR primers for gene expression analysis
      alaD_RT_F

<400> SEQUENCE: 103
tgcggttatt gtgactaagg cg                                                22

<210> SEQ ID NO 104
<211> LENGTH: 20
<212> TYPE: DNA
<213> ORGANISM: Artificial sequence

```
<220> FEATURE:
<223> OTHER INFORMATION: RT-qPCR primers for gene expression analysis
      alaD_RT_R

<400> SEQUENCE: 104
gtgaacaaaa tcagacccgg                                                     20

<210> SEQ ID NO 105
<211> LENGTH: 25
<212> TYPE: DNA
<213> ORGANISM: Artificial sequence
<220> FEATURE:
<223> OTHER INFORMATION: RT-qPCR primers for gene expression analysis
      ygaW_RT_F

<400> SEQUENCE: 105
gcgatggttg tttactgttc tgtcg                                               25

<210> SEQ ID NO 106
<211> LENGTH: 21
<212> TYPE: DNA
<213> ORGANISM: Artificial sequence
<220> FEATURE:
<223> OTHER INFORMATION: RT-qPCR primers for gene expression analysis
      ygaW_RT_R

<400> SEQUENCE: 106
ccggaatcgc taccaatctg g                                                   21

<210> SEQ ID NO 107
<211> LENGTH: 22
<212> TYPE: DNA
<213> ORGANISM: Artificial sequence
<220> FEATURE:
<223> OTHER INFORMATION: RT-qPCR primers for gene expression analysis
      lpd_RT_F

<400> SEQUENCE: 107
ttactccgct gccttccgtt gc                                                  22

<210> SEQ ID NO 108
<211> LENGTH: 22
<212> TYPE: DNA
<213> ORGANISM: Artificial sequence
<220> FEATURE:
<223> OTHER INFORMATION: RT-qPCR primers for gene expression analysis
      lpd_RT_R

<400> SEQUENCE: 108
agggatacag ccgacgttca gg                                                  22

<210> SEQ ID NO 109
<211> LENGTH: 26
<212> TYPE: DNA
<213> ORGANISM: Artificial sequence
<220> FEATURE:
<223> OTHER INFORMATION: RT-qPCR primers for gene expression analysis
      zipA_RT_F

<400> SEQUENCE: 109
gccataatcg ctttactggt acatgg                                              26

<210> SEQ ID NO 110
<211> LENGTH: 23
<212> TYPE: DNA
<213> ORGANISM: Artificial sequence
<220> FEATURE:
```

<223> OTHER INFORMATION: RT-qPCR primers for gene expression analysis
zipA_RT_R

<400> SEQUENCE: 110
tcgtcacgtt ttgacttcat tcg                                            23

<210> SEQ ID NO 111
<211> LENGTH: 23
<212> TYPE: DNA
<213> ORGANISM: Artificial sequence
<220> FEATURE:
<223> OTHER INFORMATION: RT-qPCR primers for gene expression analysis
rrsA_RT_F

<400> SEQUENCE: 111
ctcttgccat cggatgtgcc cag                                            23

<210> SEQ ID NO 112
<211> LENGTH: 24
<212> TYPE: DNA
<213> ORGANISM: Artificial sequence
<220> FEATURE:
<223> OTHER INFORMATION: RT-qPCR primers for gene expression analysis
rrsA_RT_R

<400> SEQUENCE: 112
ccagtgtggc tggtcatcct ctca                                           24

<210> SEQ ID NO 113
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: lpd-pACYC_F

<400> SEQUENCE: 113
tatcatcgat aagcttctca tgaatgtatt gaggttatta gcg                      43

<210> SEQ ID NO 114
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: lpd-pACYC_R

<400> SEQUENCE: 114
aagggcatcg gtcgacggcg acaggaaagg taaattgc                            38

<210> SEQ ID NO 115
<211> LENGTH: 1110
<212> TYPE: DNA
<213> ORGANISM: Escherichia coli
<220> FEATURE:
<221> NAME/KEY: misc_feature
<223> OTHER INFORMATION: ackA-pta del locus

<400> SEQUENCE: 115
gtctttgagt aatgctgtcc ccggcgaaac aagctaaaaa aattaacaga acgattatcc    60
ggcgttgaca tgcttcacct caacttcaca tataaagatt caaaaatttg tgcaaattca   120
caactcagcg ggacaacgtt caaaacattt tgtcttccat acccactatc aggtatcctt   180
tagcagcctg aaggcctaag tagtacatat tcattgagtc gtcaaattca tatacattat    240
gccattggct gaaaattacg caaaatggca tagactcaag atatttcttc catcatgcaa    300
aaaaaatttg cagtgcatga tgttaatcat aaatgtcggt gtcatcatgc gctacgctct    360
atggctccct gacgtttttt tagccacgta tcaattatag gtacttccat gtcgagtaag    420
ttagtactgg ttctgaactg cggtagttct tcactgaaat ttgccatcat cgatgcagta    480
aatggtgaag agtacctttc tggtttagcc gaatgtttcc acctgcccga agcacgtatc    540
aaatggaaaa tggacggcaa taaacaggaa gcggctttag gtgcaggcgc cgctcacagc    600
gaagcgctca actttatcaa ttaaccctca ctaaagggcg gccgcgaagt tcctattctc    660
tagaaagtat aggaacttcc tcgagcccta gtgagttc gtattagccg atgctgcagg    720
gtatgcgcaa gccggttaac gacctgtccc gtggcgcact ggttgacgat atcgtctaca    780
ccatcgcgct gactgcgatt cagtctgcac agcagcagta atctcgtcat catccgcagc    840
tttgcgctgc ggatatctga accggaaata atcactattt ccggtttttt attctcttaa    900
tctgcattaa tcctttctga ttatcttgct taactgcgct gcatcaatga attgcgccat    960
ttcactttgc atacttacca ctttgttttg tgcaagggaa tatttgcgct atgtccgcaa   1020
tcactgaatc caaaccaaca agaagatggg caatgcccga tacgttggtg attatctttt   1080
ttgttgctat tttaaccagc cttgccacct                                    1110

<210> SEQ ID NO 116
<211> LENGTH: 1179
<212> TYPE: DNA
<213> ORGANISM: Escherichia coli
<220> FEATURE:
<221> NAME/KEY: misc_feature
<223> OTHER INFORMATION: adhE del locus

<400> SEQUENCE: 116
caggttggct gtaaggttag ttttgtttcg cgctgccgct gtctgataac tggtcatgct     60
gataaagacg ggaataatcc ctaccgggtt gaccagcgca ataacccga tgaaaaattt    120 gaagtaaacg ggaaaatcaa aaaaggtctg aatcacggtt agctccgaag caaaagccgg    180
ataatgttag ccataaataa ggttgaaaag acgcgctgac aatacgcctt ttgacagcat    240
ttttcacctc ctaactactt aaaattgcta tcattcgtta ttgttatcta gttgtgcaaa    300
acatgctaat gtagccacca atcatacta caatttatta actgttagct ataatggcga    360
aaagcgatgc tgaaaggtgt cagctttgca aaaatttgat ttggatcacg taatcagtac    420
ccagaagtga gtaatcttgc ttacgccacc tggaagtgac gcattagaga taataactct    480
aatgtttaaa ctcttttagt aaatcacagt gagtgtgagc gcgagtaagc ttttgatttt    540
cataggttaa gcaaatcatc accgcactga ctatactctc gtattcgagc agatgattta    600
ctaaaaaagt ttaacattat caggagagca ttatggctgt tactaatgtc gctgaactta    660
acgcactcgt agagcgtgta aaaattaacc ctcactaaag gcggaagtt cctattctct    720 agaaagtata ggaacttcga gccctaatga actccgtgct aaagaagccg ctccggctaa    780
agctgagaaa aaagcgaaaa aatccgctta atcagtagcc ctgtctggca atataaacgg    840
ccccttctgg ggccgttttt tgtttaccc aaagcaactt ttccataaac cgacagcatt    900
agccttcatc atatttgcga cgatgtataa cgcctaaaca cagggatatt gtactttaca    960
ggtcacaagt caacgtcggt gcttaagagc cctgtgaggc gtatagcggc gttaaaaaac   1020
tgccgagaag ggtatatagc ccggaagaag tgcgtaaaac gaactgacag gataaaagtg   1080

```
cccmtgctcac cctgtcagta aagaaattct tattaatcgt ggcgatgcct ttcctgaata    1140
gccgttaatg agccgacttg taacgcctct atatagtgt                            1179
```

<210> SEQ ID NO 117
<211> LENGTH: 1136
<212> TYPE: DNA
<213> ORGANISM: Escherichia coli
<220> FEATURE:
<221> NAME/KEY: misc_feature
<223> OTHER INFORMATION: frd del locus

<400> SEQUENCE: 117

```
ccagcaggcg tttcatatgg tattccgggc tggtcattaa ccagagattc atccctgcg      60 aatgcccggg gccaacgaaa cgtgtctcaa acgggaccaa atgaatatcg gttaccgtcg    120
cctggctcat acaaggcgtc tccacctcca gcactccacg atcggcaaag aaacgacgga    180
tctccgccat aatcgccgcg cgttttaata agttaggaat ggatgcgctc ggctgccagg    240
atgccgtttc gctcatagtt aaatctccag tttttgacaa gggcacgaag tctactcgca    300
acgcgacggc gagacaaatt ttacgcagga atcaaacagc ggtgggcagt gactaaaaaa    360
agcacgatct gatggtttag taattaaatt aatcatcttc agtgataatt tagccctctt    420
gcgcactaaa aaatcgatc tcgtcaaatt tcagacttat ccatcagact atactgttgt    480
acctataaag gagcagtgga atagcgttcg cagaccgtaa ctttcaggta cttaccctga    540
agtacgtggc tgtgggataa aaacaatctg gaggaatgtc gtgcaaacct ttcaagccga    600
tcttgccatt gtaggcgccg gtggcgcggg aattaaccct cactaaaggg cggaagttcc    660
tattctctag aaagtatagg aacttcgagc cctaatgaac tccgtgctaa cgcgatgcac    720
gatctgaaaa ttcacgtgcc tgcgggcaaa tgggttttct acggtctggc tgctatcctg    780
acagttgtca cgctgattgg tatcgttaca atctaacgta tcgccaatgt aaatccggcc    840
cgcctatggc gggccgtttt gtatggaaac cagacccttat gttcaaaacg acgtctgcg    900 ccttattaat tacctcctct tgctccacat ttgctgcccc tcaacaaatc aacgatattg    960
tgcatcgcac aattaccccg cttatagagc aacaaaagat ccccggtatg gcggtggcgg   1020
taatttatca gggtaaacct tattacttta cctggggcta tgcggacatc gccaaaaagc   1080
agcccgtcac acagcaaacg ttgtttgagt taggttcggt cagcaaaaca tttacg       1136
```

<210> SEQ ID NO 118
<211> LENGTH: 759
<212> TYPE: DNA
<213> ORGANISM: Escherichia coli
<220> FEATURE:
<221> NAME/KEY: misc_feature
<223> OTHER INFORMATION: pflB del locus

<400> SEQUENCE: 118

```
taatccgcga cttcgcatct ccggaattct ggaccgctgt cggttctgca ccggaaaatt     60
tttctcacct gaccgtgatg aacttcatca ctgataacct gattccggtt acgatcggta    120
atattatcgg cggtggtttg ttggttgggt tgacatactg ggtcatttac ctgcgtgaaa    180
acgatcacca ttaatggttg tcgaagtacg cagtaaataa aaaatccact taagaaggta    240
ggtgttacat gtccgagctt aatgaaaagt tagccacagc ctgggaaggt tttaccaaaa    300
ttaaccctca ctaaagggcg gaagttccta ttctctagaa agtataggaa cttcgagccc    360
taatgaactc cgtgctaaag aacagcagca ggacgttatt actcgtacct tcactcaatc    420
```

```
tatgtaatta gatttgactg aaatcgtaca gtaaaaagcg tacaataaag gctccacgaa      480 agtgggcct  tttttagcac gagagccttt tttgtcagct atctatactt taaggtgact      540
gccaaaacag actcgacgta gccttcgagc tgcgcaccaa cacggcctca gatgggccac      600
atctggagaa acaccgcaat gtcagttatt ggtcgcattc actcctttga atcctgtgga      660
accgtagacg gcccaggtat tcgctttatc acctttttcc agggctgcct gatgcgctgc      720
ctgtattgtc ataaccgcga cacctgggat acgcatggc                             759
```

<210> SEQ ID NO 119
<211> LENGTH: 2022
<212> TYPE: DNA
<213> ORGANISM: Escherichia coli
<220> FEATURE:
<221> NAME/KEY: misc_feature
<223> OTHER INFORMATION: ldhA-alaD locus

<400> SEQUENCE: 119

```
gagggttttt ggagcagctg gcgattgctc cgtctgcggc aatttcgcca gacaagcaga       60
atcaagttct accgtgccga cgttcaataa ccagcggctg ggatgtgaaa ggctggcgtt      120
ggtgatatgc gcaagctgac aatctcccac cagataacgg agatcgggaa tgattaaacc      180
tttacgcgta atgcgtgggc tttcatctaa tgcaatacgt gtcccgagcg gtagccagat      240
gcccgccagc gtgggaaccc acagcccgag cgtcatcagc agcgtcaacg gcacaagaat      300
aatcagtaat aacagcgcga gaacggcttt atatttaccc agcatgggta gttaatatcc      360
tgatttagcg aaaaattaag cattcaatac gggtattgtg gcatgtttaa ccgttcagtt      420
gaaggttgcg cctacactaa gcatagttgt tgatgaattt ttcaatatcg ccatagcttt      480
caattatatt tgaaattttg taaaatattt ttagtagctt aaatgtgatt caacatcact      540
ggagaaagtc ttatgaaaat tggcatccct aaagagatta agaacaatga aaaccgtgta      600
gcaatcaccc cggcaggtgt tatgactctg gttaaagcgg gccacgatgt gtacgtcgaa      660
accgaagcgg gtgccggcag cggcttcagc gacagcgagt atgagaaggc gggtgcggtt      720
attgtgacta aggcggagga cgcttgggca gccgaaatgg ttctgaaggt gaaagaaccg      780
ctggcggagg agtttcgcta ttttcgtccg ggtctgattt tgttcaccta cctgcacctg      840
gctgcggccg aggcgctgac caaggcactg gtggagcaga aggttgttgg catcgcgtac      900
gaaacggttc aactggcgaa tggttccctg ccgctgctga cccctatgtc tgaagttgcg      960
ggtcgcatga gcgttcaagt cggcgctcag tttctggaga accgcacgg tggcaagggc     1020 attttgctgg gtggtgttcc gggtgtccgc cgtggtaaag tgacgatcat tggcggtggt     1080
acggccggta cgaacgcggc caagattgcc gtaggtctgg gtgcagatgt gaccattctg     1140
gacatcaacg cggaacgttt gcgtgagctg acgatctgt ttggcgacca agtcaccacc     1200
ctgatgagca acagctacca catcgcggag tgcgtccgtg aaagcgattt ggtcgttggt     1260
gcggtgctga tcccgggtgc aaaagccccg aaactggtga ccgaggagat ggtccgtagc     1320 atgacccgg gttcggttct ggtcgacgtg caattgacc agggcggtat cttcgaaacc     1380
accgaccgcg tcacgaccca tgatgacccg acctatgtga acatggcgt ggttcactat     1440 gcggtcgcga atatgccggg tgcagtgccg cgcacgtcca cgttcgcgct gacgaacgtg     1500
acgattccat acgctctgca gatcgccaat aagggctatc gtcggcgtg tctggataat     1560 ccggcattgc tgaaaggcat caatacccctg gatggtcata tcgtttacga ggctgtggct     1620
gcagcacaca acatgccgta cactgatgtc catagcttgc tgcaaggcta aaattaaccc     1680
```

| tcactaaagg gcggaagttc ctattctcta gaaagtatag gaacttcgag ccctaatgaa | 1740 |
| ctccgtgcta tcttgccgct cccctgcatt ccagggagc tgattcagat aatcccaat | 1800 |
| gacctttcat cctctattct taaaatagcc ctgagtcaga aactgtaatt gagaaccaca | 1860 |
| atgaagaaag tagccgcgct cgttgcgcta agcctgctga tggcgggatg tgtaagtaat | 1920 |
| gacaaaattg ctgtaacgcc agaacagtta cagcatcatc gttttgtgct ggaaagcgta | 1980 |
| aacggtaagc ccgtgaccaa cgataaaaat ccgccagaaa tc | 2022 |

<210> SEQ ID NO 120
<211> LENGTH: 848
<212> TYPE: DNA
<213> ORGANISM: Escherichia coli
<220> FEATURE:
<221> NAME/KEY: misc_feature
<223> OTHER INFORMATION: ydbH-ldhA locus Ex1

<400> SEQUENCE: 120

| gcggcatagt aaattccccc accagtttaa ccggcggctg attttcaaac gcgacgacat | 60 |
| ccagttcgct gactgtaagt tgttgcccct tcagctggcc ttgaaattta acttttttcgc | 120 |
| cctgataacg cagttgctgg atatcagagg ttaatgcgag agagagtttt ccctgccatt | 180 |
| cctgccaggg agaaaaaatc agtttatcga tattgatcca ggtgttaggc agcatggact | 240 |
| gccactgcgc gagggttttt ggagcagctg gcgattgctc cgtctgcggc aatttcgcca | 300 |
| gacaagcaga atcaagttct accgtgccga cgttcaataa ccagcggctg ggatgtgaaa | 360 |
| ggctggcgtt ggtgatatgc gcaagctgac aatctcccac cagataacgg agatcgggaa | 420 |
| tgattaaacc tttacgcgta atgcgtgggc tttcatctaa tgcaatacgt gtcccgagcg | 480 |
| gtagccagat gcccgccagc gtgggaaccc acagcccgag cgtcatcagc agcgtcaacg | 540 |
| gcacaagaat aatcagtaat aacagcgcga gaacggcttt atatttaccc agcatgggta | 600 |
| gttaatatcc tgatttagcg aaaaattaag cattcaatac gggtattgtg gcatgtttaa | 660 |
| ccgttcagtt gaaggttgcg cctacactaa gcatagttgt tgatgaattt ttcaatatcg | 720 |
| ccatagcttt caattatatt tgaaattttg taaaatattt ttagtagctt aaatgtgatt | 780 |
| caacatcact ggagaaagtc ttatgaaact cgccgtttat agcacaaaac agtacgacaa | 840 |
| gaagtacc | 848 |

<210> SEQ ID NO 121
<211> LENGTH: 596
<212> TYPE: DNA
<213> ORGANISM: Escherichia coli
<220> FEATURE:
<221> NAME/KEY: misc_feature
<223> OTHER INFORMATION: ydbH-alaD locus Ev2

<400> SEQUENCE: 121

| gagggttttt ggagcagctg gcgattgctc cgtctgcggc aatttcgcca gacaagcaga | 60 |
| atcaagttct accgtgccga cgttcaataa ccagcggctg gatgtgaaa ggctggcgtt | 120 |
| ggtgatatgc gcaagctgac aatctcccac cagataacgg agatcgggaa tgattaaacc | 180 |
| tttacgcgta atgcgtgggc tttcatctaa tgcaatacgt gtcccgagcg gtagccagat | 240 |
| gcccgccagc gtgggaaccc acagcccgag cgtcatcagc agcgtcaacg gcacaagaat | 300 |
| aatcagtaat aacagcgcga gaacggcttt atatttaccc agcatgggta gttaatatcc | 360 |
| tgatttagcg aaaaattaag cattcaatac gggtattgtg gcatgtttaa ccgttcagtt | 420 |
| gaaggttgcg cctacactaa gcatagttgt tgatgaattt ttcaatatcg ccatagcttt | 480 |

-continued

```
caattatatt tgaaattttg taaaatattt ttagtagctt aaatgtgatt caacatcact      540
ggagaaagtc ttatgaaaat tggcatccct aaagagatta agaacaatga aaaccg          596
```

<210> SEQ ID NO 122
<211> LENGTH: 317
<212> TYPE: DNA
<213> ORGANISM: Escherichia coli
<220> FEATURE:
<221> NAME/KEY: misc_feature
<223> OTHER INFORMATION: ydbH-alaD locus Ev3

<400> SEQUENCE: 122

```
gcggcatagt aaattccccc accagtttaa ccggcggctg attttcaaac gcgacgacat       60
ccagttcgct gactgtaagt tgttgcccct tcagctggcc ttgaaattta acttttttcgc    120 cctgataacg cagttgctgg atatcagagg ttaatgcgag agagagtttt ccctgccatt     180
cctgccaggg agaaaaaatc agtttatcga tattgatttt gtaaaatatt tttagtagct     240
taaatgtgat tcaacatcac tggagaaagt cttatgaaaa ttggcatccc taaagagatt     300
aagaacaatg aaaaccg                                                    317
```

<210> SEQ ID NO 123
<211> LENGTH: 70
<212> TYPE: PRT
<213> ORGANISM: Escherichia coli

<400> SEQUENCE: 123

```
Met Ser Ser Lys Leu Val Leu Val Leu Asn Cys Gly Ser Ser Ser Leu
 1               5                  10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile
65                  70
```

<210> SEQ ID NO 124
<211> LENGTH: 21
<212> TYPE: PRT
<213> ORGANISM: Escherichia coli

<400> SEQUENCE: 124

```
Met Ala Val Thr Asn Val Ala Glu Leu Asn Ala Leu Val Glu Arg Val
 1               5                  10                  15

Lys Ile Asn Pro His
            20
```

<210> SEQ ID NO 125
<211> LENGTH: 21
<212> TYPE: PRT
<213> ORGANISM: Escherichia coli

<400> SEQUENCE: 125

```
Val Gln Thr Phe Gln Ala Asp Leu Ala Ile Val Gly Ala Gly Gly Ala
 1               5                  10                  15

Gly Ile Asn Pro His
            20
```

```
<210> SEQ ID NO 126
<211> LENGTH: 21
<212> TYPE: PRT
<213> ORGANISM: Escherichia coli

<400> SEQUENCE: 126

Met Ser Glu Leu Asn Glu Lys Leu Ala Thr Ala Trp Glu Gly Phe Thr
1               5                   10                  15

Lys Ile Asn Pro His
            20
```